United States Patent
Ibrahim et al.

(10) Patent No.: US 10,160,790 B2
(45) Date of Patent: Dec. 25, 2018

(54) HYR1-DERIVED COMPOSITIONS AND METHODS OF TREATMENT USING SAME

(75) Inventors: Ashraf S. Ibrahim, Irvine, CA (US); Michael R. Yeaman, Redondo Beach, CA (US); John E. Edwards, Jr., Palos Verdes Estates, CA (US); Guanpingsheng Luo, Torrance, CA (US); Yue Fu, Carson, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 24 days.

(21) Appl. No.: 14/344,838

(22) PCT Filed: Sep. 14, 2012

(86) PCT No.: PCT/US2012/055604
§ 371 (c)(1),
(2), (4) Date: Feb. 11, 2015

(87) PCT Pub. No.: WO2013/040478
PCT Pub. Date: Mar. 21, 2013

(65) Prior Publication Data
US 2015/0191514 A1 Jul. 9, 2015

Related U.S. Application Data

(60) Provisional application No. 61/534,734, filed on Sep. 14, 2011, provisional application No. 61/564,201, filed on Nov. 28, 2011.

(51) Int. Cl.
*C07K 14/40* (2006.01)
*A61K 47/64* (2017.01)
*A61K 39/00* (2006.01)
*C07K 16/14* (2006.01)

(52) U.S. Cl.
CPC .......... *C07K 14/40* (2013.01); *A61K 39/0002* (2013.01); *A61K 47/646* (2017.08); *C07K 16/14* (2013.01); *A61K 39/00* (2013.01); *A61K 2039/6081* (2013.01)

(58) Field of Classification Search
None
See application file for complete search history.

(56) References Cited

U.S. PATENT DOCUMENTS

2010/0150942 A1 6/2010 Cantor
2012/0237534 A1 9/2012 Fu et al.
2014/0335114 A1 11/2014 Fu et al.

FOREIGN PATENT DOCUMENTS

WO WO-2011003085 A1 1/2011

OTHER PUBLICATIONS

Harlow et al. Antibodies: A Laboratory Manual. Edited by Ed Harlow and David Lane. Cold Spring Harbor Laboratory. New York. 1988, p. 74.*
Tian et al. Journal of Clinical Microbiology, vol. 45, No. 9, Sep. 2007, p. 2971-2978.*
Huang et al. Vaccine 21 (2003) 2500-2505.*
Betts et al. Bioinformatics for Geneticists. Edited by Michael R. Barnes and Ian C. Gray. Chapter 14. 2003 John Wiley and Sons, Ltd p. 289-316.*
International Search Report for International Patent Application No. PCT/US12/55604, dated Mar. 8, 2013.
Written Opinion of the International Search Authority for International Application No. PCT/US12/55604, dated Mar. 8, 2013.
International Preliminary Report on Patentability for International Application No. PCT/US12/55604, dated Mar. 18, 2014.
Kramer et al., "How long do nosocomial pathogens persist on inanimate surfaces? A systematic review," BMC Infect Dis. 6:130 (2006).
Peleg et al., "Prokaryote-eukaryote interactions identified by using Caenorhaditis elegans," PNAS 105:14585-14590 (2008).
Choi et al., "Acinetobacter baumannii invades epithelial cells and outer membrane protein A mediates interactions with epithelial cells," BMC Microbiology 8:216 (2008).
NCBI_YP_001084998, putative outer membran protein [Acinetobacter baumannii ATCC 17978] May 29, 2010[online]. [Retrieved on Nov. 27, 2012]. Retrieved from the Internet: <URL:http://www.ncbi.nlm.nih.gov/protein/126642014.
Smith et al., "New insights into Acinetobacter baumannii pathogenesis revealed by high-density pyrosequencing and transposon mutagenesis," Genes Dev. 21:601-614 (2007).
Soares et al., "2-DE analysis indicates that Acinetobacter baumannii displays a robust and versatile metabolism," Proteome Science 7:37 (2009).
Supplementary European Search Report for European Patent Application No. 12832321.9, dated Jun. 3, 2015 (9 pages).
Luo et al., "Candida albicans Hyr1p confers resistance to neutrophil killing and is a potential vaccine target," J Infect Dis. 201(11):1718-1728 (2010).
Luo et al., "Active and passive immunization with rHyr1p-N protects mice against hematogenously disseminated candidiasis," PLoS One. 6(10):e25909 (2011) (8 pages).
Pietrella et al., "A beta-glucan-conjugate vaccine and anti-beta-glucan antibodies are effective against murine vaginal candidiasis as assessed by a novel in vivo imaging technique," Vaccine. 28(7):1717-1725 (2010).

(Continued)

*Primary Examiner* — Oluwatosin A Ogunbiyi
(74) *Attorney, Agent, or Firm* — Pillsbury Winthrop Shaw Pittmann LLP

(57) ABSTRACT

The disclosure features isolated polypeptides of Hyr1. The disclosure further features vaccines and antibodies useful in treating or preventing candidiasis or *Acinetobacter* infections or both. Further disclosed are isolated polypeptides consisting of between 14 and 20 amino acids for vaccine preparation. The specific amino acid sequences of isolated polypeptides of Hyr1 are also disclosed.

16 Claims, 11 Drawing Sheets

Specification includes a Sequence Listing.

(56) References Cited

OTHER PUBLICATIONS

First Office Action for Chinese Patent Application No. 201280056018.2, dated Mar. 14, 2016 (English language translation provided) (27 pages).

Notice of Reasons for Rejection for Japanese Patent Application No. 2014-530899, dated Jul. 21, 2016 (English language translation provided) (14 pages).

* cited by examiner

SEQUENCE LISTING

```
<160> NUMBER OF SEQ ID NOS: 31

<210> SEQ ID NO 1
<211> LENGTH: 937
<212> TYPE: PRT
<213> ORGANISM: Candida albicans

<400> SEQUENCE: 1

Met Lys Val Val Ser Asn Phe Ile Phe Thr Ile Leu Leu Thr Leu Asn
1               5                   10                  15

Leu Ser Ala Ala Leu Glu Val Val Thr Ser Arg Ile Asp Arg Gly Gly
            20                  25                  30

Ile Gln Gly Phe His Gly Asp Val Lys Val His Ser Gly Ala Thr Trp
        35                  40                  45

Ala Ile Leu Gly Thr Thr Leu Cys Ser Phe Phe Gly Gly Leu Glu Val
    50                  55                  60

Glu Lys Gly Ala Ser Leu Phe Ile Lys Ser Asp Asn Gly Pro Val Leu
65                  70                  75                  80

Ala Leu Asn Val Ala Leu Ser Thr Leu Val Arg Pro Val Ile Asn Asn
                85                  90                  95

Gly Val Ile Ser Leu Asn Ser Lys Ser Ser Thr Ser Phe Ser Asn Phe
            100                 105                 110

Asp Ile Gly Gly Ser Ser Phe Thr Asn Asn Gly Glu Ile Tyr Leu Ala
        115                 120                 125

Ser Ser Gly Leu Val Lys Ser Thr Ala Tyr Leu Tyr Ala Arg Glu Trp
    130                 135                 140

Thr Asn Asn Gly Leu Ile Val Ala Tyr Gln Asn Gln Lys Ala Ala Gly
145                 150                 155                 160

Asn Ile Ala Phe Gly Thr Ala Tyr Gln Thr Ile Thr Asn Asn Gly Gln
```

```
                        165                 170                 175
        Ile Cys Leu Arg His Gln Asp Phe Val Pro Ala Thr Lys Ile Lys Gly
                        180                 185                 190

Thr Gly Cys Val Thr Ala Asp Glu Asp Thr Trp Ile Lys Leu Gly Asn
                        195                 200                 205

Thr Ile Leu Ser Val Glu Pro Thr His Asn Phe Tyr Leu Lys Asp Ser
                        210                 215                 220

Lys Ser Ser Leu Ile Val His Ala Val Ser Ser Asn Gln Thr Phe Thr
        225                 230                 235                 240

Val His Gly Phe Gly Asn Gly Asn Lys Leu Gly Leu Thr Leu Pro Leu
                        245                 250                 255

Thr Gly Asn Arg Asp His Phe Arg Phe Glu Tyr Tyr Pro Asp Thr Gly
                        260                 265                 270

Ile Leu Gln Leu Arg Ala Ala Leu Pro Gln Tyr Phe Lys Ile Gly
                        275                 280                 285

Lys Gly Tyr Asp Ser Lys Leu Phe Arg Ile Val Asn Ser Arg Gly Leu
                        290                 295                 300

Lys Asn Ala Val Thr Tyr Asp Gly Pro Val Pro Asn Asn Glu Ile Pro
        305                 310                 315                 320

Ala Val Cys Leu Ile Pro Cys Thr Asn Gly Pro Ser Ala Pro Glu Ser
                        325                 330                 335

Glu Ser Asp Leu Asn Thr Pro Thr Thr Ser Ser Ile Glu Thr Ser Ser
                        340                 345                 350

Tyr Ser Ser Ala Ala Thr Glu Ser Ser Val Val Ser Glu Ser Ser
                        355                 360                 365

Ala Val Asp Ser Leu Thr Ser Ser Leu Ser Ser Lys Ser Glu Ser
                        370                 375                 380

Ser Asp Val Val Ser Ser Thr Thr Asn Ile Glu Ser Ser Ser Thr Ala
        385                 390                 395                 400

Ile Glu Thr Thr Met Asn Ser Glu Ser Ser Thr Asp Ala Gly Ser Ser
                        405                 410                 415

Ser Ile Ser Gln Ser Glu Ser Ser Thr Ala Ile Thr Ser Ser Ser
                        420                 425                 430

Glu Thr Ser Ser Ser Glu Ser Met Ser Ala Ser Ser Thr Thr Ala Ser
                        435                 440                 445

Asn Thr Ser Ile Glu Thr Asp Ser Gly Ile Val Ser Gln Ser Glu Ser
                        450                 455                 460

Ser Ser Asn Ala Leu Ser Ser Thr Glu Gln Ser Ile Thr Ser Ser Pro
        465                 470                 475                 480

Gly Gln Ser Thr Ile Tyr Val Asn Ser Thr Val Thr Ser Thr Ile Thr
                        485                 490                 495

Ser Cys Asp Glu Asn Lys Cys Thr Glu Asp Val Val Thr Ile Phe Thr
                        500                 505                 510

Thr Val Pro Cys Ser Thr Asp Cys Val Pro Thr Thr Gly Asp Ile Pro
                        515                 520                 525

Met Ser Thr Ser Tyr Thr Gln Arg Thr Val Thr Ser Thr Ile Thr Asn
                        530                 535                 540

Cys Asp Glu Val Ser Cys Ser Gln Asp Val Val Thr Tyr Thr Thr Asn
        545                 550                 555                 560

Val Pro His Thr Thr Val Asp Ala Thr Thr Thr Thr Thr Ser Thr
                        565                 570                 575

Gly Gly Asp Asn Ser Thr Gly Gly Asn Glu Ser Gly Ser Asn His Gly
                        580                 585                 590
```

```
Pro Gly Asn Gly Ser Thr Glu Gly Ser Gly Asn Gly Ser Gly Ala Gly
        595                 600                 605

Ser Asn Glu Gly Ser Gln Ser Gly Pro Asn Asn Gly Ser Gly Ser Gly
        610                 615                 620

Ser Glu Gly Gly Ser Asn Asn Gly Ser Gly Ser Asp Ser Gly Ser Asn
625                 630                 635                 640

Asn Gly Ser Gly Ser Gly Ser Asn Asn Gly Gly Ser Gly Ser Gly Thr
        645                 650                 655

Glu Gly Ser Glu Gly Gly Ser Gly Ser Asn Glu Gly Ser Gln Ser Gly
        660                 665                 670

Ser Gly Ser Gln Pro Gly Pro Asn Glu Gly Ser Glu Gly Gly Ser Gly
        675                 680                 685

Ser Asn Glu Gly Ser Asn His Gly Ser Asn Glu Gly Ser Gly Ser Gly
        690                 695                 700

Ser Gly Ser Gly Ser Asn Asn Gly Ser Gly Ser Gly Ser Gln Ser Gly
705                 710                 715                 720

Ser Gly Ser Gly Ser Gln Ser Gly Ser Glu Ser Gly Ser Asn Ser Gly
        725                 730                 735

Ser Asn Glu Gly Ser Asn Pro Gly Ala Gly Asn Gly Ser Asn Glu Gly
        740                 745                 750

Ser Gly Gln Gly Ser Gly Asn Gly Ser Glu Ala Gly Ser Gly Gln Gly
        755                 760                 765

Ser Gly Pro Asn Asn Gly Ser Gly Ser Gly His Asn Asp Gly Ser Gly
        770                 775                 780

Ser Gly Ser Asn Gln Gly Ser Asn Pro Gly Ala Gly Ser Gly Ser Gly
785                 790                 795                 800

Ser Glu Ser Gly Ser Asn Ala Gly Ser His Ser Gly Ser Asn Glu Gly
        805                 810                 815

Ala Lys Thr Asp Ser Ile Glu Gly Phe His Thr Glu Ser Lys Pro Gly
        820                 825                 830

Phe Asn Thr Gly Ala His Thr Asp Ala Thr Val Thr Gly Asn Ser Val
        835                 840                 845

Ala Asn Pro Val Thr Thr Ser Thr Glu Ser Asp Thr Thr Ile Ser Val
        850                 855                 860

Thr Val Ser Ile Thr Ser Tyr Met Thr Gly Phe Asp Gly Lys Pro Lys
865                 870                 875                 880

Pro Phe Thr Thr Val Asp Val Ile Pro Val Pro His Ser Met Pro Ser
        885                 890                 895

Asn Thr Thr Asp Ser Ser Ser Val Pro Thr Ile Asp Thr Asn Glu
        900                 905                 910

Asn Gly Ser Ser Ile Val Thr Gly Gly Lys Ser Ile Leu Phe Gly Leu
        915                 920                 925

Ile Val Ser Met Val Val Leu Phe Met
        930                 935

<210> SEQ ID NO 2
<211> LENGTH: 326
<212> TYPE: PRT
<213> ORGANISM: Candida albicans

<400> SEQUENCE: 2

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
```

```
                    20                  25                  30
        Ser Phe Phe Gly Gly Leu Glu Val Glu Lys Gly Ala Ser Leu Phe Ile
                    35                  40                  45

Lys Ser Asp Asn Gly Pro Val Leu Ala Leu Asn Val Ala Leu Ser Thr
                    50                  55                  60

Leu Val Arg Pro Val Ile Asn Asn Gly Val Ile Ser Leu Asn Ser Lys
         65                  70                  75                  80

Ser Ser Thr Ser Phe Ser Asn Phe Asp Ile Gly Gly Ser Ser Phe Thr
                            85                  90                  95

Asn Asn Gly Glu Ile Tyr Leu Ala Ser Ser Gly Leu Val Lys Ser Thr
                        100                 105                 110

Ala Tyr Leu Tyr Ala Arg Glu Trp Thr Asn Asn Gly Leu Ile Val Ala
                    115                 120                 125

Tyr Gln Asn Gln Lys Ala Ala Gly Asn Ile Ala Phe Gly Thr Ala Tyr
                130                 135                 140

Gln Thr Ile Thr Asn Asn Gly Gln Ile Cys Leu Arg His Gln Asp Phe
        145                 150                 155                 160

Val Pro Ala Thr Lys Ile Lys Gly Thr Gly Cys Val Thr Ala Asp Glu
                            165                 170                 175

Asp Thr Trp Ile Lys Leu Gly Asn Thr Ile Leu Ser Val Glu Pro Thr
                        180                 185                 190

His Asn Phe Tyr Leu Lys Asp Ser Lys Ser Ser Leu Ile Val His Ala
                    195                 200                 205

Val Ser Ser Asn Gln Thr Phe Thr Val His Gly Phe Gly Asn Gly Asn
                210                 215                 220

Lys Leu Gly Leu Thr Leu Pro Leu Thr Gly Asn Arg Asp His Phe Arg
        225                 230                 235                 240

Phe Glu Tyr Tyr Pro Asp Thr Gly Ile Leu Gln Leu Arg Ala Ala Ala
                            245                 250                 255

Leu Pro Gln Tyr Phe Lys Ile Gly Lys Gly Tyr Asp Ser Lys Leu Phe
                        260                 265                 270

Arg Ile Val Asn Ser Arg Gly Leu Lys Asn Ala Val Thr Tyr Asp Gly
                    275                 280                 285

Pro Val Pro Asn Asn Glu Ile Pro Ala Val Cys Leu Ile Pro Cys Thr
                290                 295                 300

Asn Gly Pro Ser Ala Pro Glu Ser Glu Ser Asp Leu Asn Thr Pro Thr
        305                 310                 315                 320

Thr Ser Ser Ile Glu Thr
                        325

<210> SEQ ID NO 3
<211> LENGTH: 14
<212> TYPE: PRT
<213> ORGANISM: Candida albicans

<400> SEQUENCE: 3

Gly Pro Ser Ala Pro Glu Ser Glu Ser Asp Leu Asn Thr Pro
 1               5                  10

<210> SEQ ID NO 4
<211> LENGTH: 14
<212> TYPE: PRT
<213> ORGANISM: Candida albicans

<400> SEQUENCE: 4

Gly Asn Arg Asp His Phe Arg Phe Glu Tyr Tyr Pro Asp Thr
```

```
<210> SEQ ID NO 5
<211> LENGTH: 14
<212> TYPE: PRT
<213> ORGANISM: Candida albicans

<400> SEQUENCE: 5

Gly Asn Arg Asp His Phe Arg Phe Glu Tyr Tyr Pro Asp Thr
1               5                   10

<210> SEQ ID NO 6
<211> LENGTH: 14
<212> TYPE: PRT
<213> ORGANISM: Candida albicans

<400> SEQUENCE: 6

Lys Ile Lys Gly Thr Gly Cys Val Thr Ala Asp Glu Asp Thr
1               5                   10

<210> SEQ ID NO 7
<211> LENGTH: 14
<212> TYPE: PRT
<213> ORGANISM: Candida albicans

<400> SEQUENCE: 7

Leu Lys Asn Ala Val Thr Tyr Asp Gly Pro Val Pro Asn Asn
1               5                   10

<210> SEQ ID NO 8
<211> LENGTH: 14
<212> TYPE: PRT
<213> ORGANISM: Candida albicans

<400> SEQUENCE: 8

Asn Ser Lys Ser Ser Thr Ser Phe Ser Asn Phe Asp Ile Gly
1               5                   10

<210> SEQ ID NO 9
<211> LENGTH: 14
<212> TYPE: PRT
<213> ORGANISM: Candida albicans

<400> SEQUENCE: 9

Glu Pro Thr His Asn Phe Tyr Leu Lys Asp Ser Lys Ser Ser
1               5                   10

<210> SEQ ID NO 10
<211> LENGTH: 14
<212> TYPE: PRT
<213> ORGANISM: Candida albicans

<400> SEQUENCE: 10

Thr Ser Arg Ile Asp Arg Gly Gly Ile Gln Gly Phe His Gly
1               5                   10

<210> SEQ ID NO 11
<211> LENGTH: 15
<212> TYPE: PRT
<213> ORGANISM: Candida albicans

<400> SEQUENCE: 11

Cys Gly Pro Ser Ala Pro Glu Ser Glu Ser Asp Leu Asn Thr Pro
1               5                   10                  15
```

<210> SEQ ID NO 12
<211> LENGTH: 15
<212> TYPE: PRT
<213> ORGANISM: Candida albicans

<400> SEQUENCE: 12

Cys Gly Asn Arg Asp His Phe Arg Phe Glu Tyr Tyr Pro Asp Thr
1               5                   10                  15

<210> SEQ ID NO 13
<211> LENGTH: 15
<212> TYPE: PRT
<213> ORGANISM: Candida albicans

<400> SEQUENCE: 13

Cys Gly Tyr Asp Ser Lys Leu Phe Arg Ile Val Asn Ser Arg Gly
1               5                   10                  15

<210> SEQ ID NO 14
<211> LENGTH: 15
<212> TYPE: PRT
<213> ORGANISM: Candida albicans

<400> SEQUENCE: 14

Cys Lys Ile Lys Gly Thr Gly Cys Val Thr Ala Asp Glu Asp Thr
1               5                   10                  15

<210> SEQ ID NO 15
<211> LENGTH: 15
<212> TYPE: PRT
<213> ORGANISM: Candida albicans

<400> SEQUENCE: 15

Cys Leu Lys Asn Ala Val Thr Tyr Asp Gly Pro Val Pro Asn Asn
1               5                   10                  15

<210> SEQ ID NO 16
<211> LENGTH: 15
<212> TYPE: PRT
<213> ORGANISM: Candida albicans

<400> SEQUENCE: 16

Asn Ser Lys Ser Ser Thr Ser Phe Ser Asn Phe Asp Ile Gly Cys
1               5                   10                  15

<210> SEQ ID NO 17
<211> LENGTH: 15
<212> TYPE: PRT
<213> ORGANISM: Candida albicans

<400> SEQUENCE: 17

Cys Glu Pro Thr His Asn Phe Tyr Leu Lys Asp Ser Lys Ser Ser
1               5                   10                  15

<210> SEQ ID NO 18
<211> LENGTH: 15
<212> TYPE: PRT
<213> ORGANISM: Candida albicans

<400> SEQUENCE: 18

Thr Ser Arg Ile Asp Arg Gly Gly Ile Gln Gly Phe His Gly Cys
1               5                   10                  15

<210> SEQ ID NO 19

<211> LENGTH: 829
<212> TYPE: PRT
<213> ORGANISM: Acinetobacter baumannii

<400> SEQUENCE: 19

```
Met Pro Leu Ala Leu Val Ser Ala Met Ala Val Gln Gln Ala Tyr
1               5                   10                  15

Ala Ala Asp Asp Phe Val Val Arg Asp Ile Arg Val Asn Gly Leu Val
            20                  25                  30

Arg Leu Thr Pro Ala Asn Val Tyr Thr Met Leu Pro Ile Asn Ser Gly
        35                  40                  45

Asp Arg Val Asn Glu Pro Met Ile Ala Glu Ala Ile Arg Thr Leu Tyr
50                  55                  60

Leu Thr Gly Leu Phe Asp Asp Ile Lys Ala Ser Lys Glu Asn Asp Thr
65                  70                  75                  80

Leu Val Phe Asn Val Ile Glu Arg Pro Ile Ile Ser Lys Leu Glu Phe
                85                  90                  95

Lys Gly Asn Lys Leu Ile Pro Lys Glu Ala Leu Glu Gln Gly Leu Lys
            100                 105                 110

Lys Met Gly Ile Ala Glu Gly Glu Val Phe Lys Lys Ser Ala Leu Gln
        115                 120                 125

Thr Ile Glu Thr Glu Leu Glu Gln Gln Tyr Thr Gln Gln Gly Arg Tyr
130                 135                 140

Asp Ala Asp Val Thr Val Asp Thr Val Ala Arg Pro Asn Asn Arg Val
145                 150                 155                 160

Glu Leu Lys Ile Asn Phe Asn Glu Gly Thr Pro Ala Lys Val Phe Asp
                165                 170                 175

Ile Asn Val Ile Gly Asn Thr Val Phe Lys Asp Ser Glu Ile Lys Gln
            180                 185                 190

Ala Phe Ala Val Lys Glu Ser Gly Trp Ala Ser Val Val Thr Arg Asn
        195                 200                 205

Asp Arg Tyr Ala Arg Glu Lys Met Ala Ala Ser Leu Glu Ala Leu Arg
210                 215                 220

Ala Met Tyr Leu Asn Lys Gly Tyr Ile Asn Phe Asn Ile Asn Asn Ser
225                 230                 235                 240

Gln Leu Asn Ile Ser Glu Asp Lys Lys His Ile Phe Ile Glu Val Ala
                245                 250                 255

Val Asp Glu Gly Ser Gln Phe Lys Phe Gly Gln Thr Lys Phe Leu Gly
            260                 265                 270

Asp Ala Leu Tyr Lys Pro Glu Glu Leu Gln Ala Leu Lys Ile Tyr Lys
        275                 280                 285

Asp Gly Asp Thr Tyr Ser Gln Glu Lys Val Asn Ala Val Lys Gln Leu
290                 295                 300

Leu Leu Arg Lys Tyr Gly Asn Ala Gly Tyr Tyr Phe Ala Asp Val Asn
305                 310                 315                 320

Ile Val Pro Gln Ile Asn Asn Glu Thr Gly Val Val Asp Leu Asn Tyr
                325                 330                 335

Tyr Val Asn Pro Gly Gln Gln Val Thr Val Arg Arg Ile Asn Phe Thr
            340                 345                 350

Gly Asn Ser Lys Thr Ser Asp Glu Val Leu Arg Arg Glu Met Arg Gln
        355                 360                 365

Met Glu Gly Ala Leu Ala Ser Asn Glu Lys Ile Asp Leu Ser Lys Val
370                 375                 380

Arg Leu Glu Arg Thr Gly Phe Phe Lys Thr Val Asp Ile Lys Pro Ala
```

-continued

```
            385                 390                 395                 400
        Arg Ile Pro Asn Ser Pro Asp Gln Val Asp Leu Asn Val Asn Val Glu
                            405                 410                 415

Glu Gln His Ser Gly Thr Thr Leu Ala Val Gly Tyr Ser Gln Ser
                    420                 425                 430

Gly Gly Ile Thr Phe Gln Ala Gly Leu Ser Gln Thr Asn Phe Met Gly
                        435                 440                 445

Thr Gly Asn Arg Val Ala Ile Asp Leu Ser Arg Ser Glu Thr Gln Asp
                    450                 455                 460

Tyr Tyr Asn Leu Ser Val Thr Asp Pro Tyr Phe Thr Ile Asp Gly Val
        465                 470                 475                 480

Ser Arg Gly Tyr Asn Val Tyr Arg Lys Thr Lys Leu Asn Asp Asp
                        485                 490                 495

Tyr Asn Val Asn Asn Tyr Val Thr Asp Ser Phe Gly Gly Ser Leu Ser
                        500                 505                 510

Phe Gly Tyr Pro Ile Asp Glu Asn Gln Ser Leu Ser Ala Ser Val Gly
                    515                 520                 525

Val Asp Asn Thr Lys Val Thr Thr Gly Ala Phe Val Ser Thr Tyr Val
        530                 535                 540

Arg Asp Tyr Leu Leu Ala Asn Gly Gly Lys Thr Thr Ser Thr Asn Thr
        545                 550                 555                 560

Tyr Cys Leu Val Asp Leu Val Gln Asp Pro Gln Thr Gly Leu Tyr Lys
                            565                 570                 575

Cys Pro Glu Gly Gln Thr Ser Gln Pro Tyr Gly Asn Ala Phe Glu Gly
                        580                 585                 590

Glu Phe Phe Thr Tyr Asn Leu Asn Leu Gly Trp Ser Tyr Asn Thr Leu
                    595                 600                 605

Asn Arg Pro Ile Phe Pro Thr Ser Gly Met Ser His Arg Val Gly Leu
                    610                 615                 620

Glu Ile Gly Leu Pro Gly Ser Asp Val Asp Tyr Gln Lys Val Thr Tyr
        625                 630                 635                 640

Asp Thr Gln Ala Phe Phe Pro Ile Gly Ser Thr Gly Phe Val Leu Arg
                            645                 650                 655

Gly Tyr Gly Lys Leu Gly Tyr Gly Asn Asp Leu Pro Phe Tyr Lys Asn
                        660                 665                 670

Phe Tyr Ala Gly Gly Tyr Gly Ser Val Arg Gly Tyr Asp Asn Ser Thr
                    675                 680                 685

Leu Gly Pro Lys Tyr Ala Ser Val Asn Leu Gln Glu Glu Lys Lys Asn
            690                 695                 700

Asp Ser Ser Pro Glu Glu Val Gly Gly Asn Ala Leu Val Gln Phe Gly
        705                 710                 715                 720

Thr Glu Leu Val Leu Pro Met Pro Phe Lys Gly Asp Trp Thr Arg Gln
                            725                 730                 735

Val Arg Pro Val Leu Phe Ala Glu Gly Gly Gln Val Phe Asp Thr Lys
                        740                 745                 750

Cys Asp Val Arg Ser Tyr Ser Met Ile Met Asn Gly Gln Gln Ile Ser
                    755                 760                 765

Asp Ala Lys Lys Tyr Cys Glu Asp Asn Tyr Gly Phe Asp Leu Gly Asn
            770                 775                 780

Leu Arg Tyr Ser Val Gly Val Gly Val Thr Trp Ile Thr Met Ile Gly
        785                 790                 795                 800

Pro Leu Ser Leu Ser Tyr Ala Phe Pro Leu Asn Asp Lys Pro Gly Asp
                            805                 810                 815
```

Glu Thr Lys Glu Ile Gln Phe Glu Ile Gly Arg Thr Phe
            820                 825

<210> SEQ ID NO 20
<211> LENGTH: 424
<212> TYPE: PRT
<213> ORGANISM: Acinetobacter baumannii

<400> SEQUENCE: 20

Met Leu Lys Ala Gln Lys Leu Thr Leu Ala Val Leu Ile Ser Ala Ala
1               5                   10                  15

Ile Ile Ser Ser Ala Gln Ala Ser Glu Gln Ser Glu Ala Lys Gly Phe
            20                  25                  30

Val Glu Asp Ala Asn Gly Ser Ile Leu Phe Arg Thr Gly Tyr Ile Ser
        35                  40                  45

Arg Asp Lys Lys Asp Gly Arg Ala Asp Asn Ser Ser Phe Ala Gln Thr
    50                  55                  60

Ala Ile Val Asn Ile Asp Ser Gly Phe Thr Pro Gly Ile Val Gly Phe
65                  70                  75                  80

Gly Val Gly Val Val Gly Asp Gly Ser Phe Lys Ile Gly Glu Asn Lys
                85                  90                  95

Asn Ala Gly Asn Asn Met Ile Pro Gln His Asn Asp Gly Ser Ala Tyr
            100                 105                 110

Asp His Trp Ala Arg Gly Gly Ala Asn Val Lys Ala Arg Phe Ser Asn
        115                 120                 125

Thr Thr Val Arg Tyr Gly Thr Gln Val Leu Asp Leu Pro Val Leu Ala
    130                 135                 140

Ser Asn Thr Ala Arg Leu Val Pro Glu Tyr Phe Thr Gly Thr Leu Leu
145                 150                 155                 160

Thr Ser His Glu Ile Lys Asp Leu Glu Val Val Ala Gly Lys Phe Thr
                165                 170                 175

Lys Asn Gln Tyr Ser Asp Gln Ile Ala Thr Asp Gln Asn Gly Leu Asp
            180                 185                 190

Arg Ala Val Val Trp Gly Ala Lys Tyr Lys Phe Asp Asp Gln Ile Ser
        195                 200                 205

Gly Ser Tyr Tyr Gly Val Asp Val Lys Asp Lys Leu Asp Arg His Tyr
    210                 215                 220

Val Asn Val Asn Tyr Lys Gln Pro Leu Ala Asn Asp Ser Ser Leu Thr
225                 230                 235                 240

Tyr Asp Phe Ser Gly Tyr His Thr Lys Phe Asp Lys Gly Ala Asn Leu
                245                 250                 255

Ser Tyr Ala Thr Gly Pro Ala Asp Glu Asp Lys Thr Asn Asn Ile Trp
            260                 265                 270

Ala Ile Ser Gly Thr Tyr Ala Thr Gly Pro His Ser Val Met Leu Ala
        275                 280                 285

Tyr Gln Gln Asn Ser Gly Asn Ile Gly Tyr Asn Tyr Gly Val Asn Gln
    290                 295                 300

Asp Gly Gly Gln Ser Val Tyr Leu Pro Asn Ser Tyr Leu Ser Asp Phe
305                 310                 315                 320

Ile Gly Asn Asp Glu Lys Ser Ala Gln Ile Gln Tyr Ser Leu Asp Phe
                325                 330                 335

Gly Lys Leu Gly Val Leu Pro Gly Leu Asn Trp Thr Thr Ala Tyr Val
            340                 345                 350

Tyr Gly Trp Asp Ile Lys Thr Ser Asn Gly Ala Asp Asp Ser Asn Glu

```
            355                 360                 365
Ser Glu Phe Phe Asn Gln Val Lys Tyr Thr Val Gln Ser Gly Phe Ala
    370                 375                 380

Lys Gly Ser Ser Leu Arg Leu Arg Asn Ser Ile Tyr Arg Ala Asp Asn
385                 390                 395                 400

Ala Tyr Thr Thr Asp Tyr Met Pro Asp Thr Asn Glu Trp Arg Ile Phe
                405                 410                 415

Leu Asp Ile Pro Val Thr Leu Phe
            420

<210> SEQ ID NO 21
<211> LENGTH: 746
<212> TYPE: PRT
<213> ORGANISM: Acinetobacter baumannii

<400> SEQUENCE: 21

Met Thr Pro Cys Cys Leu Ala Ile Ser Ala Ile Phe Ala Gln Gln Ala
1               5                   10                  15

Tyr Ala Glu Thr Val Thr Gln Thr Ala Glu Val Ser Glu Asn Ala Thr
                20                  25                  30

Gln Lys Pro Val Ala Gln Leu Gln Lys Ile Val Val Thr Ala Thr Arg
            35                  40                  45

Thr Pro Lys Asn Ile Ala Glu Ile Ala Gly Thr Val Gln Ser Ile Asp
        50                  55                  60

Gln Lys Gln Ile Ile Gln Ala Thr Ala Gly Arg Lys Val Ala Asp
65                  70                  75                  80

Ile Leu Ala Gln Leu Val Pro Ser Leu Ala Ser Ser Gly Thr Thr
                85                  90                  95

Ser Asn Tyr Gly Gln Thr Met Arg Gly Arg Asn Val Leu Val Met Ile
            100                 105                 110

Asp Gly Val Ser Gln Thr Gly Ser Arg Asp Val Ser Arg Gln Leu Asn
        115                 120                 125

Ser Ile Ser Pro Gly Met Ile Glu Arg Ile Glu Val Ile Ser Gly Ala
    130                 135                 140

Thr Ser Ile Tyr Gly Ser Gly Ala Thr Gly Gly Ile Ile Asn Ile Ile
145                 150                 155                 160

Thr Lys Arg Ala Asp Thr Ser Lys Pro Leu Ser Phe Glu Thr Lys Val
                165                 170                 175

Gly Ile Thr Ser Ser Asp Thr Phe Arg Ser Asp Gly Leu Ala Tyr Glu
            180                 185                 190

Val Gly Gln Ser Val Ser Phe Asn Lys Gly Asn Ile Asp Gly Phe Leu
        195                 200                 205

Gly Ala Asn Phe Thr Ser Arg Gly Ser Gln Phe Asp Gly Asn Gly Asp
    210                 215                 220

Arg Ile Ser Leu Ser Pro Trp Gln Gly Ser Thr Met Asp Thr Asp Thr
225                 230                 235                 240

Ile Asp Val Asn Gly Arg Leu Asn Phe Asn Leu Asn Asp Thr Gln Thr
                245                 250                 255

Leu Ser Phe Gly Ala Gln Tyr Tyr Lys Asp Lys Gln Asp Thr Asp Tyr
            260                 265                 270

Gly Pro Asp Tyr Ser Tyr Leu Pro Thr Thr Ser Lys Ser Asn Asp Ala
        275                 280                 285

Thr Thr Pro Thr Tyr Lys Ala Ile Lys Gly Leu Lys Leu Ser Asn Pro
    290                 295                 300
```

```
Leu Phe Thr Glu Arg Tyr Ala Val Asn Ser Gln Tyr Gln Asn Gln Asp
305                 310                 315                 320

Phe Leu Gly Gln Ile Leu Asn Val Glu Ala Tyr Tyr Arg Asn Glu Lys
                325                 330                 335

Ser Arg Phe Phe Pro Tyr Gly Leu Ser Asn Lys Ser Val Thr Ser Val
            340                 345                 350

Asn Gln Ser Gln Ser Glu Ile Glu Val Ala Gly Leu Arg Ser Thr Met
        355                 360                 365

Gln Thr Asp Leu Asn Ile Ala Asn Arg Asp Met Lys Ile Thr Tyr Gly
    370                 375                 380

Leu Asp Tyr Asp Trp Glu Lys Asp Lys Gln Phe Val Asp Ile Leu Ala
385                 390                 395                 400

Thr Gln Tyr Pro Tyr Leu Val Tyr Thr Pro Thr Gly Gln Arg Lys Gly
                405                 410                 415

Tyr Gly Pro Asn Thr Glu Ile Gln Asn Ile Gly Ala Phe Val Gln Ser
            420                 425                 430

Asp Tyr Ala Val Thr Asp Lys Leu Asn Leu Gln Ala Gly Ile Arg Tyr
        435                 440                 445

Gln Tyr Ile Gln Ala Asp Thr Asp Ala Tyr Ile Pro Ser Arg Glu Thr
    450                 455                 460

Thr Met Val Pro Ala Gly Ser Thr His Asp Asp Lys Pro Leu Phe Asn
465                 470                 475                 480

Leu Gly Ala Val Tyr Lys Leu Thr Asp Ala Gln Val Tyr Ala Asn
                485                 490                 495

Phe Ser Gln Gly Phe Ser Phe Pro Asp Val Gln Arg Met Leu Arg Asp
            500                 505                 510

Val Ser Thr Tyr Thr Val Ser Thr Ala Asn Leu Gln Pro Ile Thr Val
        515                 520                 525

Asn Ser Tyr Glu Leu Gly Trp Arg Leu Asn Gln Asp Asp Gly Leu Asn
    530                 535                 540

Leu Gly Leu Thr Gly Phe Tyr Asn Thr Ser Asp Lys Thr Val Gln Phe
545                 550                 555                 560

Asn Asn Arg Ala Ala Lys Val Val Asp Thr Asp Gln Arg Val Tyr Gly
                565                 570                 575

Ala Glu Ala Thr Ile Ser Tyr Pro Phe Met Glu Asn Tyr Lys Val Gly
            580                 585                 590

Gly Thr Leu Gly Tyr Thr Arg Gly Gln Tyr Lys Asp Val Ala Asn Lys
        595                 600                 605

Trp His Glu Leu Asn Ser Phe Thr Val Ala Pro Val Lys Gly Thr Leu
    610                 615                 620

Phe Ala Glu Trp Asp Asn Asn Glu Gly Tyr Gly Val Arg Val Gln Met
625                 630                 635                 640

Gln Ala Ile Lys Gly Thr Asn Lys Ala Tyr Lys Asp Asp Arg Glu Leu
                645                 650                 655

Ala Ala Phe Ala Thr Thr Gln Asp Glu Ala Phe Gln Asn Ala Val Lys
            660                 665                 670

Asn Asp Ala Asn Ser Ala Ala Gln Ile Lys Gly Tyr Thr Thr Met Asp
        675                 680                 685

Val Leu Ala His Phe Pro Ala Trp Lys Gly Arg Val Asp Phe Gly Val
    690                 695                 700

Tyr Asn Val Trp Asn Arg Gln Tyr Arg Thr Val Phe Ala Gln Gln Ala
705                 710                 715                 720

Ala Val Ser Asn Ala Asn Pro Leu Leu Ala Ile Pro Ala Glu Gly Arg
```

```
                   725                 730                 735
Thr Tyr Gly Leu Ser Tyr Thr Phe Asn Tyr
                740                 745

<210> SEQ ID NO 22
<211> LENGTH: 736
<212> TYPE: PRT
<213> ORGANISM: Acinetobacter baumannii

<400> SEQUENCE: 22

Met Ala Gln Glu Ala Val Ser Gln Leu Pro Thr Ile His Thr Lys Ala
1               5                   10                  15

Thr Gln Glu Glu Ser Leu Lys Val Asp Gln Ser Ala Asn Ser Lys Phe
            20                  25                  30

Val Ala Pro Leu Lys Asp Thr Pro Lys Ser Val Ser Ile Leu Ser Gln
        35                  40                  45

Lys Leu Ile Lys Asp Thr Asn Ser Asn Thr Leu Leu Glu Ala Leu Arg
    50                  55                  60

Tyr Glu Pro Gly Ile Thr Leu Gly Ala Gly Glu Gly Gly Thr Pro Phe
65                  70                  75                  80

Thr Asp Met Pro Tyr Ile Arg Gly Tyr Ser Gly Gln Ser Ser Ile Tyr
                85                  90                  95

Val Asp Gly Val Arg Asn Thr Thr Ser Gln Asn Arg Asp Met Phe Ala
            100                 105                 110

Ile Glu Gln Val Glu Val Ile Lys Gly Ser Ser Ala Leu Gly Gly
        115                 120                 125

Gly Gly Ser Val Gly Gly Ser Ile Asn Leu Ile Pro Lys Val Ala His
    130                 135                 140

Glu Gly Asp Val Tyr Gln Gly Ser Val Gln Ser Gly Thr Asp Asn Tyr
145                 150                 155                 160

Arg His Ile Gln Leu Asp Ala Asn Lys Asp Phe Gly Asn Gly Ile Ala
                165                 170                 175

Gly Arg Val Val Ile Met Gly His Glu Asn Glu Lys Ala Gly Gln Ser
            180                 185                 190

Asn Gly Ala Glu Tyr Lys Arg Val Gly Ile Ala Pro Ser Ile Thr Phe
        195                 200                 205

Gly Leu Asp Thr Ala Thr Arg Gly Thr Leu Ser Tyr Tyr Tyr Leu Arg
    210                 215                 220

Ser Asn Asp Glu Pro Asp Ala Gly Ile Pro Phe Asn Asn Ala Asn Pro
225                 230                 235                 240

Ala Lys Pro Pro Val Gly Val Thr Val Thr Pro Gly Asp Gly Lys Pro
                245                 250                 255

Val Asp Val Lys Ala Gly Thr Tyr Tyr Gly Trp Lys Ala Arg Asp Phe
            260                 265                 270

Asp Lys Arg Glu Asn His Ile Gly Thr Phe Lys Leu Glu His Asp Phe
        275                 280                 285

Asn Glu Asn Leu Thr Leu Ser Asn Ile Ala Thr Tyr Asn Lys Ser Lys
    290                 295                 300

Ser Asp Tyr Val Tyr Thr Asn Ala Asp Ser Lys Gly Asn Ile Tyr
305                 310                 315                 320

Arg Gly Thr Val Ala Arg Arg Ala Leu Ser Arg Ile Leu Asp Thr Asp
                325                 330                 335

Ala Tyr Ser Asp Gln Leu Ser Leu Arg Gly Lys Phe Asn Thr Gly Ser
            340                 345                 350
```

```
Leu Lys His Ser Phe Asn Val Gly Thr Glu Trp Ser Phe Gln Glu Thr
            355                 360                 365

Asp Gln Gly Val His Thr Phe Thr Asn Ala Ala Gly Glu Thr Thr Ser
        370                 375                 380

Thr Ile Leu Asp Ser Asn Ile Gln Asn Cys Thr Ser Ala Ala Ala Val
385                 390                 395                 400

Ala Asn Gly Trp Cys Thr Ser Leu Asn Pro Gly Asn Gly Ala Phe
                405                 410                 415

Thr Asp Lys Arg Gly Ser Ile Thr Ala Gln Ser Thr Arg Ser His
                420                 425                 430

Asn Val Gly Ile Tyr Ala Leu Asp Ser Ile Glu Phe Asn Pro Gln Trp
            435                 440                 445

Leu Leu Asn Leu Gly Val Arg Trp Asp Lys Phe Glu Thr Glu Lys Lys
            450                 455                 460

Tyr Asn Lys Asp Val Asp Gly Arg Thr Pro His Lys Ala Gly Asp Lys
465                 470                 475                 480

Leu Glu Ser Asp Thr Asp Tyr Phe Ser Tyr Gln Ala Gly Leu Val Phe
                485                 490                 495

Lys Pro Thr Glu Asp Gly Ser Ile Tyr Leu Ser Tyr Ala Thr Ser Ala
            500                 505                 510

Asn Pro Val Gly Val Leu Ala Glu Gly Asp Thr Gly Ser Asp Ser Ile
            515                 520                 525

Ser Asp Ser Gly Thr Ala Ser Ala Ser Ala Asn Ala Leu Lys Pro Glu
        530                 535                 540

Glu Ala Arg Thr Phe Glu Leu Gly Thr Lys Trp Asp Leu Phe Asn Asn
545                 550                 555                 560

Arg Ala Asn Leu Thr Ala Ala Val Phe Arg Thr Glu Lys Gln Asn Thr
                565                 570                 575

Arg Ile Gln Ile Asp Pro Thr Thr Ala Asn Ala Gly Lys Ser Lys
            580                 585                 590

Val Asp Gly Phe Glu Ile Ser Leu Asn Gly Lys Ile Thr Asp Lys Trp
            595                 600                 605

Asp Val Ser Thr Gly Tyr Ser Tyr Leu Asp Ser Glu Ile Thr Glu Ala
610                 615                 620

Ala Tyr Asn Ala Val Ala Gln Glu Gly Lys Pro Leu Pro Phe Val Ala
625                 630                 635                 640

Lys Asn Ser Ala Thr Leu Trp Ser Thr Tyr Arg Val Met Pro Gln Leu
                645                 650                 655

Thr Leu Gly Ala Gly Val Glu Tyr Arg Asp Gln Val Phe Val Asn Thr
            660                 665                 670

Thr Ala Pro Lys Tyr Leu Pro Thr Tyr Thr Ile Tyr Asn Ala Met Ala
            675                 680                 685

Lys Tyr Asp Val Asn Lys Asn Val Asn Leu Gln Leu Asn Ile Asn Asn
            690                 695                 700

Ile Ser Asp Lys Arg Tyr Phe Thr Ser Ala His Ala Ala His Tyr Ala
705                 710                 715                 720

Phe Glu Gly Asn Gly Arg Asn Ala Val Leu Ala Ile Asn Phe Lys Tyr
                725                 730                 735

<210> SEQ ID NO 23
<211> LENGTH: 543
<212> TYPE: PRT
<213> ORGANISM: Acinetobacter baumannii

<400> SEQUENCE: 23
```

-continued

```
Met Thr Thr Ser His Ala Glu Glu Thr Ala Glu Gln Gln Asn Ser Thr
1               5                   10                  15

Asn Val Leu Pro Thr Ile Ser Ile Gln Ala Gln Lys Glu Asn Pro Thr
                20                  25                  30

Ser Tyr Val Ala Thr Lys Ala Asn Ser Ala Leu Lys Ser Asp Ala Pro
            35                  40                  45

Leu Phe Lys Thr Ala Gln Ser Val Ser Val Thr Arg Glu Gln Leu
50                  55                  60

Asp Gln Lys Gln Ala Arg Thr Leu Thr Asp Ala Leu Glu Gly Val Ala
65                  70                  75                  80

Gly Val Glu Ala Gly Lys Leu Gly Arg Arg Gly Trp Asp Asp Phe Ile
                85                  90                  95

Ile Arg Gly Gln Thr Ser Ser Asp Ser Val Tyr Val Asp Gly Leu Arg
                100                 105                 110

Val Gly Gln Asn Thr Tyr Val Ala Thr Glu Leu Ser Gly Met Asp Gln
            115                 120                 125

Val Gln Ile Leu Lys Gly Pro Ala Ser Ile Asn Phe Gly Leu Val Ala
130                 135                 140

Pro Gly Gly Met Val Asn Leu Val Thr Lys Arg Pro Glu Ala Glu Ser
145                 150                 155                 160

Phe Ala Arg Ala Ser Met Thr Tyr Gly Ser Tyr Ser Leu Lys Glu Gly
                165                 170                 175

Thr Phe Asp Leu Asn Tyr Ser Pro Asn Asn Ser Glu Lys Gly Ala Phe
            180                 185                 190

Arg Leu Asn Gly Arg Ile Ser Asp Gln Asp Pro Thr Asp Tyr Val
                195                 200                 205

Tyr Phe Lys Asn Phe Tyr Ile Ser Pro Ser Tyr Asn Phe Asp Leu Gly
            210                 215                 220

Asp Asn Thr Asp Leu Ser Val Ser Ala Ser Tyr Gln His Arg Glu Tyr
225                 230                 235                 240

Ile Arg Gln Gln Gly Leu Pro Val Ile Gly Thr Leu Lys Asn Asn Pro
                245                 250                 255

Asn Gly Pro Ile Asp Arg Ser Leu Tyr Ile Gly Asp Pro Asn Phe Gly
            260                 265                 270

Lys Tyr Glu Ala Asp Val Tyr Arg Thr Gly Tyr Thr Phe Lys His Thr
            275                 280                 285

Phe Asp Asn Gly Trp Asn Phe Asn Gln Asn Phe Ala Val Gln Lys Thr
290                 295                 300

Glu Met Asp Gly Lys Ala Val Phe Ala Arg Thr Gly Ser Asn Phe Trp
305                 310                 315                 320

Ala Lys Asp Lys Gln Gly Glu Ile Asp Tyr Thr Thr Ile Ser Arg Arg
                325                 330                 335

Asn Asn Ser Arg His Gln Val Ile Asp Asn Leu Ser Phe Ala Ile Asp
            340                 345                 350

Asn Arg Leu Asn Lys Gln Phe Asp Leu Tyr Gly Met Gln His Asp Ile
            355                 360                 365

Asn Ile Gly Val Asp Ala Phe Gln Glu Lys Ser Asp Tyr Thr Asn Asp
370                 375                 380

Lys Tyr Asp Ile Gly Asp Leu Asn Ile Tyr Asn Pro Val Tyr Gly Gln
385                 390                 395                 400

Asn Val Thr Leu Lys Gln Asn Val Arg Asp Ile Asn Arg Leu Lys Tyr
                405                 410                 415
```

```
Leu Gly Leu Tyr Leu Arg Asp Arg Ile Gln Leu Asn Asp Gln Leu Leu
                420                 425                 430

Leu Ser Leu Ser Gly Arg Gln Asp Trp Ala Gln Thr Gln Thr Thr Ser
            435                 440                 445

Leu Val Thr Gly Asn Ala Ser Lys Gln Ser Asp Asn Ala Phe Thr Gly
        450                 455                 460

Ser Ala Ser Val Met Tyr Thr Leu Asn Asp Ile Val Ala Pro Tyr Val
465                 470                 475                 480

Ser Tyr Ala Thr Ser Phe Thr Pro Asn Ser Gly Thr Asp Val Asn Ser
                485                 490                 495

Asn Pro Phe Lys Pro Glu Lys Gly Lys Gln Val Glu Val Gly Met Lys
            500                 505                 510

Leu Gln Ser Pro Gly Gln Arg Ile Gln Gly Ala Ile Ala Trp Tyr Asp
        515                 520                 525

Leu Lys Arg Gln Asn Val Leu Val Thr Asp Thr Ala Asn Ser Gly
530                 535                 540

<210> SEQ ID NO 24
<211> LENGTH: 598
<212> TYPE: PRT
<213> ORGANISM: Acinetobacter baumannii

<400> SEQUENCE: 24

Met Gly Gln Ser Ala Lys Arg Gln Ala Val Thr Asn Pro Lys Asn Thr
1               5                   10                  15

Leu Phe Ala Ile Lys Arg Leu Ile Gly Arg Arg Tyr Glu Asp Gln Ala
            20                  25                  30

Val Gln Lys Asp Ile Gly Leu Val Pro Tyr Lys Ile Ile Lys Ala Asp
        35                  40                  45

Asn Gly Asp Ala Trp Val Glu Val Asn Asp Lys Lys Leu Ala Pro Gln
    50                  55                  60

Gln Ile Ser Ala Glu Ile Leu Lys Lys Met Lys Lys Thr Ala Glu Asp
65                  70                  75                  80

Tyr Leu Gly Glu Thr Val Thr Glu Ala Val Ile Thr Val Pro Ala Tyr
                85                  90                  95

Phe Asn Asp Ala Gln Arg Gln Ala Thr Lys Asp Ala Gly Lys Ile Ala
            100                 105                 110

Gly Leu Asp Val Lys Arg Ile Ile Asn Glu Pro Thr Ala Ala Ala Leu
        115                 120                 125

Ala Phe Gly Met Asp Lys Lys Glu Gly Asp Arg Lys Val Ala Val Tyr
    130                 135                 140

Asp Leu Gly Gly Gly Thr Phe Asp Val Ser Ile Ile Glu Ile Ala Asp
145                 150                 155                 160

Leu Asp Gly Asp Gln Gln Ile Glu Val Leu Ser Thr Asn Gly Asp Thr
                165                 170                 175

Phe Leu Gly Gly Glu Asp Phe Asp Asn Ala Leu Ile Glu Tyr Leu Val
            180                 185                 190

Glu Glu Phe Lys Lys Glu Gln Asn Val Asn Leu Lys Asn Asp Pro Leu
        195                 200                 205

Ala Leu Gln Arg Leu Lys Glu Ala Ala Glu Lys Ala Lys Ile Glu Leu
    210                 215                 220

Ser Ser Ser Asn Ala Thr Glu Ile Asn Leu Pro Tyr Ile Thr Ala Asp
225                 230                 235                 240

Ala Thr Gly Pro Lys His Leu Val Ile Asn Val Thr Arg Ala Lys Leu
                245                 250                 255
```

```
Glu Gly Leu Val Ala Asp Leu Val Ala Arg Thr Ile Glu Pro Cys Lys
            260                 265                 270

Ile Ala Leu Lys Asp Ala Gly Leu Ser Thr Ser Asp Ile Ser Asp Val
        275                 280                 285

Ile Leu Val Gly Gly Gln Ser Arg Met Pro Leu Val Gln Gln Lys Val
    290                 295                 300

Gln Glu Phe Phe Gly Arg Glu Pro Arg Lys Asp Val Asn Pro Asp Glu
305                 310                 315                 320

Ala Val Ala Ile Gly Ala Ile Gln Gly Ala Val Leu Ser Gly Asp
                325                 330                 335

Lys Asn Asp Val Leu Leu Leu Asp Val Thr Pro Leu Thr Leu Gly Ile
                340                 345                 350

Glu Thr Met Gly Gly Val Leu Thr Pro Ile Ile Glu Lys Asn Thr Thr
            355                 360                 365

Ile Pro Ala Lys Lys Ser Gln Val Phe Ser Thr Ala Ala Asp Asn Gln
        370                 375                 380

Pro Ala Val Asp Ile Ser Val Tyr Gln Gly Glu Arg Lys Met Ala Gln
385                 390                 395                 400

Gln Asn Lys Leu Leu Gly Asn Phe Gln Leu Gly Asp Ile Pro Pro Ala
                405                 410                 415

Pro Arg Gly Val Pro Gln Ile Glu Val Ser Phe Asp Ile Asn Ala Asp
                420                 425                 430

Gly Ile Leu Lys Val Ser Ala Lys Asp Lys Ser Thr Gly Lys Glu Gln
            435                 440                 445

Ser Ile Gln Ile Lys Ala Asn Ser Gly Leu Ser Asp Ala Glu Ile Glu
        450                 455                 460

Ala Met Ile Lys Asp Ala Glu Ala Asn Ala Glu Glu Asp Arg Lys Phe
465                 470                 475                 480

Glu Glu Leu Ala Lys Ala Arg Asn Gln Ala Asp Ala Leu Ile Ser Ser
                485                 490                 495

Ser Asn Lys Ala Val Lys Asp Leu Gly Asp Lys Val Thr Glu Asp Glu
            500                 505                 510

Lys Thr Ala Val Asn Thr Ala Val Ser Glu Leu Glu Ala Ala Thr Lys
        515                 520                 525

Glu Asn Asp Val Glu Ala Ile Lys Ala Lys Thr Glu Ala Leu Gln Asn
530                 535                 540

Ile Leu Met Pro Ile Thr Gln Arg Ala Tyr Glu Gln Ala Gln Gln Ala
545                 550                 555                 560

Gly Gly Ala Glu Gly Phe Asp Pro Asn Ala Phe Gln Gly Gly Asp Ala
                565                 570                 575

Gly Gln Gln Lys Ala Asp Asp Gly Val Val Asp Ala Glu Phe Thr Glu
            580                 585                 590

Val Lys Asp Asp Lys Lys
        595

<210> SEQ ID NO 25
<211> LENGTH: 663
<212> TYPE: PRT
<213> ORGANISM: Acinetobacter baumannii

<400> SEQUENCE: 25

Met Asp Trp Met Glu Gln Glu Gln Glu Arg Gly Ile Thr Ile Thr Ser
1               5                   10                  15

Ala Ala Thr Thr Cys Phe Trp Ser Gly Met Gly Asn Gln Phe Pro Gln
```

-continued

```
             20                  25                  30
His Arg Ile Asn Val Ile Asp Thr Pro Gly His Val Asp Phe Thr Ile
         35                  40                  45
Glu Val Glu Arg Ser Met Arg Val Leu Asp Gly Ala Cys Met Val Tyr
     50                  55                  60
Cys Ala Val Gly Gly Val Gln Pro Gln Ser Glu Thr Val Trp Arg Gln
 65                  70                  75                  80
Ala Asn Lys Tyr Lys Val Pro Arg Leu Ala Phe Val Asn Lys Met Asp
                 85                  90                  95
Arg Thr Gly Ala Asn Phe Phe Arg Val Val Glu Gln Met Lys Thr Arg
             100                 105                 110
Leu Gly Ala Asn Pro Val Pro Ile Val Val Pro Ile Gly Ala Glu Asp
         115                 120                 125
Thr Phe Thr Gly Val Val Asp Leu Ile Glu Met Lys Ala Ile Ile Trp
     130                 135                 140
Asp Glu Ala Ser Gln Gly Met Lys Phe Glu Tyr Gly Glu Ile Pro Ala
145                 150                 155                 160
Asp Leu Val Asp Thr Ala Gln Glu Trp Arg Thr Asn Met Val Glu Ala
                 165                 170                 175
Ala Ala Glu Ala Ser Glu Gly Leu Met Asp Lys Tyr Leu Glu Glu Gly
             180                 185                 190
Asp Leu Ser Lys Glu Asp Ile Ile Ala Gly Leu Arg Ala Arg Thr Leu
         195                 200                 205
Ala Ser Glu Ile Gln Val Met Leu Cys Gly Ser Ala Phe Lys Asn Lys
     210                 215                 220
Gly Val Gln Arg Met Leu Asp Ala Val Ile Glu Phe Leu Pro Ser Pro
225                 230                 235                 240
Thr Glu Val Lys Ala Ile Glu Gly Ile Leu Asp Asp Lys Asp Glu Thr
                 245                 250                 255
Lys Ala Ser Arg Glu Ala Ser Asp Glu Ala Pro Phe Ser Ala Leu Ala
             260                 265                 270
Phe Lys Ile Met Asn Asp Lys Phe Val Gly Asn Leu Thr Phe Val Arg
         275                 280                 285
Val Tyr Ser Gly Val Leu Lys Gln Gly Asp Ala Val Tyr Asn Pro Val
     290                 295                 300
Lys Ser Lys Arg Glu Arg Ile Gly Arg Ile Val Gln Met His Ala Asn
305                 310                 315                 320
Glu Arg Gln Asp Ile Asp Glu Ile Arg Ala Gly Asp Ile Ala Ala Cys
                 325                 330                 335
Val Gly Leu Lys Asp Val Thr Thr Gly Asp Thr Leu Cys Asp Glu Lys
             340                 345                 350
Asn Ile Ile Thr Leu Glu Arg Met Glu Phe Pro Asp Pro Val Ile Gln
         355                 360                 365
Leu Ala Val Glu Pro Lys Thr Lys Ala Asp Gln Glu Lys Met Ser Ile
     370                 375                 380
Ala Leu Gly Arg Leu Ala Lys Glu Asp Pro Ser Phe Arg Val His Thr
385                 390                 395                 400
Asp Glu Glu Ser Gly Gln Thr Ile Ile Ala Gly Met Gly Glu Leu His
                 405                 410                 415
Leu Asp Ile Ile Val Asp Arg Met Lys Arg Glu Phe Gly Val Glu Ala
             420                 425                 430
Asn Ile Gly Lys Pro Met Val Ala Tyr Arg Glu Thr Ile Lys Lys Thr
         435                 440                 445
```

Val Glu Gln Glu Gly Lys Phe Val Arg Gln Thr Gly Lys Gly Lys
    450                 455                 460

Phe Gly His Val Tyr Val Arg Leu Glu Pro Leu Asp Val Glu Ala Ala
465                 470                 475                 480

Gly Lys Glu Tyr Glu Phe Ala Glu Val Val Gly Val Val Pro
                485                 490                 495

Lys Glu Phe Phe Gly Ala Val Asp Lys Gly Ile Gln Glu Arg Met Lys
                500                 505                 510

Asn Gly Val Leu Ala Gly Tyr Pro Val Val Gly Val Lys Ala Val Leu
            515                 520                 525

Phe Asp Gly Ser Tyr His Asp Val Asp Ser Asp Glu Leu Ser Phe Lys
530                 535                 540

Met Ala Gly Ser Tyr Ala Phe Arg Asp Gly Phe Met Lys Ala Asp Pro
545                 550                 555                 560

Val Leu Leu Glu Pro Ile Met Lys Val Glu Val Glu Thr Pro Glu Asp
                565                 570                 575

Tyr Met Gly Asp Ile Met Gly Asp Leu Asn Arg Arg Arg Gly Met Val
                580                 585                 590

Gln Gly Met Asp Asp Leu Pro Gly Gly Thr Lys Ala Ile Lys Ala Glu
            595                 600                 605

Val Pro Leu Ala Glu Met Phe Gly Tyr Ala Thr Gln Met Arg Ser Met
610                 615                 620

Ser Gln Gly Arg Ala Thr Tyr Ser Met Glu Phe Ala Lys Tyr Ala Glu
625                 630                 635                 640

Thr Pro Arg Asn Val Ala Glu Gly Ile Ile Ala Lys Phe Gln Ala Gly
                645                 650                 655

Gly Lys Lys Gly Asp Asp Glu
    660

<210> SEQ ID NO 26
<211> LENGTH: 581
<212> TYPE: PRT
<213> ORGANISM: Acinetobacter baumannii

<400> SEQUENCE: 26

Met Asn Gln Glu Thr Gly Arg Gly Val Thr Arg Gly Thr Lys Leu Tyr
1               5                   10                  15

Val Lys Asp Val Pro Val Leu Ala Val Pro Tyr Phe Asn Phe Pro Ile
                20                  25                  30

Asp Asp Arg Arg Thr Thr Gly Ile Leu Asn Pro Gln Phe Gly Phe Ser
            35                  40                  45

Asn Asp Gly Gly Ile Glu Leu Ser Val Pro Val Tyr Leu Asn Leu Ala
        50                  55                  60

Pro Asn Tyr Asp Ala Thr Ile Thr Pro Arg Tyr Leu Ala Asp Arg Gly
65              70                  75                  80

Ala Met Leu Gln Gly Glu Phe Arg Tyr Leu Thr Asp Gly Phe Gly Ala
                85                  90                  95

Gly Gln Ile Trp Gly Gly Ile Leu Pro Ser Asp Lys Glu Tyr Asp Asp
            100                 105                 110

Lys Asp Arg Lys Asp Phe His Phe Leu His Asn Trp Asp Ile Asn Asp
        115                 120                 125

Gln Trp Ser Thr Asn Leu Glu Tyr Asn Tyr Ala Ser Asp Lys Asp Tyr
    130                 135                 140

Phe Ser Asp Leu Asp Ser Ser Pro Ile Ser Lys Thr Asp Leu Asn Leu

-continued

```
            145                 150                 155                 160
Arg Arg Ala Trp Glu Leu Asn Tyr Gln His Gly Ile Pro Gly Leu Lys
                165                 170                 175
Ala Gln Leu Lys Val Glu Asp Phe Gln Thr Leu Asp Pro Gln Val Lys
                180                 185                 190
Asp Ala Asp Lys Pro Tyr Ala Arg Leu Pro Gln Phe Leu Leu Asn Tyr
                195                 200                 205
Val Thr Gly Asn Pro Leu Gly Leu Gln Tyr Glu Phe Asn Asn Asp Thr
                210                 215                 220
Ala Tyr Phe Lys Lys Ser Ile Asn Asp Asn Ser Ala Gln Glu Ser Ser
225                 230                 235                 240
Gly Thr Arg Ile Tyr Asn Gln Phe Ala Thr Arg Tyr Asn Tyr Arg Thr
                245                 250                 255
Pro Ala Ala Phe Val Ile Pro Glu Val Ser Val Arg Ser Ile Gln Thr
                260                 265                 270
Phe Tyr Asp Lys Asp Thr Gln Leu Asn Asn Pro Gly Gly Ser Glu Asn
                275                 280                 285
Lys Ser Val Val Val Pro Gln Phe Thr Leu Asp Thr Gly Leu Asn Phe
                290                 295                 300
Glu Arg Glu Gly Lys Tyr Leu Gln Thr Leu Thr Pro Arg Ala Phe Tyr
305                 310                 315                 320
Ala Tyr Ala Pro Tyr Lys Asn Gln Asp Gly Tyr Pro Asn Phe Asp Ser
                325                 330                 335
Thr Thr Ala Ser Ile Ser Tyr Asp Gln Leu Phe Asn Pro Tyr Arg Phe
                340                 345                 350
Tyr Gly His Asp Arg Leu Glu Asp Asn Asn Phe Leu Ser Leu Gly Val
                355                 360                 365
Ser Tyr Ser Leu Phe Asp Thr Val Gly Leu Glu Arg Leu Arg Ala Ser
                370                 375                 380
Val Gly Gln Ser Tyr Tyr Phe Glu Asp Arg Arg Val Thr Leu Lys Gln
385                 390                 395                 400
Gly Gln Asp Glu Phe Asp Thr Glu Arg Lys Thr Gly Pro Val Ile Ser
                405                 410                 415
Leu Ser Ser Gln Leu Asn Gln Asn Phe Thr Ile Ala Ala Asn Ser Ala
                420                 425                 430
Trp Met Ser Asn Gly Asp Asn Ala Gln Arg Asp Phe Gln Val Tyr Tyr
                435                 440                 445
Thr Gly Asp Lys Gly Asn Leu Tyr Asn Leu Gly Tyr Phe Tyr Arg Lys
                450                 455                 460
Asp Ile Pro Gly Arg Gln Asp Thr Tyr Asp Gln Val Val Ala Ser Phe
465                 470                 475                 480
Ile Gln Pro Ile Lys Asp Asn Trp Arg Ile Met Gly His Val Gln Tyr
                485                 490                 495
Asp Met Asp Asn Asp Val Ala Arg Glu Leu Leu Leu Gly Val Asn Tyr
                500                 505                 510
Glu Ser Cys Cys Trp Gly Ile Ser Val Tyr Gly Arg Ser Tyr Tyr Asn
                515                 520                 525
Asp Leu Asp Asp Pro Lys Thr Ser Asp Val Ser Glu Lys Arg Ala Ile
                530                 535                 540
Met Ala Glu Ile Thr Leu Lys Gly Leu Gly Gly Leu Asn Asn Lys Leu
545                 550                 555                 560
Ala Ser Leu Leu Glu Asn Arg Phe Leu Gly Phe Asn Lys Ile Asn Gln
                565                 570                 575
```

<210> SEQ ID NO 27
<211> LENGTH: 208
<212> TYPE: PRT
<213> ORGANISM: Acinetobacter baumannii

<400> SEQUENCE: 27

Met Leu Asp Arg His Val Leu Arg Pro Val Ala Val Glu Tyr Arg Glu
1               5                   10                  15

Lys Thr Pro Glu Asp Val Arg Gly Ser Tyr Arg Gln Phe Arg Lys Asn
                20                  25                  30

Leu Gly Glu Pro Trp Asn Ala Val Asn Gln Leu Ile Gln Gly Arg Pro
            35                  40                  45

Gly Arg Ala Ala Lys Thr Leu Gly Arg Phe Thr Ile Asn Thr Leu Thr
        50                  55                  60

Thr Leu Gly Leu Ala Asp Pro Ala Ser Arg Leu Gly Leu Pro Pro Glu
65                  70                  75                  80

Glu Glu Ser Phe Gly Val Thr Leu Gly Tyr Tyr Gly Val Pro Ser Gly
                85                  90                  95

Pro Phe Leu Met Leu Pro Phe Phe Gly Pro Ser Thr Leu Arg Asp Gly
            100                 105                 110

Val Gly Leu Ala Val Asp Ala Gln Ala Arg Pro Gln Lys Tyr Ile Met
        115                 120                 125

Asp Asp Gln Asp Gly Leu Tyr Trp Ser Thr Asn Leu Leu Gln Ala Val
130                 135                 140

Asp Thr Arg Ala Gln Tyr Leu Asp Leu Asp Gln Thr Ile Gln Gly Asp
145                 150                 155                 160

Gln Tyr Ala Met Ile Arg Asp Leu Tyr Leu Gln Arg Lys Ala Phe Gln
                165                 170                 175

Ile Ala Glu Lys Lys Gly Asp Ser Ala Asp Val Ser Phe Ile Asp Asp
            180                 185                 190

Asp Glu Ser Glu Asp Val Pro Glu Asp Asn Thr Asp Lys Thr Glu Lys
        195                 200                 205

<210> SEQ ID NO 28
<211> LENGTH: 381
<212> TYPE: PRT
<213> ORGANISM: Acinetobacter baumannii

<400> SEQUENCE: 28

Met Leu Gly Asp Trp Asn Gly Gln Arg Thr Ala Leu Gln Ala Gln Gly
1               5                   10                  15

Tyr Asp Phe Ser Phe Gly Tyr Thr Gly Glu Tyr Ala Gly Ile Leu Asp
                20                  25                  30

Ser Lys Gln Thr Ser Thr His Gly Ser Ala Tyr Thr Gly Gln Leu Ala
            35                  40                  45

Leu Gly Ser His Leu Asp Leu Gly Lys Ile Leu Gly Trp Gln Asp Thr
        50                  55                  60

Glu Ala Gln Ile Thr Leu Thr Tyr Arg Asp Gly Gln Ser Leu Ser Glu
65                  70                  75                  80

His Ser Pro Ala Leu Ala Gly His Gln Ser Ser Val Gln Glu Val Trp
                85                  90                  95

Gly Arg Glu Gln Thr Trp Arg Leu Thr Asp Leu Trp Ile Lys Lys Lys
            100                 105                 110

Phe Leu Asp Gln Lys Leu Asp Val Lys Val Gly Arg Phe Gly Glu Gly
            115                 120                 125

Glu Asp Phe Asn Ser Phe Asp Cys Asp Phe Gln Asn Leu Ala Leu Cys
        130                 135                 140

Gly Ser Gln Val Gly Asn Trp Val Gly Asp Gln Trp Tyr Asn Trp Pro
145                 150                 155                 160

Val Ser Gln Trp Ala Met Arg Val Lys Tyr Asn Leu Gln Pro Asp Leu
                165                 170                 175

Tyr Thr Gln Val Gly Val Tyr Glu Tyr Asn Pro Glu Asn Leu Glu Arg
            180                 185                 190

Gly Lys Gly Phe Asn Leu Ser Thr Asp Gly Ser His Gly Ala Ile Ile
        195                 200                 205

Pro Ala Glu Val Val Trp Ser Pro Lys Leu Gly Val Gln Ser Met Pro
    210                 215                 220

Gly Glu Tyr Arg Leu Gly Tyr Tyr Ser Thr Ala Asp Ala Lys Glu
225                 230                 235                 240

Ile Ala Asp Ser Thr Lys Thr Ser His Lys Gln Gly Val Trp Val Thr
                245                 250                 255

Ala Lys Gln Lys Leu Phe Gln Pro Ala Asp Gln Thr Asp Arg Gly Leu
            260                 265                 270

Thr Gly Phe Val Asn Leu Thr Phe His Asp Ser Asp Thr Asn Lys Val
        275                 280                 285

Asp Asn Met Gln Asn Ile Gly Leu Val Tyr Lys Gly Leu Leu Asn Gln
    290                 295                 300

Arg Pro Gln Asp Glu Leu Ala Leu Gly Val Ala Arg Ile His Ile Asn
305                 310                 315                 320

Asp Asp Trp Ser Asp Val Gln Ala Lys Glu Tyr Asp Thr Glu Tyr Asn
                325                 330                 335

Thr Glu Leu Tyr Tyr Gly Ile His Ala Thr Asn Trp Leu Thr Ile Arg
            340                 345                 350

Pro Asn Val Gln Tyr Val Arg His Val Gly Ala Leu Lys Asn Gly Asp
        355                 360                 365

Asn Thr Trp Val Gly Gly Ile Lys Phe Ser Thr Ala Phe
    370                 375                 380

<210> SEQ ID NO 29
<211> LENGTH: 167
<212> TYPE: PRT
<213> ORGANISM: Acinetobacter baumannii

<400> SEQUENCE: 29

Met Asp Ser Met Gln Lys His Leu Leu Leu Pro Leu Phe Leu Ser Ile
1               5                   10                  15

Gly Leu Ile Leu Gln Gly Cys Asp Ser Lys Lys Val Ala Gln Ala Glu
            20                  25                  30

Pro Pro Pro Ala Lys Val Ser Val Leu Ser Ile Gln Pro Gln Ser Val
        35                  40                  45

Asn Phe Ser Glu Asn Leu Pro Ala Arg Val His Ala Phe Arg Thr Ala
    50                  55                  60

Glu Ile Arg Pro Gln Val Gly Gly Ile Ile Glu Lys Val Leu Phe Lys
65                  70                  75                  80

Gln Gly Ser Glu Val Arg Ala Gly Gln Ala Leu Tyr Lys Ile Asn Ser
                85                  90                  95

Glu Thr Phe Glu Ala Asp Val Asn Ser Asn Arg Ala Ser Leu Asn Lys

```
            100                 105                 110
Ala Glu Ala Glu Val Ala Arg Leu Lys Val Gln Leu Glu Arg Tyr Glu
            115                 120                 125

Gln Leu Leu Pro Ser Asn Ala Ile Ser Lys Gln Glu Val Ser Asn Ala
        130                 135                 140

Gln Ala Gln Tyr Arg Gln Ala Leu Ala Asp Val Ala Gln Met Lys Ala
145                 150                 155                 160

Leu Leu Ala Arg Gln Asn Leu
                165

<210> SEQ ID NO 30
<211> LENGTH: 385
<212> TYPE: PRT
<213> ORGANISM: Acinetobacter baumannii

<400> SEQUENCE: 30

Met Ala Thr Ala Arg Asn Arg Gly Met Asn Lys Gly Lys Ile Val Ser
1               5                   10                  15

Leu Asp Lys Val Ile Ala Ala Ile Lys Asn Ala Val Ala Glu Ala Glu
                20                  25                  30

Asn Met Ala Glu Cys Arg Ile His Ser Ala Trp Val Ser Ile Pro Ser
            35                  40                  45

Thr Glu Leu Gln Ser Phe Tyr Ala Ser Gly Arg Thr Pro Val Ala Asn
        50                  55                  60

Pro Ala His Val Ile Thr Thr Asn Glu Val Val Arg Ala Leu Glu Leu
65                  70                  75                  80

Ala Lys Ala Ser His Val Thr Ser Asp Tyr Tyr Leu Ala Ser Ala Val
                85                  90                  95

Pro Leu Gly Phe Glu Leu Gly Asp Ser Ser Glu Trp Val Gln Asn Pro
            100                 105                 110

Ile Asn Met Thr Ala His Ser Met Thr Gly His Tyr Gln Leu Met Met
        115                 120                 125

Met Pro Ile Ala Thr Met Gln Asn Leu Asp Arg Ala Met Lys Gly Ala
130                 135                 140

Asn Ile Gly Val Glu Lys Met Val Val Ser Cys Leu Ala Thr Ala Glu
145                 150                 155                 160

Ala Ser Leu Leu Lys Asp Glu Lys Glu Tyr Gly Val Cys Leu Val Asp
                165                 170                 175

Ile Gly Ala Gly Ile Thr Asn Leu Ala Val Tyr Leu Asp Gly Arg Leu
            180                 185                 190

Ala Leu Ala Arg Thr Leu Gln Arg Gly Gly Glu His Val Thr Arg Asp
        195                 200                 205

Ile Ala Ala Val Leu Gln Thr Thr Thr Glu Gly Ala Glu Arg Ile Lys
        210                 215                 220

Ile Leu His Gly Cys Val Asp Leu Ser Ala Val Lys Pro Asp His Met
225                 230                 235                 240

Ile Gln Val Gln Gly Ile Asp Gly Pro Gln Thr Ile Ser Arg Ile Glu
                245                 250                 255

Leu Ala Glu Ile Ile Ile Ala Arg Tyr Glu Glu Ile Phe Ser Gln Ile
            260                 265                 270

Arg Glu Glu Leu Glu Gln Ser Gly Ala Ile His Gly Leu Tyr His Gly
        275                 280                 285

Val Val Leu Thr Gly Asp Ala Cys Gln Ile Glu Gly Met Val Ser Leu
    290                 295                 300
```

```
Ala Arg Arg Met Leu Gly Val Ser Ala His Leu Gly Asn Pro Pro Leu
305                 310                 315                 320

Gln Val Tyr Ala Asp Asp Gln His Gln Ala Ala Leu Arg Arg Ser Met
            325                 330                 335

Tyr Ala Thr Ala Ala Gly Leu Leu Met Phe Ser Gln Ser Glu Leu Gln
        340                 345                 350

Glu Ala Val Glu Glu Pro Glu Glu Gly Asn Asp Arg Ser Val Trp Glu
    355                 360                 365

Arg Met Val Asn Gly Trp Asn Ala Phe Asn Ser Lys Leu Lys Ala Ile
    370                 375                 380

Phe
385

<210> SEQ ID NO 31
<211> LENGTH: 356
<212> TYPE: PRT
<213> ORGANISM: Acinetobacter baumannii

<400> SEQUENCE: 31

Met Val Gln Ser Asp Ile Gln Gly Val Lys Phe Val Cys Ala Asn Thr
1               5                   10                  15

Asp Lys Gln Ala Leu Asp Cys Met Asn Ala Pro Phe Lys Ile Gln Leu
            20                  25                  30

Gly Glu Gln Ser Thr Arg Gly Leu Gly Ala Gly Ala Asn Pro Glu Val
        35                  40                  45

Gly Gln Val Ala Ala Glu Glu Ser Arg Glu Ile Ile Arg Gln His Leu
    50                  55                  60

Glu Gly Thr Asp Met Val Phe Val Thr Ala Gly Met Gly Gly Gly Thr
65                  70                  75                  80

Gly Thr Gly Ala Ala Pro Val Val Ala Glu Val Ala Lys Glu Met Gly
                85                  90                  95

Ile Leu Thr Val Gly Val Val Thr Thr Pro Phe Asn Phe Glu Gly Arg
            100                 105                 110

Arg Arg Gln Lys Ser Ala Glu Arg Gly Ile Glu Ala Leu Glu Ala His
        115                 120                 125

Val Asp Ser Leu Ile Ile Ile Pro Asn Gln Arg Leu Leu Ser Val Tyr
    130                 135                 140

Gly Asp Ile Ser Met Lys Asp Ala Tyr Lys Lys Ala Asp Asp Val Leu
145                 150                 155                 160

Leu Asn Ala Val Arg Ser Ile Phe Asp Leu Val Val Asn Arg Gly His
                165                 170                 175

Ile Asn Leu Asp Phe Ala Asp Leu Lys Thr Ala Met Ser Thr Arg Gly
            180                 185                 190

Tyr Ala Met Met Gly Ala Gly Leu Gly Arg Gly Glu Asp Arg Ala Arg
        195                 200                 205

Gln Ala Ala Glu Gln Ala Ile Arg Ser Pro Leu Leu Asp Asn Val Asn
    210                 215                 220

Ile Ile Asn Ala Lys Gly Val Leu Ile Asn Ile Thr Gly Gly Asp Asp
225                 230                 235                 240

Ile Thr Leu Arg Glu Thr Glu Ile Ile Thr Asp Val Val Asn Gln Ile
                245                 250                 255

Val Asp Leu Asp Glu Gly Glu Ile Phe Tyr Gly Thr Val Phe Asp Pro
            260                 265                 270

Asp Ala Arg Asp Glu Leu Arg Val Thr Val Ile Ala Thr Gly Leu Thr
        275                 280                 285
```

-continued

```
Arg Asn Ala Ala Asp Ala Glu Pro Arg Lys Arg Asn Thr Val Ser His
    290             295                 300

Thr Ser Thr Gln Ser Ala Gln Ser Val Asp Glu Asp Asp Val Pro Ala
305             310                 315                 320

Ile Asn Lys Arg Gln Asn Ala Glu Asn Asp Val Asn Asn Ala Pro Ser
            325                 330                 335

Ser Thr Pro Arg Ser Ser Pro Met Ser Ile Gln Asp Tyr Leu Lys Asn
            340             345                 350

Gln Gln Arg Lys
        355
```

HYR1-DERIVED COMPOSITIONS AND METHODS OF TREATMENT USING SAME

STATEMENT AS TO FEDERALLY FUNDED RESEARCH

This invention was made with government support under Public Health Service grants R01 AI19990, R01 AI063382, R01 AI063503, R03 AI083251, and R21 AI082414. The United States Government has certain rights in this invention.

FIELD OF THE INVENTION

The present invention relates generally to compositions and methods for detecting, treating and preventing infectious diseases in a subject.

BACKGROUND OF THE INVENTION

*Candida* species, the third most common cause of healthcare-associated bloodstream infections, causes approximately 60,000 cases of hematogenously disseminated candidiasis per year in the United States, resulting in billions of dollars of healthcare expenditures. Despite current antifungal therapy, mortality remains unacceptably high. Because of the rising incidence of life-threatening candidiasis and high treatment failure rates, more effective prophylactic and therapeutic strategies are needed.

The primary host defense mechanism against disseminated candidiasis is phagocytic killing of the organism. Only phagocytic cells are capable of directly killing *Candida* in vitro. Additionally, within thirty-minutes of intravenous inoculation of *Candida* in mice, rabbits, dogs, or humans, yeasts are retained within the reticuloendothelial system, especially in the liver. The liver, rich in Kupffer macrophages, is capable of clearing 99.9% of yeast in the portal system during a single pass, underscoring the effectiveness of phagocytic defense mechanisms against the fungus. Hence, resistance of *C. albicans* to phagocyte killing is an important virulence function of the organism.

Cell surface glycosyl phosphatidylinositol (GPI)-anchored proteins are at the critical interface between pathogen and host, making these proteins likely participants in host-pathogen interactions.

The identification of effectors in the regulatory pathways of the organism that contribute to virulence offers the opportunity for therapeutic intervention with methods or compositions that are superior to existing antifungal agents. The identification of cell surface proteins or hyphal proteins that affect a regulatory pathway involved in virulence is particularly promising because characterization of the protein enables immunotherapeutic techniques that are likely superior to or synergistic with existing antifungal agents when fighting a candidal infection.

The virulence of *C. albicans* is regulated by several putative virulence factors of which adherence to host constituents and the ability to transform from yeast-to-hyphae are among the most critical in determining pathogenicity. While potent antifungal agents exist that are microbicidal for *Candida*, the attributable mortality of candidemia is approximately 38%, even with treatment with potent antifungal agents such as amphotericin B. Also, existing agents such as amphotericin B tend to exhibit undesirable toxicity. Although additional antifungals may be developed that are less toxic than amphotericin B, it is unlikely that agents will be developed that are more potent. Therefore, either passive or active immunotherapy to treat or prevent disseminated candidiasis is a promising alternative to standard antifungal therapy.

Lethal infections of antibiotic resistant pathogenic bacteria, like infections resulting from *Candida*, are becoming increasingly frequent. Moreover, the risk of contracting these lethal infections is extremely high for many at-risk patients in intensive care units (ICUs) every year as well as for soldiers deployed to front line combat zones. *Acinetobacter* species are a frequent source of infection in hospitalized patients and soldiers, in particular the species *Acinetobacter baumannii*. *Acinetobacter* is a genus of gram negative bacteria belonging to the Gammaproteobacteria. *Acinetobacter* species contribute to the mineralization of aromatic compounds in the soil. Unfortunately, no technology presently exists that prevents *Acinetobacter* infections, aside from standard hand washing and other infection control practices in hospital settings.

Active and passive immunization of individuals against antibiotic resistant pathogenic bacteria presents a convenient and potentially cost effective method of trying to combat these infections. However, identifying and developing effective antigenic targets for implementation of passive and active immunizations against bacteria in general presents a difficult challenge because of the vast array of bacterial species. The identification of compounds that affect the virulence of specific bacterial families or genera provides an opportunity to develop novel therapeutic interventions. In particular, the recognition of ubiquitous cell surface proteins that are present on the bacterial families or genera that can be identified by an individual's immune system will enable immunotherapeutic techniques. These techniques will likely be superior to and also can act in synergy with antibiotics to prevent or treat bacterial infections.

There accordingly exists a need for compounds and methods that reduce the risk of infectious diseases related to *Candida* and bacterial infections and provide effective therapies. The present invention satisfies this need and provides related advantages as well.

SUMMARY OF THE INVENTION

It has been discovered that fragments of the *Candida* cell surface protein Hyr1 are useful in immunizing a subject against *Candida* infections. It has also been found that Hyr1 protein combats *Acinetobacter* infections as well.

Accordingly, in a first aspect, the invention features an isolated polypeptide including the amino acid sequence of any one of SEQ ID NOs: 3-10, or a variant sequence thereof having up to three substitutions, deletions, or additions to the amino acid sequence of any one of SEQ ID NOs: 3-10, wherein the polypeptide does not include more than 20 contiguous amino acids of SEQ ID NO: 2. In some embodiments, the polypeptide includes the amino acid sequence of any one of SEQ ID NOs: 3-10. In some embodiments, the polypeptide consists of between 14 and 20 amino acids. In some embodiments, the N-terminal amino acid residue or C-terminal amino acid residue of the polypeptide is cysteine. In other embodiments, the amino acid sequence of the polypeptide includes or consists of the amino acid sequence of any one of SEQ ID NOs: 11-18.

In a second aspect, the invention features an isolated conjugate including a polypeptide of the first aspect conjugated to a carrier. For example, the carrier may be keyhole limpet hemocyanin (KLH), CRM197, or tetanus toxoid, or may be a phage, a yeast, a virus, virosome, or a recombinant virus-like particle. In some embodiments, the conjugate is a recombinant fusion protein.

In a third aspect, the invention features a vaccine including an immunogenic amount of a polypeptide of the first aspect or a conjugate of the second aspect, and a pharmaceutically acceptable excipient. In some embodiments, the vaccine includes a mixture of distinct polypeptides of the first aspect or conjugates of the second aspect. In some embodiments, the vaccine further includes an adjuvant, e.g., Alhydrogel. In some embodiments, a polypeptide of the first aspect or conjugate of the second aspect is produced synthetically or recombinantly. In some embodiments, the vaccine is for use in the vaccination of a mammal, e.g., a human, against candidiasis or vaccinating a mammal against *Acinetobacter*. In some embodiments, the vaccine is to be administered by intramuscular, subcutaneous, or intradermal administration. In some embodiments, the vaccination further includes administering a booster dose. In some embodiments, the candidiasis is disseminated candidiasis, e.g., hematogenously disseminated candidiasis, or the candidiasis is mucosal candidiasis, or the candidiasis is vagina candidiasis, or the candidiasis is caused by *Candida* such a *Candida albicans, Candida glabrata, Candida krusei, Candida parapsilosis*, or *Candida tropicalis*.

In a fourth aspect, the invention features a method of vaccinating a mammal, e.g., a human, against candidiasis including administering to the mammal the vaccine of the third aspect, thereby vaccinating the mammal against candidiasis or vaccinating the mammal against *Acinetobacter*. In some embodiments, the vaccine is administered by intramuscular, subcutaneous, or intradermal administration. In some embodiments, the administering further includes administering a booster dose. In some embodiments, the candidiasis is disseminated candidiasis, e.g., hematogenously disseminated candidiasis, or the candidiasis is mucosal or vaginal candidiasis, or the candidiasis is caused by *Candida* such as *Candida albicans, Candida glabrata, Candida krusei, Candida parapsilosis*, or *Candida tropicalis*.

In a fifth aspect, the invention features a method of producing a chimeric vaccine including the steps of: (a) providing a phage, yeast, or virus; (b) inserting into the phage, yeast, or virus a nucleic acid molecule that encodes a polypeptide of the first aspect; (c) allowing expression of the polypeptide in the phage, yeast, or virus; (d) isolating the phage, yeast, or virus of step (c) including the expressed polypeptide; and (e) adding a pharmaceutically acceptable excipient to the isolated phage, yeast, or virus of step (d). In some embodiments, the polypeptide is displayed on the surface of the phage, yeast, or virus following step (c).

In a sixth aspect, the invention features an isolated monoclonal antibody that binds to a polypeptide of the first aspect or a conjugate of the second aspect. In some embodiments, the antibody is human or humanized, or is chimeric. In some embodiments, the antibody is produced recombinantly or is chemically synthesized.

In a seventh aspect, the invention features a diagnostic composition including an antibody of the sixth aspect.

In an eighth aspect, the invention features a pharmaceutical composition including an antibody of the sixth aspect and a pharmaceutically acceptable excipient. In some embodiments, the pharmaceutical composition includes a mixture of antibodies of the sixth aspect with a plurality of distinct specificities.

In a ninth aspect, the invention features a pharmaceutical composition including polyclonal antibodies that bind to a polypeptide of the first aspect or a conjugate of the second aspect, or that bind to a mixture of distinct polypeptides of the first aspect or conjugates of the second aspect.

In some embodiments of the eighth or ninth aspect, the pharmaceutical composition is for use in the passive immunization of a mammal, e.g., a human, against candidiasis or a human, against *Acinetobacter*. For example, the pharmaceutical composition may be administered by intramuscular, subcutaneous, or intradermal administration. In some embodiments, the candidiasis is disseminated candidiasis, e.g., hematogenously disseminated candidiasis, or the candidiasis is mucosal such as vaginal candidiasis, or the candidiasis is caused by *Candida* such as *Candida albicans, Candida glabrata, Candida krusei, Candida parapsilosis*, or *Candida tropicalis*.

In a tenth aspect, the invention features a method of passive immunization of a mammal, e.g., a human, against candidiasis including administering to the mammal an effective amount of a pharmaceutical composition of the eighth or ninth aspect, thereby passively immunizing the mammal against the candidiasis or against *Acinetobacter*. In some embodiments, the pharmaceutical composition is administered by intramuscular, subcutaneous, or intradermal administration or even intranasally. In some embodiments, the candidiasis is disseminated candidiasis, e.g., hematogenously disseminated candidiasis, or the candidiasis is mucosal candidiasis such as vaginal candidiasis, or the candidiasis is caused by *Candida* such as *Candida albicans, Candida glabrata, Candida krusei, Candida parapsilosis*, or *Candida tropicalis*.

In still other aspects, the invention features compositions and methods as disclosed herein that are based, at least in part, on the identification that an immune response, such as antibodies and other mechanisms, that target the *Candida* HYR1 polypeptide and confer protection from *Acinetobacter* infection such as *Acinetobacter baumannii*. Active or passive immunization approaches using the HYR1 polypeptide or specific *Acinetobacter baumannii* proteins disclosed herein are useful to protect against infections caused by gram negative rod bacteria, including, but not limited to, *Acinetobacter baumannii*. Some uses of the compositions and methods disclosed herein include passive vaccination of acutely at-risk patients with a dose of anti-HYR1 antibody to prevent the acquisition of *Acinetobacter baumannii* infection. Additionally, patients with active *Acinetobacter baumannii* infection can be treated with the antibody alone or combined with other antibacterial agents. Alternatively, patients who are at risk of developing such infections, such as, for example, military personnel, can be actively vaccinated with a HYR1 polypeptides or specific *Acinetobacter baumannii* polypeptides disclosed herein to prevent such infections.

In other aspects, the invention, in this context, features passive or active vaccination as disclosed herein having the ability to markedly reduce the acquisition of drug-resistant, lethal *Acinetobacter baumannii* infection. Because there presently are no antibiotics with activity against the *Acinetobacter* genus, prevention of such infections is of paramount concern. Additionally, the vaccine and pharmaceutical compositions disclosed herein have potential to work against other infections caused by gram negative rods because the passive and active strategies provided by the invention are raised against a xeno-antigen from *Candida albicans* that has considerable structural homology to gram negative rod antigens including those from *Acinetobacter baumannii* origin. The use of a non-*Acinetobacter* antigen to protect against *Acinetobacter* infection provides a major advantage to combat infection.

The invention therefore provides an active vaccination useful to prevent infections in hospitalized patients using a HYR1 polypeptide or fragment thereof or *Acinetobacter baumannii* proteins disclosed herein. The invention also provides methods and compositions for active vaccination to prevent *Acinetobacter* infection in military personnel, which is highly desirable since *Acinetobacter* is one of the most common causes of combat wound infections. The invention still further provides methods and compositions for passive immunization as an adjunct therapy for active infection using an antibody, either polyclonal or monoclonal, raised against an HYR1 polypeptide or *Acinetobacter baumannii* proteins disclosed herein. Still further, the invention provides a diagnostic biomarker, by antibody or PCR detection, to determine the presence of *Acinetobacter* in infected fluids or tissues. The invention also provides that the above applications can extended to other medically important gram negative bacteria.

In other aspects, the invention relates to nucleic acids that encode specific HYR1 polypeptides or fragments thereof that can act as antigens for generating an immune response to gram negative bacteria, including bacteria of the *Acinetobacter* genus, for example, *Acinetobacter baumannii*.

For example, in some aspects of the invention, the nucleic acids of the invention encode an HYR1 polypeptide comprising an amino acid sequence selected from one of more of SEQ ID NOS:3-10 or from one or more of CGPSAPES-ESDLNTP (SEQ ID NO: 11), CGNRDHFRFEYYPDT (SEQ ID NO: 12), CGYDSKLFRIVNSRG (SEQ ID NO: 13), CKIKGTGCVTADEDT (SEQ ID NO: 14), CLKNAV-TYDGPVPNN (SEQ ID NO: 15), NSKSSTSFSNFDIGC (SEQ ID NO: 16), CEPTHNFYLKDSKSS (SEQ ID NO: 17), and TSRIDRGGIQGFHGC (SEQ ID NO: 18). Moreover, in some aspects of the invention, the HYR1 polypeptide can comprise less than 937, 936, 935, 934, 933, 932, 931, 930, 920, 910, 900, 890, 880, 870, 860, 850, 840, 830, 820, 810, 800, 790, 780, 770, 760, 750, 740, 730, 720, 710, 700, 690, 680, 670, 660, 650, 640, 630, 620, 610, 600, 590, 580, 570, 560, 550, 540, 530, 520, 510, 500, 490, 480, 470, 460, 450, 440, 430, 420, 410, 400, 390, 380, 370, 360, 350, 340, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30 or 20 amino acid residues in length and can be immunogenic. In some aspects of the invention, the nucleic acids of the invention do not encode the HYR1 polypeptide of SEQ ID NOS: 1 or 2. Still in other aspects, nucleic acids encode any one of SEQ ID NOS:3-10 or 11-18 alone or in combination.

The invention also provides embodiments wherein the nucleic acid sequence encodes more than one amino acid sequence set forth in any one of SEQ ID NOS: 3-10 or SEQ ID NOS: 11-18 alone or in combination. For example, a nucleic acid sequence of the invention can encode two amino acid sequences such as SEQ ID NO: 15 in combination with SEQ ID NO: 12, or alternatively SEQ ID NO: 11 in combination with SEQ ID NO: 17, or alternatively SEQ ID NO: 13 in combination with SEQ ID NO: 18. It is understood that the nucleic acids of the invention can encode two, three, four, five, six, seven or all eight amino acid sequence selected from SEQ ID NOS: 11-18. It is also understood that the encoded amino acid sequence need not be contiguous and can be linked by intervening spacer sequences, which can, for example, allow for the expressed polypeptide to present the desired amino acid sequence or epitope for generating an immune response.

In some aspects of the invention, the amino acid sequence encoded by the nucleic acids of the invention comprises substantially the same amino acid sequence set forth in any one of SEQ ID NOS: 3-10 or SEQ ID NOS: 11-18. For example, the amino acid sequence can have at least 65%, 70%, 75%, 80%, 85%, 90%, 95%, 98% or 99% sequence identity to any one of SEQ ID NOS: 3-10 or 11-18, wherein the polypeptide can be bound by an anti-HYR1 antibody disclosed herein. In other aspects, the HYR1 polypeptide expressed by the nucleic acids of the invention can be immunogenic and capable of eliciting production of an anti-HYR1 antibody or immunogenic response in a subject.

When incorporated into a variety of protein expression systems known to those of skill in the art, the nucleic acid molecules described herein are useful for producing polypeptide(s) of the invention. In addition, such nucleic acid molecules or fragments thereof can be labeled with a readily detectable substituent and used as hybridization probes for assaying for the presence and/or amount of a gram negative bacteria such as, for example, *Acinetobacter baumannii* in a given sample. The nucleic acid molecules described herein, and fragments thereof, are also useful as primers and/or templates in a PCR reaction for amplifying nucleic acids encoding invention polypeptides or proteins described herein.

The invention also provides vectors containing the nucleic acids of the invention. Suitable expression vectors are well-known in the art and include vectors capable of expressing a nucleic acid operatively linked to a regulatory sequence or element such as a promoter region or enhancer region that is capable of regulating expression of the nucleic acid. Appropriate expression vectors include vectors that are replicable in eukaryotic cells and/or prokaryotic cells and vectors that remain episomal or integrate into the host cell genome.

In other aspects, the invention additionally provides an isolated anti-*Acinetobacter* protein antibody. An "anti-*Acinetobacter* protein antibody" recognizes at least one protein, or fragment thereof, that naturally occurs in *Acinetobacter baumannii*. An anti-HYR1 antibody of the invention, which has specific reactivity to an HYR1 polypeptide disclosed herein, is one example of an anti-*Acinetobacter* protein antibody. As disclosed herein, specific *Acinetobacter baumannii* proteins have been identified that bind to antibodies raised against a HYR1 polypeptide having the amino acid sequence of SEQ ID NO: 15. These *Acinetobacter baumannii* proteins include an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii*. The anti-*Acinetobacter* protein antibody of the invention can be a monoclonal antibody or a polyclonal antibody. The invention further provides cell lines producing monoclonal antibodies having specific reactivity with a HYR1 polypeptide fragment disclosed herein, an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter*

*baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii*.

In other aspects, the invention further provides a method of diagnosing *Acinetobacter* infection in a subject. These methods can include the steps of: (a) providing a test sample from the subject; (b) contacting the sample with an agent that can bind an isolated nucleic acid that encodes an *Acinetobacter* protein disclosed herein or an *Acinetobacter* protein disclosed herein under suitable conditions; and (c) comparing the amount of the specific binding in the test sample with the amount of specific binding in a control sample, wherein an increased or decreased amount of the specific binding in the test sample as compared to the control sample is diagnostic of *Acinetobacter* infection. The conditions used in the methods of the invention are understood to allow specific binding of the agent to the nucleic acid or protein.

As described herein, *Acinetobacter* proteins encoded by the isolated nucleic acids of the method include an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii*.

Agents that can be used in the methods of the invention include an anti-*Acinetobacter* protein antibody as disclosed herein or an oligonucleotide comprising between 15 to 300 contiguous nucleotides that encode an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii*.

The invention additionally provides oligonucleotides comprising between 15 and 300 contiguous nucleotides that encode a portion of an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii*. As used herein, the term "oligonucleotide" refers to a nucleic acid molecule that includes at least 15 contiguous nucleotides from a reference nucleotide sequence, and can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, up to 350 contiguous nucleotides from the reference nucleotide sequence. The reference nucleotide sequence can be the sense strand or the anti-sense strand.

The isolated nucleic acid molecules of the invention can be used in a variety of diagnostic and therapeutic applications. For example, the isolated nucleic acid molecules of the invention can be used as probes and primers. The invention thus provides methods for detecting nucleic acid in a sample. The methods of detecting nucleic acid in a sample can be either qualitative or quantitative, as desired. For example, the presence, abundance, integrity or structure of a can be determined, as desired, depending on the assay format and the probe used for hybridization or primer pair chosen for application.

Accordingly, in some embodiments, the invention provides a method of detecting *Acinetobacter* nucleic acid molecules in a sample, comprising contacting the sample with two or more oligonucleotides comprising between 15 to 300 contiguous nucleotides that encode a portion of an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii*, amplifying a nucleic acid molecule, and detecting said amplification. In some aspects of the invention, the amplification is performed using polymerase chain reaction. Thus, in some aspects, the invention provides a kit for detecting the presence of *Acinetobacter* in a sample comprising at least one oligonucleotide comprising between 15 to 300 contiguous nucleotides that encode a portion of an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii*.

In some embodiments of the invention, a kit is also provided for detecting the presence of *Acinetobacter* in a sample comprising an isolated anti-*Acinetobacter* protein antibody as disclosed herein.

Thus, in accordance with embodiments of the present invention, diagnostic systems, in kit form, are provided comprising at least one invention nucleic acid or antibody in a suitable packaging material. The diagnostic kits containing nucleic acids are derived from the encoding nucleic acids described herein. In one embodiment, for example, the diagnostic nucleic acids are derived from any portion of a nucleic acid sequence encoding of an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii*, or any one of the oligonucleotides of the invention. Invention diagnostic systems are useful for assaying for the presence or absence of nucleic acid in either genomic DNA or mRNA.

A suitable diagnostic system includes at least one invention nucleic acid or antibody, and a separately packaged chemical reagent(s) in an amount sufficient for at least one assay. For a diagnostic kit containing nucleic acids of the invention, the kit will generally contain two or more nucleic acids. When the diagnostic kit is to be used in PCR, the kit will contain at least two oligonucleotides that can serve as primers for PCR. Those of skill in the art can readily incorporate invention nucleic probes and/or primers or invention antibodies into kit form in combination with appropriate buffers and solutions for the practice of the invention methods as described herein. A kit containing an antibody can contain a reaction cocktail that provides the proper conditions for performing an assay, for example, an ELISA or other immunoassay, for determining the level of expression of a polypeptide in a sample, and can contain control samples that contain known amounts of the polypeptide and, if desired, a second antibody specific for the antibody.

The contents of the kit of the invention, for example, nucleic acids or antibodies, are contained in packaging material, preferably to provide a sterile, contaminant-free environment. In addition, the packaging material contains instructions indicating how the materials within the kit can be employed both to detect the presence or absence of a particular sequence or protein or to diagnose the presence of, or a predisposition for a condition associated with bacterial infection. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

By "adjuvant" is meant one or more substances that cause stimulation of the immune system. In this context, an adjuvant is used to enhance an immune response to one or more vaccine antigens or antibodies. An adjuvant may be administered to a subject before, in combination with, or after administration of the vaccine or antibody. Examples of chemical compounds used as adjuvants include, but are not limited to, aluminum compounds (e.g., alum, Alhydrogel), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors. Other exemplary adjuvants include, for example, Freud's complete adjuvant, Freud's incomplete adjuvant, aluminum adjuvants, MF59, QS21 an immune modulating adjuvant such as a toxin, a cytokine, and a mycobacterial derivative; an oil formulation, a polymer, a micelle forming adjuvant, a saponin, an immunostimulating complex matrix (ISCOM® matrix), a particle, DDA (dimethyldioctadecylammonium bromide, DNA adjuvants, and an encapsulating adjuvant. Liposome formulations are also known to confer adjuvant effects, and therefore liposome adjuvants are included according to the invention. Adjuvants can facilitate uptake of the vaccine molecules by antigen presenting cells (APCs), such as dendritic cells, and activate these cells. An adjuvant's ability to increase an immune response is manifested by an increase in immune mediated protection. Enhancement of humoral immunity can be determined by, for example, an increase in the titer of antibody raised to the antigen. Enhancement of cellular immunity can be measured by, for example, a positive skin test, cytotoxic T-cell assay, ELISPOT assay for IFN-gamma or IL-2.

By "antibody" is meant whole antibodies, immunoglobulins, or any antigen-binding fragment or single chains thereof. Antibodies, as used herein, can be mammalian (e.g., human or mouse), humanized, chimeric, recombinant, synthetically produced, or naturally isolated, and can be, e.g., monoclonal or polyclonal. In most mammals, including humans, whole antibodies have at least two heavy (H) chains and two light (L) chains connected by disulfide bonds. Each heavy chain consists of a heavy chain variable region (abbreviated herein as $V_H$) and a heavy chain constant region. The heavy chain constant region consists of three domains, $C_H1$, $C_H2$, and $C_H3$ and a hinge region between $C_H1$ and $C_H2$. Each light chain consists of a light chain variable region (abbreviated herein as $V_L$) and a light chain constant region. The light chain constant region consists of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies of the present invention include all known forms of antibodies and other protein scaffolds with antibody-like properties. For example, the antibody can be a human antibody, a humanized antibody, a bispecific antibody, a chimeric antibody, or a protein scaffold with antibody-like properties, such as fibronectin or ankyrin repeats. The antibody also can be a Fab, Fab'2, scFv, SMIP, diabody, nanobody, aptamers, or a domain antibody. The antibody can have any of the following isotypes: IgG (e.g., IgG1, IgG2, IgG3, and IgG4), IgM, IgA (e.g., IgA1, IgA2, and IgAsec), IgD, or IgE.

The term "antibody fragment," as used herein, refers to one or more fragments of an antibody that retain the ability to specifically bind to an antigen. The antigen-binding function of an antibody can be performed by fragments of a full-length antibody, which include but are not limited to: (i) a Fab fragment, a monovalent fragment consisting of the $V_L$, $V_H$, $C_L$, and $C_H1$ domains; (ii) a $F(ab')_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., *Nature* 341:544-546 (1989)), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., *Science* 242:423-426 (1988) and Huston et al., *Proc. Natl. Acad. Sci. USA* 85:5879-5883 (1988)). These antibody fragments are obtained using conventional techniques known to those with skill in the art, and the fragments are screened for utility in the same manner as are intact antibodies. Antibody fragments can be produced by recombinant DNA techniques, or by enzymatic or chemical cleavage of intact immunoglobulins.

By "antigen" is meant a molecule to which an antibody can selectively bind. The target antigen may be a protein (e.g., an antigenic peptide), carbohydrate, nucleic acid, lipid, hapten, or other naturally occurring or synthetic compound. The target antigen may be a polypeptide or peptide mimic. An antigen may also be administered to an animal to generate an immune response in the animal.

By "carrier" in the context of a conjugate is meant a moiety or particle, e.g., KLH, CRM197, tetanus toxoid, a phage, a yeast, a virus, a virosome, or a recombinant virus-like particle, that is suitable for being linked to or displaying a polypeptide as described herein.

By "chimeric antibody" is meant an immunoglobulin or antibody whose variable regions derive from a first species and whose constant regions derive from a second species. Chimeric antibodies can be constructed, for example, by genetic engineering, from immunoglobulin gene segments belonging to different species (e.g., from a mouse and a human).

By "chimeric vaccine" is meant a vaccine that includes at least two distinct antigens, e.g., joined covalently. An example of a chimeric vaccine is a composition that includes a polypeptide displayed, e.g., on the surface of a particle such as a phage, virus, yeast, virosome, or recombinant virus-like particle.

By "conjugate" is meant a compound that includes a polypeptide of the invention linked to another moiety or particle, e.g., KLH, CRM197, tetanus toxoid, a phage, a yeast, a virus, a virosome, or a recombinant virus-like particle.

By "conservative substitution" in an amino acid sequence is meant replacement of an amino acid for another within a family of amino acids that are related in the chemical nature of their side chains.

Genetically encoded amino acids can be divided into four families: acidic (aspartate, glutamate); basic (lysine, arginine, histidine); nonpolar (alanine, valine, leucine, isoleucine, proline, phenylalanine, methionine, tryptophan); and uncharged polar (glycine, asparagine, glutamine, cysteine, serine, threonine, tyrosine). Phenylalanine, tryptophan, and tyrosine are sometimes grouped as aromatic amino acids. In similar fashion, the amino acids can also be separated into the following groups: acidic (aspartate, glutamate); basic (lysine, arginine, histidine); alipathic (glycine, alanine, valine, leucine, isoleucine, serine, threonine), with serine and threonine optionally grouped separately as alipathic-hydroxyl; aromatic (phenylalanine, tyrosine, tryptophan); amide (asparagine, glutamine); and sulfur-containing (cysteine, methionine).

Whether a change in the amino acid sequence results in a functional variant can be determined by assessing the ability of the variant polypeptide to function in a fashion similar to the wild-type polypeptide using standard methods such as those described herein.

By "diagnostic composition" is meant a composition containing a polypeptide, conjugate, vaccine, or antibody of the invention, formulated for use in conjunction with a diagnostic method.

By "effective amount" in the context of passive immunization using a pharmaceutical composition, e.g., comprising an antibody, is meant the amount of the pharmaceutical composition required to passively immunize in a clinically relevant manner. An effective amount of pharmaceutical composition used to practice the methods of passive immunization described herein varies depending upon the manner of administration, the age, body weight, and general health of the subject. Ultimately, the prescribers will decide the appropriate amount and dosage regimen.

By "flanking amino acid" is meant an amino acid in a polypeptide sequence that is immediately adjacent to the N- or C-terminus of a particular defined sequence. Desirably, a flanking amino acid is present on the N- and/or C-terminus of the amino acid sequence of SEQ ID NO: 1 or 2 or a fragment thereof; and more desirably, 1, 2, 3, 4, 5, 6, 7, 8, 9, or 10 flanking amino acids are present at the N- and/or C-terminus of the amino acid sequence of SEQ ID NO: 1 or 2, or fragment thereof.

By "fusion protein" is meant a protein that includes a polypeptide of the invention, e.g., a HYR1 fragment or variant, and a fusion partner.

By "fusion partner" is meant a heterologous sequence that can be fused to a polypeptide of the invention, e.g., a HYR1 fragment or variant. Examples of fusion partners are described herein and include detection markers, stabilizing domains, sequences which aid in production or purification of the protein, or domains which increase the antigenicity of the polypeptide.

By "HYR1 polypeptide" is meant a polypeptide that is substantially identical to the amino acid sequence of SEQ ID NO: 1. Desirably, a HYR1 polypeptide has at least 70, 75%, 80%, 85%, 90%, 95%, 99%, or even 100% identity to the amino acid sequence of SEQ ID NO: 1.

By "HYR1 fragment" or "fragment of a HYR1 polypeptide" is meant a portion of a HYR1 polypeptide containing fewer than 937, 936, or 935 amino acids. In some embodiments, HYR1 fragments are between 300 and 350 or 250 to 500 amino acids in length. In some embodiments, the fragment is fewer than 937, 936, 935, 934, 933, 932, 931, or 930, 920, 910, 900, 890, 880, 870, 860, 850, 840, 830, 820, 810, 800, 790, 780, 770, 760, 750, 740, 730, 720, 710, 700, 690, 680, 670, 660, 650, 640, 630, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and, in some instances, is immunogenic.

An exemplary HYR1 fragment is Hyr1p-N (SEQ ID NO: 2), or a fragment thereof. In some instances, Hyr1p-N fragments are between 14 and 20 amino acids in length. In general, the fragment may be fewer than, e.g., 325, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 19, 18, 17, 16, 15, 14, 13, 12, or 11 amino acids, and desirably, is immunogenic. In some instances, a Hyr1p-N fragment is between 14 and 20 amino acids.

In addition, HYR1 fragments, for example, may contain one or more conservative amino acid substitutions in the sequence of SEQ ID NO: 2. Additional desirable HYR1 fragments contain one or more conservative amino acid substitutions in the sequence of SEQ ID NO: 2 and/or at least one flanking amino acid (e.g., 1, 2, 3, 4, 5, 6, 7, 8, 9, or 10 flanking amino acids) at the N- and/or C-terminus of the sequence of SEQ ID NO: 2. Other preferred HYR1 fragments contain seven or more continuous amino acids of the sequence of SEQ ID NO: 2.

Non-limiting examples of a HYR1 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, and 260-300, 270-310, 280-320, and 290-331 amino acids of the sequence of SEQ ID NO: 2; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 2; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 2; and at least one flanking amino acid (e.g., 1, 2, 3, 4, 5, 6, 7, 8, 9, or 10 flanking amino acids) at the N- and/or C-terminus of the sequence of SEQ ID NO: 2.

By "immunogenic" is meant any substance that is capable of inducing an immune response in a subject.

By "immunogenic amount" in the context of a vaccine is meant an amount of the vaccine required to induce an immune response in a subject in a clinically relevant manner. An immunogenic amount of vaccine used to practice the methods of vaccination as described herein varies depending upon the manner of administration, the age, body weight, and general health of the subject. Ultimately, the prescribers will decide the appropriate amount and dosage regimen.

The term "immunogenic amount" as used herein refers an effective amount of a particular polypeptide of the invention or a fragment thereof that can induce the host immune response against the polypeptide or the infectious agent expressing the polypeptide. This amount is generally in the range of 20 μg to 10 mg of antigen per dose of vaccine and depends on the subject to be treated, capacity of the subject's immune system to synthesize antibodies, and the degree of protection desired. The precise amount of immunogenic required can be calculated by various methods such as, for example, antibody titration. The term effective amount refers to an amount of a compound or compositions that is sufficient to provide a desired result. Thus, as used to describe a vaccine, an effective amount refers to an amount of a compound or composition (e.g., an antigen) that is sufficient to produce or elicit a protective immune response. An effective amount with respect to an immunological composition is an amount that is sufficient to elicit an immune response, whether or not the response is protective.

By "isolated" or "purified" is meant separated from other naturally accompanying components. Typically, a compound (e.g., nucleic acid, polypeptide, antibody, or small molecule) is substantially isolated when it is at least 60%, by weight, free from the proteins and/or naturally occurring organic molecules with which it is naturally associated. The definition also extends, e.g., to a polypeptide or nucleic acid molecule separated from its flanking sequences (e.g., for an amino acid sequence, isolated refers to a sequence that is free from the flanking amino acids with which the sequence is naturally associated in a polypeptide). In some instances, the compound is at least 75%, more preferably at least 90%, and most preferably at least 99%, by weight, isolated. An isolated compound, e.g., polypeptide, may be obtained by standard techniques, for example, by extraction from a natural source (e.g., purification from a cell infected with *Candida*); by expression of a recombinant nucleic acid encoding a HYR1 fragment or variant, or a fusion protein thereof; or by chemically synthesizing the polypeptide. Purity can be measured by any appropriate method, e.g., by column chromatography, polyacrylamide gel electrophoresis, or HPLC analysis. Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment.

By "linked to" or "conjugated to" in the context of a conjugate is meant a covalent or non-covalent interaction between the polypeptide and the carrier or fusion partner. Non-covalent interactions include, but are not limited to, hydrogen bonding, ionic interactions among charged groups, electrostatic binding, van der Waals interactions, hydrophobic interactions among non-polar groups, lipophobic interactions, and Log P-based attractions.

By "monoclonal antibody" is meant an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al., *Nature* 256:495 (1975), a transgenic animal (e.g., Lonberg et al., *Nature* 368(6474):856-859 (1994)), recombinant DNA methods (e.g., U.S. Pat. No. 4,816,567), or using phage, yeast, or synthetic scaffold antibody libraries using the techniques described in, for example, Clackson et al., *Nature* 352:624-628 (1991) and Marks et al., *J. Mol. Biol.* 222:581-597 (1991).

By "nucleic acid molecule" is meant a molecule, e.g., RNA or DNA, having a sequence of two or more covalently bonded, naturally occurring or modified nucleotides. The nucleic acid molecule may be, e.g., single or double stranded, and may include modified or unmodified nucleotides, or mixtures or combinations thereof. Various salts, mixed salts, and free acid forms are also included.

The term "nucleic acid", also referred to as polynucleotides, encompasses ribonucleic acid (RNA) or deoxyribonucleic acid (DNA), probes, oligonucleotides, and primers and can be single stranded or double stranded. DNA can be either complementary DNA (cDNA) or genomic DNA, and can represent the sense strand, the anti-sense strand or both. Examples of nucleic acids are RNA, cDNA, or isolated genomic DNA. Such nucleic acids include, but are not limited to, nucleic acids comprising substantially the same nucleotide sequences as described herein.

By "patient" or "subject" is meant a mammal, including, but not limited to, a human or non-human mammal, such as a bovine, equine, canine, ovine, or feline. A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

The terms "pharmaceutically acceptable carrier" and "pharmaceutically acceptable excipient" are used interchangeably and mean a carrier or excipient that is physiologically acceptable to the treated patient while retaining the therapeutic properties of the compound with which it is administered. One exemplary pharmaceutically acceptable carrier substance is physiological saline. Other physiologically acceptable carriers and their formulations are known to those skilled in the art and described, for example, in Remington's Pharmaceutical Sciences, (20$^{th}$ edition), ed. A. Gennaro, 2000, Lippincott, Williams & Wilkins, Philadelphia, Pa.

By "pharmaceutical composition" is meant a composition containing a polypeptide, conjugate, vaccine, or antibody of the invention, formulated with a pharmaceutically acceptable excipient, and manufactured or sold with the approval of a governmental regulatory agency as part of a therapeutic regimen for the treatment or prevention of a disease or event in a mammal. Pharmaceutical compositions can be formulated, for example, for intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form. The invention also provides a pharmaceutical composition comprising a pharmaceutically acceptable carrier and a compound comprising an anti-*Acinetobacter* protein antibody as disclosed herein or an anti-HYR1 antibody having specific reactivity to an HYR1 protein (SEQ ID NO: 1) or a fragment thereof as is disclosed herein. The invention additionally provides a method of treating or preventing infections from gram negative bacteria such as bacteria from the *Acinetobacter* genus including, for example, *Acinetobacter baumannii*, in a subject in need thereof. The methods of the invention can include administering a therapeutically effective amount of a pharmaceutical composition containing a pharmaceutically acceptable carrier and a compound comprising an anti-*Acinetobacter* protein antibody as disclosed herein or an anti-HYR1 antibody having specific reactivity to an HYR1 protein (SEQ ID NO: 1) or a fragment thereof. The invention additionally provides a method of treating or preventing a bacterial infection in a subject in need thereof by administering a therapeutically effective amount of a vaccine composition as disclosed herein.

As used herein, the term "polypeptide" is intended to refer to two or more amino acids. Such polypeptides typically are continuous and unbranched peptide. A peptide is a short polymer of amino acid monomers. "Proteins" are intended to include one or more polypeptides arranged in a biologically functional way. The amino acids comprising the polypeptides of the invention may be linked by peptide bonds or other bonds, for example, ester or ether bonds. The amino acids comprising the polypeptides of the invention can include non-genetically coded amino acids that either occur naturally or are chemically synthesized. A polypeptide of the invention can also encompass one or more conservative substitutions. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are also included within polypeptides of the invention so long as the polypeptide retains some or all of its function as described herein.

The invention polypeptides can also include derivatives, analogues and functional mimetics thereof, provided that such polypeptide retains some or all of its function as disclosed herein. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Polypeptides of the present invention also include any polypeptide having one or more additions and/or deletions of residues, relative to the sequence of a polypeptide whose sequence is shown herein, so long as immunogenic activity as disclosed herein is maintained.

The invention polypeptides can be isolated by a variety of methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, (1990)). Alternatively, the isolated polypeptides of the present invention can be obtained using well-known recombinant methods (see, for example, Ausubel et al., "Immunology," *Short Protocols in Molecular Biology*, John Wiley & Sons, Inc. Chapter 11. Page 11.1-11.29 (1999); Sambrook and Russell, "Molecular Cloning: A Laboratory Manual," Cold Spring Harbor Laboratory (2001)). The methods and conditions for biochemical purification of a polypeptide of the invention can be chosen by those skilled in the art, and purification monitored, for example, by an immunological assay or a functional assay.

An example of the means for preparing an invention polypeptide is to express nucleic acids encoding a polypeptide of the invention in a suitable host cell, such as a bacterial cell, a yeast cell, an amphibian cell such as an oocyte, or a mammalian cell, using methods well known in the art, and recovering the expressed polypeptide, again using well-known purification methods, so described herein. Invention polypeptides can be isolated directly from cells that have been transformed with expression vectors as described herein. The invention polypeptides can also be produced by chemical synthesis. Methods for chemically synthesizing polypeptides are well known in the art and are commercially available.

Recombinantly expressed polypeptides of the invention can also be expressed as fusion proteins with appropriate fusion partners. An appropriate fusion partner can be an amino acid sequence that is not normally connected to the amino acid sequence such as an heterologous sequence, which serves a particular function or provides additional characteristic to the polypeptides of the invention. Non-limiting examples of suitable heterologous sequences include a detectable marker, a stabilizing domain, a carrier protein for the generation of antibodies, a linker sequence and a sequence that aids in the purification of the polypeptide. Sequences that can aid in the purification of the invention polypeptides include affinity tags, such as glutathione S transferase (GST) or poly His. Thus, in some aspects, the invention provide a fusion protein having a polypeptide as disclosed herein fused to a heterologous sequence, a carrier protein, an affinity tag or a linker sequence.

The present invention also provides compositions containing an acceptable carrier and any of the isolated polypeptides disclosed herein, alone or in combination with each other. These polypeptides can be recombinantly derived, chemically synthesized or purified from native sources. As used herein, the term "pharmaceutically acceptable carrier" encompasses any of the standard pharmaceutical carriers known in the art, such as phosphate buffered saline solution, water and emulsions such as an oil and water emulsion, and various types of wetting agents.

The invention also provides a method for expression of a polypeptide as disclosed herein by culturing cells containing a nucleic acid that encodes the polypeptide under conditions suitable for expression of polypeptide. Thus, there is provided a method for the recombinant production of a polypeptide of the invention by expressing the nucleic acid sequences encoding the polypeptide in suitable host cells. Recombinant DNA expression systems that are suitable for production of polypeptides are described herein and are well-known in the art (see, Ausubel et al., supra, 1999). For example, the above-described nucleotide sequences can be incorporated into vectors for further manipulation. Vectors can include a recombinant DNA or RNA plasmid or virus containing discrete elements that are used to introduce heterologous DNA into cells for either expression or replication thereof.

By "specifically binds" is meant the preferential association of a binding moiety (e.g., an antibody, antibody fragment, receptor, ligand, or small molecule portion of an agent as described herein) to a target molecule (e.g., a polypeptide or conjugate including same) or to a cell or tissue bearing the target molecule (e.g., a cell surface antigen, such as a receptor or ligand) and not to non-target molecules, cells, or tissues lacking the target molecule. It is recognized that a certain degree of non-specific interaction may occur between a binding moiety and a non-target molecule (present alone or in combination with a cell or tissue). Nevertheless, specific binding may be distinguished as mediated through specific recognition of the target molecule. Specific binding results in a stronger association between the binding moiety (e.g., an antibody) and the target molecule (e.g., a polypeptide or conjugate including same) than between the binding moiety and, e.g., non-target molecules or other compositions lacking the target molecule. Specific binding typically results in greater than 2-fold, preferably greater than 5-fold, more preferably greater than 10-fold and most preferably greater than 100-fold increase in amount of bound binding moiety (per unit time) to e.g., a cell or tissue bearing the target molecule or marker as compared to a cell or tissue lacking that target molecule or marker. Binding moieties bind to the target molecule or marker with a dissociation constant of e.g., less than $10^{-6}$M, less than $10^{-7}$M, $10^{-8}$M, $10^{-9}$M, $10^{-10}$M, $10^{-11}$M, or $10^{-12}$M, or even less than $10^{-13}$M, $10^{-14}$M, or $10^{-15}$M. Specific binding to a protein under such conditions requires a binding moiety that is selected for its specificity for that particular protein. A variety of assay formats are appropriate for selecting binding moieties (e.g., antibodies) capable of specifically binding to a particular target molecule. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

By "substantially identical" is meant an amino acid sequence or nucleic acid sequence that exhibits at least 50% identity to a reference sequence. Such a sequence is generally at least, e.g., 50%, 60%, 70%, 75%, 80%, 85%, 90%, 95%, 96%, 97%, 98%, or 99% identical at the amino acid level or nucleic acid level to a reference sequence. In general, for polypeptides, the length of comparison sequences can be at least five amino acids, e.g., 10, 20, 30, 40, 50, 60, 70, 80, 90, 100, 125, 150, 175, 200, 250, 300, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., J. Mol. Biol. 147:195-7, 1981) and BLAST (Basic Local Alignment Search Tool; Altschul et al., J. Mol. Biol. 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared.

A "target molecule" or "target cell" is meant a molecule (e.g., a polypeptide, epitope, antigen, receptor, or ligand) or cell to which a binding moiety (e.g., an antibody) can specifically bind. In some instances, target molecules are exposed on the exterior of a target cell (e.g., a cell surface or secreted protein), but target molecules may alternately or also be present in the interior of a target cell.

The "therapeutically effective amount" will vary depending on the protein, polypeptide, or antibody compositions used, the disease and its severity and the age, weight, etc., of the patient to be treated, all of which is within the skill of the attending clinician. It is contemplated that a therapeutically effective amount of one or more of a protein, polypeptide, or antibody composition described herein will alter the pathogenicity of gram negative bacteria. A therapeutically effective amount is distinguishable from an amount having a biological effect. A protein, polypeptide, or antibody composition of the present invention may have one or more biological effects in vitro or even in vivo, such as reducing the function of a protein or polypeptide expressed by a gram negative bacteria. A biological effect, however, may not result in any clinically measurable therapeutically effect as described herein as determined by methods within the skill of the attending clinician.

By "treating" or "treatment" is meant the medical management of a patient with the intent to cure, ameliorate, stabilize, reduce the likelihood of, or prevent a disease, pathological condition, disorder, or event, by administering a pharmaceutical composition. This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief of symptoms rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

By "vaccine," as used herein, is meant a composition that elicits an immune response in a subject to which it is administered.

By "vaccinate," as used herein, is meant to treat a patient by administering a vaccine, e.g., to prevent or ameliorate a disease, pathological condition, disorder, or event.

By "variant" in the context of a polypeptide or portion thereof as described herein, or a nucleic acid molecule encoding same, is meant to include substitutions or alterations in the amino acid sequence or nucleic acid sequence, e.g., resulting in a substantially identical sequence. A polypeptide having a variant sequence may maintain at least one biological activity of the original polypeptide, e.g., immunogenic activity. The term "variant" includes, e.g., amino acid insertional derivatives such as amino and/or carboxyl-terminal fusions, as well as intrasequence insertions of single or multiple amino acids. Insertional amino acid variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue inserted in its place. Where the protein is derivatized by amino acid substitution, amino acids are generally replaced by conservative substitutions, e.g., other amino acids having similar physical chemical properties such as hydrophobicity, hydrophilicity, electronegativity, bulky sidechains and the like.

For purposes of the present invention, variants also include single or multiple substitutions, deletions and/or additions of any component(s) naturally or artificially associated with the portion of a naturally occurring protein from which the polypeptide may be derived, such as carbohydrate, lipid and/or other proteinaceous moieties. All such molecules are encompassed by the term "variant."

By "variant sequence" is meant the amino acid or nucleic acid sequence of a variant as defined herein.

Other features and advantages of the invention will be apparent from the following Detailed Description, the drawings, and the claims.

DETAILED DESCRIPTION OF THE INVENTION

Figure 1:
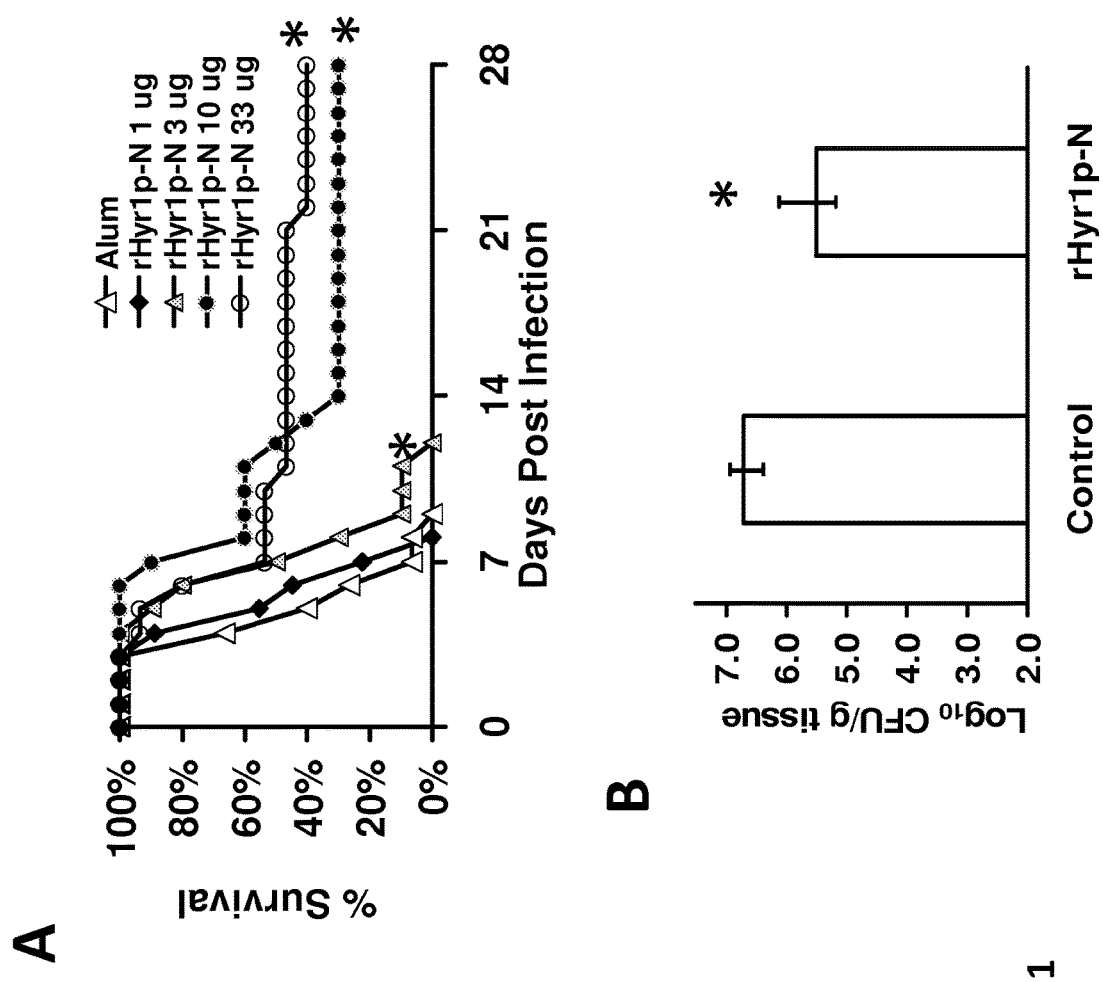
FIGS. 1A-1B: rHyr1p-N vaccine improved survival and decreased fungal burden in mice with *Candida albicans* infection. (A) Survival of vaccinated or control mice (n=15 per group) infected i.v. with *Candida albicans* 15563 strain, a clinical isolate ($9 \times 10^5$ per dose), *, P<0.001 compared to alum alone by the log-rank test. (B) Kidney fungal burden of mice (n=10 per arm) vaccinated with 30 μg rHyr1p-N+ alum or alum alone and harvested 3 days post infection with *C. albicans* 15663 ($7 \times 10^5$ per dose). Data are presented as median±interquartile ranges. *, P<0.001 compared to results obtained from kidneys harvested from mice vaccinated with alum alone by the Mann-Whitney U test.

*Candida albicans* is a common pathogen in humans. For example, *C. albicans*, while normally a harmless commensal, can cause a variety of conditions ranging from superficial mucocutaneous infection such as vaginal and/or oropharyngeal candidiasis, to deep organ involvement in disseminated candidiasis. Prior to causing disease, the fungus colonizes the gastrointestinal tract, and in some cases skin and mucous membranes. Adherence to host mucosal surfaces is a key prerequisite for this initial step. After colonization, *C. albicans* enters the bloodstream via infected intravascular devices or by transmigration through gastrointestinal mucosa compromised by chemotherapy or stress ulcerations. Organisms then disseminate via the bloodstream, bind to and penetrate the vascular endothelium to egress from the vascular tree, and invade deep organs such as liver, spleen, and kidney.

The identification of the HYR1 fragments and other compositions described herein allow, e.g., for the effective treatment of and vaccination against not only candidiasis but also *Acinetobacter* infection.

The invention provides polypeptides, e.g., derived from HYR1 or Hyr1p-N, conjugates, vaccines, antibodies, compositions, methods of vaccination using same, and methods of production of same, as described in further detail below.

Polypeptides

The invention features polypeptides, e.g., isolated polypeptides, derived from HYR1, e.g., Hyr1p (SEQ ID NO: 1) or Hyr1p-N (SEQ ID NO: 2), e.g., including the amino acid sequence of any one of SEQ ID NOs: 3-10, or a variant sequence thereof having zero, one, two, or three substitutions, deletions, or additions to the amino acid sequence of any one of SEQ ID NOs: 3-10, wherein the polypeptide does not include more than 20 contiguous amino acids of SEQ ID NO: 2.

SEQ ID NO: 1 is an amino acid sequence of *C. albicans* Hyr1p (SEQ ID NO: 1).
(SEQ ID NO: 1)

MKVVSNFIFTILLTLNLSAALEVVTSRIDRGGIQGFHGDVEVHSGATWAILGTTLCSFEG

GLEVEKGASLFIKSDNGPVLALNVALSTLVRPVINNGVISLNSKSSTSFSNFDIGGSSFT

NNGEIYLASSGLVKSTAILYAREWTNNGLIVAYQNQKAAGNTAFGTAYQTITNNGQICLR

HQDFVPATKIKGTGCVTADEDTWIKLGNTILSVEPTHNFYLKDSKSSLIVHAVSSNQTFT

VEGFGNGNKLGITLPLTGNRDHFRFEYYPDTGILQLRAAAIPQYFKIGKGYDSKIFRIVN

-continued

SRGLKNAVTYDGPVPNNETPAVCLIPCTNGPSAPESESDLNTPTTSSIETSSYSSAATES

SVVSESSSAVDSLTSSSLSSKSESSDVVSSTTNIESSSTAIETTMNSESSTDAGSSSISQ

SESSSTAITSSSETSSSESMSASSTTASNTSIETDSGIVSQSESSSNALSSTEQSITSSP

GQSTIYVNSTVTSTITSCDENKCTEDVVTIFTTVPCSTDCVPTTGDIPMSTSYTQRTVTS

TITNCDEVSCSQDVVTYTTNVPHTTVDATTTTTTSTGGDNSTGGNESGSNHGPGNGSTEG

SGNGSGAGSNEGSQSGPNNGSGSGSEGGSNNGSGSDSGSNNGSGSGSNNGSGSGSTEGSE

GGSGSNEGSQSGSGSQPGPNEGSEGGSGSNEGSNHGSNEGSGSGSGSGSNNGSGSGSQSG

SGSGSQSGSESGSNSGSNEGSNPGAGNGSNEGSGQGSGNGSEAGSGQGSGPNNGSGSGHN

DGSGSGSNQGSNPGAGSGSGSESGSNAGSHSGSNEGAKTDSIEGFHTESKPGFNTGAHTD

ATVTGNSVANPVTTSTESDTTISVTVSITSYMTGFDGKPKPFTTVDVIPVPHSMPSNTTD

SSSSVPTIDTNENGSSIVTGGKSILFGLIVSMVVLFM

SEQ ID NO: 2 is an amino acid sequence of a recombinant N-terminal domain of Hyr1p (rHyr1p-N, SEQ ID NO: 2).

(SEQ ID NO: 2)

```
1       TSRIDRGGIQ GFHGDVKVHS
21      GATWAILGTT LCSFFGGLEV
41      EKGASLFIKS DNGPVLALNV
61      ALSTLVRPVI NNGVISLNSK
81      SSTSFSNFDI GGSSFTNNGE
101     IYLASSGLVK STAYLYAREW
121     TNNGLIVAYQ NQKAAGNIAF
141     GTAYQTITNN GQICLRHQDF
161     VPATKIKGTG CVTADEDTWI
181     KLGNTILSVE PTHNFYLKDS
201     KSSLIVHAVS SNQTFTVHGF
221     GNGNKLGLTL PLTGNRDHFR
241     FEYYPDTGIL QLRAAALPQY
261     FKIGKGYDSK LFRIVNSRGL
281     KNAVTYDGPV PNNEIPAVCL
301     IPCTNGPSAP ESESDLNTPT
321     TSSIET
```

SEQ ID NOs: 3-10 are 14-mer fragments of the amino acid sequence of Hyr1p-N (SEQ ID NO: 2), as shown in Table 1.

TABLE 1

Exemplary Hyr1p-N Fragments

| SEQ ID NO. | Sequence |
|---|---|
| 3 | GPSAPESESDLNTP |
| 4 | GNRDHFRFEYYPDT |
| 5 | GYDSKLFRIVNSRG |
| 6 | KIKGTGCVTADEDT |

TABLE 1-continued

Exemplary Hyr1p-N Fragments

| SEQ ID NO. | Sequence |
|---|---|
| 7 | LKNAVTYDGPVPNN |
| 8 | NSKSSTSFSNFDIG |
| 9 | EPTHNFYLKDSKSS |
| 10 | TSRIDRGGIQGFHG |

The polypeptides of Table 1 or other polypeptides described herein may have a variant or otherwise modified amino acid sequence. For example, in variants of the polypeptides of Table 1, each substitution, deletion, or addition, if any, may be made, e.g., at position 1, 2, 3, 4, 5, 6, 7, 8, 9, 10, 11, 12, 13, or 14, or at the N- or C-terminal end of the polypeptide.

In some instances, the polypeptide is between 14 and 20 amino acids, e.g., 14, 15, 16, 17, 18, 19, or 20 amino acids. In other instances, the polypeptide is shorter than 14 amino acids, e.g., 11, 12, or 13 amino acids. The polypeptide may be longer than 20 amino acids provided that it does not include more than 20 contiguous amino acids of SEQ ID NO: 2.

In some instances, a modification to a polypeptide as described herein does not substantially reduce the biological activity, e.g., immunogenic activity, of the polypeptide. The modified polypeptide may have or may optimize a characteristic of a polypeptide, such as in vivo stability, bioavailability, toxicity, immunological activity, immunological identity, or conjugation properties.

Modifications include those by natural processes, such as posttranslational processing, or by chemical modification techniques known in the art. Modifications may occur anywhere in a polypeptide including the polypeptide backbone, the amino acid side chains, and the amino- or carboxy-terminus. The same type of modification may be present in the same or varying degrees at several sites in a given polypeptide, and a polypeptide may contain more than one type of modification.

A variant or otherwise modified polypeptide can also include one or more amino acid insertions, deletions, or substitutions, either conservative or non-conservative (e.g., D-amino acids, desamino acids) in the polypeptide sequence. For example, the addition of one or more cysteine residues to the amino or carboxy terminus of any of the polypeptides of the invention can facilitate conjugation of these polypeptides. Exemplary polypeptides having an N- or C-terminal cysteine include, e.g., the polypeptides of SEQ ID NOs: 11-18, e.g., as shown in Table 2, and as described further in Example 1.

TABLE 2

Anti-Hyr1 Peptides

| Peptide No. | SEQ ID NO. | Sequence | MW (kDa) | pI | Purity (%) |
| --- | --- | --- | --- | --- | --- |
| 1 | 11 | CGPSAPESESDLNTP | 1.5 | 3.44 | 86.1 |
| 2 | 12 | CGNRDHFRFEYYPDT | 1.9 | 5.69 | 99.4 |
| 3 | 13 | CGYDSKLFRIVNSRG | 1.7 | 9.16 | 95.7 |
| 4 | 14 | CKIKGTGCVTADEDT | 1.5 | 4.70 | 86.4 |
| 5 | 15 | CLKNAVTYDGPVPNN | 1.6 | 6.25 | 94.1 |
| 6 | 16 | NSKSSTSFSNFDIGC | 1.6 | 6.25 | 91.4 |
| 7 | 17 | CEPTHNFYLKDSKSS | 1.8 | 7.19 | 85.8 |
| 8 | 18 | TSRIDRGGIQGFHGC | 1.6 | 8.27 | 91.8 |

Amino acid substitutions can be conservative (i.e., wherein a residue is replaced by another of the same general type or group) or non-conservative (i.e., wherein a residue is replaced by an amino acid of another type). In addition, a non-naturally occurring amino acid can be substituted for a naturally occurring amino acid (i.e., non-naturally occurring conservative amino acid substitution or a non-naturally occurring non-conservative amino acid substitution).

Polypeptides made synthetically, e.g., using methods known in the art, can include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Variants may be generated by substitutional mutagenesis and retain or even increase the biological activity, e.g., immunogenic activity, of the original polypeptide.

The polypeptides described herein can be obtained, e.g., by chemical synthesis using a commercially available automated peptide synthesizer. The synthesized protein or polypeptide can be precipitated and further purified, for example by high performance liquid chromatography (HPLC). Alternatively, the proteins and polypeptides can be obtained by recombinant methods, e.g., that are well-known in the art.

Conjugates

Polypeptides of the invention may be conjugated to another moiety or particle.

Protein Moieties

In some instances, it may be useful to conjugate the polypeptide to a protein that is immunogenic in the species to be immunized, e.g., keyhole limpet hemocyanin (KLH), CRM197, tetanus toxoid, diptheria toxoid, serum albumin, bovine thyroglobulin, soybean trypsin inhibitor, or a polycation (poly-L-Lysine or poly-L-arginine), e.g., using a bifunctional or derivatizing agent as known in the art, for example, maleimidobenzoyl sulfosuccinimide ester (conjugation through cysteine residues), N-hydroxysuccinimide (through lysine residues), glutaraldehyde, or succinic anhydride.

In some instances, the conjugate may be a recombinant fusion protein, e.g., to facilitate expression and purification of the polypeptide.

Particles for Conjugation or Display of Polypeptides

In some instances, polypeptides are conjugated to or displayed on a particle, e.g., a phage, a yeast, a virus, a virosome, or a recombinant virus-like particle.

For example, one or more polypeptides may be conjugated to a phage, a yeast, or a virus particle, e.g., to the surface of the particle. In one embodiment, a nucleic acid molecule encoding the polypeptide is inserted into the phage, yeast, or virus particle, resulting in expression of the polypeptide in the phage, yeast, or virus, e.g., at the surface of the particle. The phage, yeast, or virus population containing the polypeptide may then be isolated and prepared, e.g., as a vaccine, by adding a pharmaceutically acceptable excipient.

In some embodiments, polypeptides as described herein are conjugated to a virosome or virus-like particle (VLP). Virosomes and VLPs generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. Viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Q.beta.-phage (such as coat proteins), GA-phage, fr-phage, AP205 phage, and Ty (such as retrotransposon Ty protein p 1).

Virosomes are discussed further in, e.g., Gluck et al. (2002), Vaccine 20:B10-B16, which is incorporated by reference in its entirety.

VLPs are discussed further, e.g., in Niikura et al. (2002), Virology 293:273-280; Lenz et al. (2001), J Immunol 166:5346-5355; Pinto et al. (2003), J Infect Dis 188:327-338; Gerber et al. (2001), Viral 75:4752-4760; WO03/024480; and WO03/024481, each of which is incorporated by reference in its entirety.

Antibodies

The invention features monoclonal and polyclonal antibodies that bind to the polypeptides or conjugates described herein.

Monoclonal Antibodies

Monoclonal antibodies may be made, e.g., using the hybridoma method first described by Kohler et al., *Nature* 256:495, 1975, or may be made by recombinant DNA methods (see, e.g., U.S. Pat. No. 4,816,567). In the hybridoma method, a mouse or other appropriate host animal, such as a hamster or macaque monkey, is immunized, e.g., using a polypeptide or conjugate described herein, to elicit lymphocytes that produce or are capable of producing antibodies that will specifically bind to the polypeptide or conjugate used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103, Academic Press, 1986).

The hybridoma cells thus prepared are seeded and grown in a suitable culture medium that can contain one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Exemplary myeloma cells are those that fuse efficiently, support stable high-level production of antibody by the selected antibody-producing cells, and are sensitive to a medium such as HAT medium. Among these, particular myeloma cell lines that may be considered for use are murine myeloma lines, such as those derived from MOPC-21 and MPC-11 mouse tumors available from the Salk Institute Cell Distribution Center, San Diego, Calif., USA, and SP-2 or X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.* 133:3001, 1984; Brodeur et al., Monoclonal Antibody Production Techniques and Applications, pp. 51-63, Marcel Dekker, Inc., New York, 1987).

Culture medium in which hybridoma cells are growing is assayed for production of monoclonal antibodies directed against the antigen. The binding specificity of monoclonal antibodies produced by hybridoma cells can be determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, clones may be subcloned by limiting dilution procedures and grown by standard methods (Goding, Monoclonal Antibodies: Principles and Practice, pp. 59-103, Academic Press, 1986). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described, for example, in McCafferty et al., *Nature* 348:552-554, 1990.

Clackson et al., *Nature* 352:624-628, 1991 and Marks et al., *J. Mol. Biol.* 222:581-597, 1991, describe the isolation of murine and human antibodies, respectively, using phage libraries. Subsequent publications describe the production of high affinity (nM range) human antibodies by chain shuffling (Marks et al., *Bio/Technology* 10:779-783, 1992), as well as combinatorial infection and in vivo recombination as a strategy for constructing very large phage libraries (Waterhouse et al., *Nucl. Acids. Res.* 21:2265-2266, 1993). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison et al., *Proc. Natl. Acad. Sci. U.S.A.* 81:6851, 1984), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Polyclonal Antibodies

Polyclonal antibodies are typically raised in animals by multiple injections, e.g., subcutaneous or intraperitoneal injections, of the relevant antigen and an adjuvant. In some instances, it may be useful to conjugate the polypeptide to a protein that is immunogenic in the species to be immunized, e.g., keyhole limpet hemocyanin (KLH), CRM197, tetanus toxoid, diptheria toxoid, serum albumin, bovine thyroglobulin, soybean trypsin inhibitor, or a polycation (poly-L-Lysine or poly-L-arginine), e.g., using a bifunctional or derivatizing agent as known in the art, for example, maleimidobenzoyl sulfosuccinimide ester (conjugation through cysteine residues), N-hydroxysuccinimide (through lysine residues), glutaraldehyde, or succinic anhydride.

In addition, an antibody useful in the present invention can be a naturally occurring antibody as well as a non-naturally occurring antibody, including, for example, a single chain antibody, a chimeric, bifunctional or humanized antibody, as well as antigen-binding fragments thereof. Such non-naturally occurring antibodies can be constructed using solid phase peptide synthesis, can be produced recombinantly or can be obtained, for example, by screening combinatorial libraries as described by Ponsel et al. (*Molecules*, 16(5):3675-3700 (2011)). These and other methods of making, for example, chimeric, humanized, CDR-grafted, single chain, and bifunctional antibodies are well known to those skilled in the art and are commercially available.

Anti-*Acinetobacter* protein antibodies can be raised using an immunogenic polypeptide such as an isolated polypeptide having the amino acid sequence of SEQ ID NOS:3-10 or SEQ ID NOS: 11-18 or any of the specific *Acinetobacter baumannii* proteins disclosed herein, or a fragment thereof, which can be prepared from natural sources or produced recombinantly, or a peptide portion of the *Acinetobacter baumannii* protein. Such peptide portions of the *Acinetobacter baumannii* proteins disclosed herein are functional antigenic fragments of the antigenic peptides, which can be used to generate an *Acinetobacter* protein-specific antibody. A non-immunogenic or weakly immunogenic polypeptide or portion thereof can be made immunogenic by coupling the polypeptide to a carrier molecule such as bovine serum albumin (BSA) or keyhole limpet hemocyanin (KLH). Various other carrier molecules and methods for coupling a polypeptide to a carrier molecule are well known in the art (see, for example, Harlow and Lane, supra, 1988). An immunogenic polypeptide fragment can also be generated by expressing the peptide portion as a fusion protein, for example, to glutathione S transferase (GST), polyHis or the like. Methods for expressing peptide fusions are well known to those skilled in the art (Ausubel et al., supra).

The invention further provides a method for detecting the presence of gram negative bacteria, such as bacteria of the *Acinetobacter* genus in a sample by contacting the sample with a specific antibody, and detecting the presence of specific binding of the antibody to the sample, thereby detecting the presence of the gram negative bacteria in the sample. For example, anti-*Acinetobacter* protein specific antibodies can be used in the diagnostic methods disclosed herein to detect the level of *Acinetobacter* present in a sample.

As used herein, the term "sample" is intended to mean any biological fluid, cell, tissue, organ or portion thereof, that includes or potentially includes nucleic acids or polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or protein preparation.

Immunological procedures useful for in vitro detection of target *Acinetobacter* proteins in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra, 1988; Harlow and Lane, *Using Antibodies: A Laboratory Manual*, Cold Spring Harbor Press (1999)).

An antibody can be made detectable by various means well known in the art. For example, a detectable marker can be directly attached to the antibody or indirectly attached using, for example, a secondary agent that recognizes the anti-*Acinetobacter* protein antibody. Useful markers include, for example, radionucleotides, enzymes, binding proteins such as biotin, fluorogens, chromogens and chemiluminescent labels.

Labels that are useful in the invention include single atoms and molecules that are either directly or indirectly involved in the production of a detectable signal. Any label or indicating means can be linked to invention nucleic acids, polypeptides, or antibodies. These atoms or molecules can be used alone or in conjunction with additional reagents. Such labels are themselves well-known in clinical diagnostic chemistry.

In one embodiment, a label can be a fluorescent labeling agent that chemically binds to antibodies without denaturation to form a fluorochrome (dye) that is a useful immunofluorescent tracer. Methods for making and using a fluorescent labeling agent are well known in the art and are commercially available.

In one embodiment, the labeling group can be an enzyme, such as horseradish peroxidase (HRP), glucose oxidase, and the like. In another embodiment, radioactive elements are employed as labeling agents. The linking of a label to a substrate, i.e., labeling of nucleic acids, antibodies and polypeptides, is well known in the art. For instance, an invention antibody can be labeled by metabolic incorporation of radiolabeled amino acids provided in the culture medium. See, for example, Galfre et al., *Meth. Enzymol.*, 73:3-46 (1981). Additionally, an invention antibody can be labeled by incubating the invention antibody conjugated with a bifunctional chelator in a solution of radioisotopes. See, for example, U.S. Pat. No. 7,229,620. Conventional means of protein conjugation or coupling by activated functional groups are commercially available.

Accordingly, in some embodiments, the invention provides a method for detecting the presence of *Acinetobacter* in a sample. These methods can include contacting a sample with an antibody as described here, and detecting the presence of specific binding of the antibody to the sample, thereby detecting the presence of *Acinetobacter* in the sample. In some aspects, the binding of the antibody is to a specific *Acinetobacter* protein identified herein. For example, the method can include binding to an outer membrane protein 1 of *Acinetobacter baumannii*, an outer membrane protein 2 of *Acinetobacter baumannii*, an ferric siderophore receptor protein of *Acinetobacter baumannii*, an Dnak heat shock protein of *Acinetobacter baumannii*, an elongation factor G of *Acinetobacter baumannii*, an organic solvent tolerance protein precursor of *Acinetobacter baumannii*, a putative lipoprotein precursor (VacJ) transmembrane of *Acinetobacter baumannii*, a putative glucose-sensitive porin (OprB-like) of *Acinetobacter baumannii*, an AdeA membrane fusion protein of *Acinetobacter baumannii*, a cell division protein of *Acinetobacter baumannii*, or a cell division protein FtsZ of *Acinetobacter baumannii* that is present in the sample.

The compositions and methods described for detecting and analyzing *Acinetobacter* are equally applicable for detecting *Candida*.

Vaccines and Antibody-Containing Pharmaceutical Compositions

Formulations for vaccines and antibody-containing pharmaceutical compositions (collectively "compositions") as described herein can be prepared using standard pharmaceutical formulation chemistries and methodologies that are readily available to the reasonably skilled artisan. For example, polypeptides, conjugates, or antibodies as described herein can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions may include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the polypeptides, conjugates, and antibodies described herein may be encapsulated, adsorbed to, or associated with particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulated compositions will include an amount of one or more polypeptides or conjugates described herein that is sufficient to mount an immunological response. An immunogenic amount can be readily determined by one of skill in the art. Such an amount will fall in a relatively broad range that can be determined through routine trials. The compositions may contain from about 0.1% to about 99.9% of the polypeptides, conjugates, or antibodies, and can be administered directly to the subject or, alternatively, delivered ex vivo, to cells derived from the subject, using methods known to those skilled in the art.

Compositions can include a mixture of distinct polypeptides, conjugates, or antibodies as described herein. For example, vaccines may include, e.g., 2, 3, 4, 5, 6, 7, 8, or more distinct polypeptides or conjugates as described herein, e.g., containing or consisting of the amino acid sequences of SEQ ID NOs: 3-10 or 11-18, or a variant sequence thereof having up to three substitutions, deletions, or additions to the amino acid sequence of any one of SEQ ID NOs: 3-10 or 11-18. In one embodiment, a vaccine includes eight distinct polypeptides, wherein the amino acid sequence of the eight polypeptides consist of the sequence of SEQ ID NOs: 11-18. In another embodiment, antibody-containing pharmaceutical compositions may include a mixture of monoclonal or polyclonal antibodies, e.g., having distinct specificities to polypeptides or conjugates as described herein.

Substances that stimulate the immune response, e.g., adjuvants, may be included in the compositions, e.g., in vaccines. Examples of chemical compounds used as adjuvants include, but are not limited to, aluminum compounds (e.g., alum, Alhydrogel), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors.

In still another aspect, the invention provides a vaccine composition having an immunogenic amount of an HYR1 polypeptide as described herein, a fusion protein as described herein, an HYR1 protein (SEQ ID NO: 1) or a fragment thereof, an outer membrane protein 1 of *Acinetobacter baumannii* or a fragment thereof, an outer membrane protein 2 of *Acinetobacter baumannii* or a fragment thereof, an ferric siderophore receptor protein of *Acinetobacter baumannii* or a fragment thereof, an Dnak heat shock protein of *Acinetobacter baumannii* or a fragment thereof, an elongation factor G of *Acinetobacter baumannii* or a fragment thereof, an organic solvent tolerance protein precursor of *Acinetobacter baumannii* or a fragment thereof, a putative lipoprotein precursor (VacJ) transmembrane of *Acinetobacter baumannii* or a fragment thereof, a putative glucose-sensitive porin (OprB-like) of *Acinetobacter baumannii* or a fragment thereof, an AdeA membrane fusion protein of *Acinetobacter baumannii* or a fragment thereof, a cell division protein of *Acinetobacter baumannii* or a fragment thereof, or a cell division protein FtsZ of *Acinetobacter baumannii* or a fragment thereof. The vaccine composition can include an adjuvant. The formulation of the vaccine composition of the invention is effective in inducing protective immunity in a subject by stimulating both specific humoral (neutralizing antibodies) and effector cell mediated immune responses against a polypeptide antigen. The vaccine composition of the invention is also used in the treatment or prophylaxis of gram negative bacterial infections such as, for example, those caused by bacteria of the *Acinetobacter* genus including, for example, *Acinetobacter baumannii*.

The vaccine of the present invention will contain an immunoprotective quantity of polypeptide antigens and is prepared by methods well known in the art. The preparation of vaccines is generally described in, for example, M. F. Powell and M. J. Newman, eds., "Vaccine Design (the subunit and adjuvant approach)," Plenum Press (1995); A. Robinson, M. Cranage, and M. Hudson, eds., "Vaccine Protocols (Methods in Molecular Medicine)," Humana Press (2003); and D. Ohagan, ed., "Vaccine Adjuvants: Preparation Methods and Research Protocols (Methods in Molecular Medicine)," Humana Press (2000).

Polypeptides of the invention, and peptide fragments thereof can include immunogenic epitopes, which can be identified using experimental methods well known in the art. Additionally, computational modeling can also be used to identify immunogenic epitopes. See, for example, Tong et al. (*Brief Bioinform.* 8(2):96-108 (2006)) and Ponomarenko et al. (2008) "B-cell epitope prediction," in *Structural Bioinformatics*, Bourne P E and Gu J (eds) Wiley-Liss; 2 edition, pgs. 849-879. Once an epitope bearing reactivity with an antibody raised against the intact protein is identified, the peptide can be tested for specificity by amino acid substitution at every position and/or extension at both C and/or N terminal ends. Such epitope bearing polypeptides typically contain at least six to fourteen amino acid residues, and can be produced, for example, by polypeptide synthesis using methods well known in the art or by fragmenting an existing polypeptide. With respect to the molecule used as immunogens pursuant to the present invention, those skilled in the art will recognize that the polypeptide can be truncated or fragmented without losing the essential qualities as an immunogenic vaccine. For example, a polypeptide can be truncated to yield an N-terminal fragment by truncation from the C-terminal end with preservation of the functional properties of the molecule as an immunogenic. Similarly, C-terminal fragments can be generated by truncation from the N-terminal end with preservation of the functional properties of the molecule as an immunogenic. Other modifications in accordance with the teachings and guidance provided herein can be made pursuant to this invention to create other polypeptide functional fragments, immunogenic fragments, variants, analogs or derivatives thereof, to achieve the therapeutically useful properties described herein with the native proteins and polypeptides.

The vaccine compositions of the invention further contain conventional pharmaceutical carriers. Suitable carriers are well known to those of skill in the art. These vaccine compositions can be prepared in liquid unit dose forms. Other optional components, e.g., pharmaceutical grade stabilizers, buffers, preservatives, excipients and the like can be readily selected by one of skill in the art. However, the compositions can be lyophilized and reconstituted prior to use. Alternatively, the vaccine compositions can be prepared in any manner appropriate for the chosen mode of administration, e.g., intranasal administration, oral administration, etc. The preparation of a pharmaceutically acceptable vaccine, having due regard to pH, isotonicity, stability and the like, is within the skill of the art.

The immunogenicity of the vaccine compositions of the invention can further be enhanced if the vaccine further comprises an adjuvant substance. Various methods of achieving adjuvant effects for a vaccine are known. General principles and methods are detailed in "Vaccine Design: Innovative Approaches and Novel Strategies", 2011, Rappuoli R. and Bagnoli F. (eds.), Caister Academic Press, and also in "Vaccine Adjuvants and Delivery Systems", 2007, Singh, M. (ed.), John Wiley & Sons, Inc.

Vaccines according to the invention refer to a composition that can be administered to an individual to protect the individual against an infectious disease. Vaccines protect against diseases by inducing or increasing an immune response in an animal against the infectious disease. An exemplary infectious disease amenable to treatment with the vaccines of the invention include severe pneumonia, infections of the urinary tract, infections of the bloodstream and infections of other parts of the body. The vaccine-mediated protection can be humoral and/or cell mediated immunity induced in host when a subject is challenged with, for example, or an immunogenic portion of a polypeptide or protein described herein.

In addition to vaccination of subjects susceptible to *Acinetobacter* or *Candida* infections or both, the vaccine compositions of the present invention can also be used to treat, immunotherapeutically, subjects suffering from a variety of gram negative bacterial infections. Accordingly, vaccines that contain one or more of the polypeptides and/or antibody compositions described herein in combination with adjuvants, can act for the purposes of prophylactic or therapeutic treatment of infections from gram negative bacteria. In one embodiment, vaccines of the present invention will induce the body's own immune system to seek out and inhibit gram negative bacteria or *Candida* or both.

Accordingly, in some embodiments, the invention provides a method of treating or preventing an infection from gram negative bacteria in a subject in need thereof by administering a therapeutically effective amount of a pharmaceutical composition as disclosed herein or a vaccine composition as disclosed herein. For example, the invention provides methods of treating or preventing infections caused by one or more gram negative bacteria including bacteria of the *Acinetobacter* genus, such as *A. baumannii, A. iwoffii, A. haemolyticus, A. calcoaceticus, A. johnsonii, A. radioresistens*, and *A. junii*, bacteria of the *Haemophilus* genus, such as *H. aegyptius, H. aphrophilus, H. avium, H. ducreyi, H. felis, H. haemolyticus, H. influenza, H. parainfluenzae, H. paracuniculus, H. parahaemolyticus, H. pittmaniae*, and *H. somnus*, bacteria of the *Bordetella* genus, such as *B. ansorpii, B avium, B. bronchiseptica, B. hinzii, B. holmesii, B. parapertussis, B. pertussis, B. petrii*, and *B. trematum*, bacteria of the *Salmonella* genus, such as *S. typhimurium, S. bongori, S. enterica* subsp. *enterica, S. enterica* subsp. *salamae, S. arizonae, S. enterica* subsp. *diarizonae, S. enterica* subsp. *houtenae*, and *S. enterica* subsp. *indica*, bacteria of the *Yersina* genus, such as *Yersina pseudotuber, Y. aldovae, Y. aleksiciae, Y. bercovieri, Y. enterocolitica, Y. frederiksenii, Y. intermedia, Y. kristensenii, Y. mollaretii, Y. pestis, Y. pseudotuberculosis, Y. rohdei*, and *Y. ruckeri*, bacteria of the *Escherichia* genus, such as *E. albertii, E. blattae, E. coli, E. fergusonii, E. hermannii* and *E. vulneris*, bacteria of the *Pedobacter* genus, such as *P. heparinus, P. roseus* sp. *nov.* and *P. aquatilis* sp. *nov*, bacteria of the *Pseudomonas* genus, such as *P. aeruginosa, P. alcaligenes, P. mendocina, P. fluorescens, P. monteilii, P. oryzihabitans, P. luteola, P. putida, P. cepacia, P. stutzeri, P. maltophilia, P. putrefaciens, P. mallei* and *P. pseudomallei*, or bacteria of the *Klebsiella* genus, such as *K. pneumoniae, K. planticola K. oxytoca* and

*K. rhinoscleromatis*. In other embodiments, *Candida* species as disclosed herein may be treated or prevented.

Moreover, the invention also provides that in addition to being administered alone, the vaccine and pharmaceutical compositions of the invention can be co-administered with one or more antibiotics. Antibiotics that can be useful for co-administration can be readily determined by one of skill in the art. Non-limiting examples of antibiotics that can be co-administered include a carbapenem antibiotic such as imipenem, or a second line antibiotic such as polymyxins, tigecycline, or aminoglycosides. See, Bassetti et al. (Future Microbiol., 3(6): 649-60 (December 2008)).

Treatment

The invention features methods of vaccinating a mammal against candidiasis including administering to the animal a vaccine as described herein, thereby vaccinating the mammal against candidiasis. Additionally, the invention features methods of passive immunization of a mammal against candidiasis including administering to the mammal an effective amount of a pharmaceutical composition as described herein, thereby passively immunizing the mammal against candidiasis. Candidiasis may include, e.g., disseminated candidiasis, e.g., hematogenously disseminated candidiasis, or mucosal candidiasis. In some instances, the candidiasis is caused, e.g., by *Candida albicans, Candida glabrata, Candida krusei, Candida parapsilosis*, or *Candida tropicalis*. Other *Candida* species include *Candida lusitaniae* and *Candida stellatoidea*.

Vaccines and antibody-containing pharmaceutical compositions (collectively "compositions") as described herein can be administered prophylactically or therapeutically on their own or in combination with other art-known compositions that induce protective responses against pathogens (e.g., viral, bacterial, fungal, or parasitic pathogens), tumors or cancers, allergens, autoimmune disorders, or graft rejection. For example, the compositions can be administered simultaneously, separately, or sequentially, e.g., with another immunization vaccine, such as a vaccine for, e.g., influenza, malaria, tuberculosis, smallpox, measles, rubella, mumps, or any other vaccines known in the art.

Compositions as described herein can be delivered to a mammalian subject (e.g., a human or other mammal described herein) using a variety of known routes and techniques. For example, a composition can be provided as an injectable solution, suspension, or emulsion, and administered via intramuscular, subcutaneous, intradermal, intracavity, parenteral, epidermal, intraarterial, intraperitoneal, or intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, and active or passive transdermal delivery techniques.

The compositions described herein can be administered to a mammalian subject (e.g., a human or other mammal described herein) in an amount that is compatible with the dosage formulation and that will be prophylactically and/or therapeutically effective. An appropriate effective amount will fall in a relatively broad range but can be readily determined by one of skill in the art by routine trials. The "Physicians Desk Reference" and "Goodman and Gilman's The Pharmacological Basis of Therapeutics" are useful for the purpose of determining the amount needed.

Prophylaxis or therapy can be accomplished by a single direct administration at a single time point or by multiple administrations, optionally at multiple time points. Administration can also be delivered to a single or to multiple sites. Those skilled in the art can adjust the dosage and concentration to suit the particular route of delivery. In one embodiment, a single dose is administered on a single occasion. In an alternative embodiment, a number of doses are administered to a subject on the same occasion but, for example, at different sites. In a further embodiment, multiple doses are administered on multiple occasions. Such multiple doses may be administered in batches, i.e. with multiple administrations at different sites on the same occasion, or may be administered individually, with one administration on each of multiple occasions (optionally at multiple sites). Any combination of such administration regimes may be used.

In one embodiment, different compositions of the invention may be administered at different sites or on different occasions as part of the same treatment regime.

Different administrations may be performed on the same occasion, on the same day, one, two, three, four, five or six days apart, or one, two, three, four or more weeks apart. In some instances, administrations are 1 to 5 weeks apart, e.g., 2 to 4 weeks apart, such as 2 weeks, 3 weeks or 4 weeks apart. The schedule and timing of such multiple administrations can be optimised for a particular vaccine or pharmaceutical composition by one of skill in the art by routine trials.

The term "treating" or "treatment," as it is used herein is intended to mean an amelioration of a clinical symptom indicative of a bacterial infection. Amelioration of a clinical symptom includes, for example, a decrease or reduction in at least one symptom of a bacterial infection in a treated individual compared to pretreatment levels or compared to an individual with a bacterial infection. Treating also is intended to include the reduction in severity of a pathological condition, a chronic complication or an opportunistic infection which is associated with a bacterial infection. Pathological conditions, chronic complications and opportunistic infections also can be found described in, for example, Merck Manual, Sixteenth Edition, 1992, and *Acinetobacter*: Molecular Biology, Ulrike Gerischer (Editor), Caister Academic Press; 1st edition (2008).

The term "preventing" or "prevention," as it is used herein is intended to mean a forestalling of a clinical symptom indicative of a bacterial infection. Such forestalling includes, for example, the maintenance of normal physiological indicators in an individual at risk of infection by bacteria prior to the development of overt symptoms of the condition or prior to diagnosis of the condition. Therefore, preventing can include the prophylactic treatment of individuals to guard them from the occurrence of a bacterial infection. Preventing a bacterial infection in an individual also is intended to include inhibiting or arresting the development of the infection. Inhibiting or arresting the development of the condition includes, for example, inhibiting or arresting the occurrence of abnormal physiological indicators or clinical symptoms such as redness, heat, swelling and localized pain and/or others well known symptoms. Therefore, effective prevention of a bacterial infection would include maintenance of normal body temperature, weight or preventing other pathological manifestations in an individual predisposed to a bacterial infection. Individuals predisposed to a bacterial infection include an individual who is immunocompromised, for example, but not limited to, an individual with AIDS, azotemia, diabetes mellitus, diabetic ketoacidosis, neutropenia, bronchiectasis, emphysema, TB, lymphoma, leukemia, or burns, or an individual undergoing chemotherapy, bone marrow-, stem cell- and/or solid organtransplantation or an individual with a history of susceptibility to a bacterial infection. Inhibiting or arresting the development of the condition also includes, for example, inhibiting or arresting the progression of one or more pathological conditions, chronic complications or susceptibility to an opportunistic infection associated with bacteria.

Dosages

An adequate dose of the vaccines or antibody-containing pharmaceutical compositions described herein may vary depending on such factors as preparation method, administration method, age, body weight and sex of the patient, severity of symptoms, administration time, administration route, rate of excretion, and responsivity. A physician of ordinary skill in the art will easily determine and diagnose the administration dose effective for treatment.

Compositions may be prepared into unit-dose or multiple-dose preparations by those skilled in the art using a pharmaceutically acceptable carrier and/or excipient according to a method known in the art.

Vectors

The invention also provides vectors containing the nucleic acids of the invention. Suitable expression vectors are well-known in the art and include vectors capable of expressing a nucleic acid operatively linked to a regulatory sequence or element such as a promoter region or enhancer region that is capable of regulating expression of the nucleic acid. Appropriate expression vectors include vectors that are replicable in eukaryotic cells and/or prokaryotic cells and vectors that remain episomal or integrate into the host cell genome.

The terms "vector", "cloning vector" and "expression vector" mean the vehicle by which a nucleic acid can be introduced into a host cell. The vector can be used for propagation or harboring a nucleic acid or for polypeptide expression of an encoded sequence. A wide variety of vectors are known in the art and include, for example, plasmids, phages and viruses. Exemplary vectors can be found described in, for example, Sambrook et al., "Molecular Cloning: A Laboratory Manual," 3$^{rd}$ Edition. Cold Spring Harbor Laboratories, Cold Spring Harbor, N.Y., 2001; and Ausubel et al., "Current Protocols in Molecular Biology," John Wiley and Sons, Baltimore, Md. (1999)).

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors of the invention are useful for subcloning and amplifying a nucleic acid molecule and for recombinantly expressing a polypeptide as disclosed herein. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing nucleic acids of the invention. The recombinant cells are generated by introducing into a host cell a vector containing a nucleic acid molecule. The recombinant cells are transducted, transfected or otherwise genetically modified. Exemplary host cells that can be used to express recombinant molecules include mammalian primary cells; established mammalian cell lines, such as COS, CHO, HeLa, NIH3T3, HEK 293 and PC12 cells; amphibian cells, such as *Xenopus* embryos and oocytes; and other vertebrate cells. Exemplary host cells also include insect cells such as *Drosophila*, yeast cells such as *Saccharomyces cerevisiae, Saccharomyces pombe,* or *Pichia pastoris,* and prokaryotic cells such as *Escherichia coli.*

Embodiments of the present invention also provide specific HYR1 polypeptides that can act as antigens for generating an immune response to gram negative bacteria including bacteria of the *Acinetobacter* genus, for example, *Acinetobacter baumannii.* In some aspects of the invention, the HYR1 polypeptides of the invention include an amino acid sequence selected from SEQ ID NOS:3-10 as well as from CGPSAPESESDLNTP (SEQ ID NO: 11), CGNRDHFRFEYYPDT (SEQ ID NO: 12), CGYDSKLFRIVNSRG (SEQ ID NO: 13), CKIKGTGCVTADEDT (SEQ ID NO: 14), CLKNAVTYDGPVPNN (SEQ ID NO: 15), NSKSSTSFSNFDIGC (SEQ ID NO: 16), CEPTHNFYLKDSKSS (SEQ ID NO: 17), and TSRIDRGGIQGFHGC (SEQ ID NO: 18). Moreover, in some aspects of the invention, the HYR1 polypeptide can comprise less than 937, 936, 935, 934, 933, 932, 931, 930, 920, 910, 900, 890, 880, 870, 860, 850, 840, 830, 820, 810, 800, 790, 780, 770, 760, 750, 740, 730, 720, 710, 700, 690, 680, 670, 660, 650, 640, 630, 620, 610, 600, 590, 580, 570, 560, 550, 540, 530, 520, 510, 500, 490, 480, 470, 460, 450, 440, 430, 420, 410, 400, 390, 380, 370, 360, 350, 340, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30 or 20 amino acid residues in length and can be immunogenic. In some aspects of the invention, the HYR1 polypeptides of the invention are not the HYR1 polypeptide of SEQ ID NO: 1.

In still other aspects, the invention also provides embodiments wherein the polypeptides include more than one amino sequence set forth in any one of SEQ ID NOS: 3-10 or SEQ ID NOS: 11-18. For example, the polypeptides of the invention can include two amino acid sequences such as SEQ ID NO: 15 in combination with SEQ ID NO: 12, or alternatively SEQ ID NO: 11 in combination with SEQ ID NO: 17, or alternatively SEQ ID NO: 13 in combination with SEQ ID NO: 18. It is understood that the polypeptides of the invention can include two, three, four, five, six, seven or all eight amino acid sequences selected from SEQ ID NOS;3-10 or SEQ ID NOS: 11-18. It is also understood that the amino acid sequence need not be contiguous and can be linked by intervening spacer sequences, which can, for example, allow the polypeptide to present the desired amino acid sequence or epitope for generating an immune response.

In some aspects of the invention, the polypeptides of the invention include substantially the same amino acid sequence set forth in any one of SEQ ID NOS: 3-10 or SEQ ID NOS: 11-18. For example, the amino acid sequence can have at least 65%, 70%, 75%, 80%, 85%, 90%, 95%, 98% or 99% sequence identity to any one of SEQ ID NOS: 11-18, wherein the polypeptide fragment can be bound by an anti-HYR1 antibody disclosed herein. In other aspects, the HYR1 polypeptide of the invention can be immunogenic and capable of eliciting production of an anti-HYR1 antibody or immunogenic response in a subject.

As described herein, the polypeptides of the invention can encompass substantially similar amino acid sequences having at least about 65% identity with respect to the reference amino acid sequence, and retaining comparable functional and biological activity characteristic of the reference amino acid sequence. In one aspect, polypeptides having substantially the same amino acid sequence will have at least 65% identity, at least 70% identity, at least 75% identity, at least 80% identity, at least 85% identity, at least 90% identity, at least 95% identity, at least 98% identity, or at least 99% identity. It is recognized, however, that polypeptides, or encoding nucleic acids, containing less than the described levels of sequence identity arising as splice variants or that are modified by conservative amino acid substitutions, or by substitution of degenerate codons are also encompassed within the scope of the present invention.

EXAMPLES

The following example is to illustrate the invention. It is not meant to limit the invention in any way.

Example I

Active and Passive Immunization with rHyr1-N Protects Against Hematogenously Disseminated Candidiasis HYR1 belongs to the IFF gene family of *C. albicans*, which includes 12 members. It encodes a cell surface glycosyl phosphatidylinositol (GPI)-anchored protein that is expressed during hyphal formation. It has previously been shown that Hyr1p mediates *C. albicans* resistance to phagocyte killing in vitro and contributes higher fungal burden in organs rich in phagocytes (e.g. liver and spleen). Native HYR1 is positively regulated by transcription factor Bcr1p. It was found that autonomous HYR1 expression reversed the hyper-susceptibility to phagocyte-mediated killing of a bcr1 null mutant of *C. albicans* in vitro. Further, heterologous expression of HYR1 in *C. glabrata* rendered the organism more resistant to neutrophil killing. Previous studies also showed that a vaccine based on the recombinant N terminus of Hyr1p (rHyr1p-N) markedly improved survival of immunocompetent mice challenged intravenously with *C. albicans* when mixed with either Freund's or alum as an adjuvant.

The current studies were performed, inter alia, to further define the vaccine efficacy of rHyr1p-N vaccine in both immunocompetent and immunocompromised mice using FDA-approved alum as an adjuvant. Further, the breadth of protection induced by rHyr1p-N was evaluated by its efficacy against non-*albicans Candida* species. Finally, we sought to study the potential use of passive immune therapy in disseminated candidiasis using anti-Hyr1 antibodies.

Materials and Methods
*Candida* Strains and Growth Conditions
*C. albicans* 15663, *C. glabrata* 31028, *C. parapsilosis* 22019 and *C. tropicalis* 4243 are clinical bloodstream isolates collected from Harbor-UCLA Medical Center. *C. krusei* 91-1159 was generously provided by Michael Rinaldi, San Antonio, Tex. *C. albicans* strains CAAH-31 and THE31 were engineered as described in our previous study and doxycycline was used to regulate the HYR1 expression Luo et al., J. Infect. Dis. 201: 1718-1728 (2010)]. All tested strains were routinely grown in YPD (2% Bacto Peptone, 1% yeast extract, 2% dextrose). Cell densities were determined by counting in a hemacytometer.

rHyr1p-N Production
6× His tagged rHyr1p-N was produced in *E. coli* and purified by Ni-agarose affinity column as previously described [Luo et al., J. Infect. Dis. 201: 1718-1728 (2010)]. Endotoxin was removed from rHyr1p-N using ProteoSpin Endotoxin Removal kit (Norgen Bioteck Corporation, Ontario, Canada), and the endotoxin level was determined with Limulus Amebocyte Lysate endochrome (Charles River Laboratories, Wilmington, Mass.) per manufacturer's instruction. Using this procedure, endotoxin was reduced to <0.1 EU per dose of the vaccine.

Synthetic Peptides and Rabbit Anti-Hyr1p Polyclonal Antibodies
Eight peptides derived from rHyr1p-N (Table 1) were commercially synthesized and used to generate anti-Hyr1p antibodies. Peptides were >85% pure as determined by HPLC and mass spectrometry (GenScript, Piscataway, N.J.). They were conjugated to keyhole limpet hemocyanin (KLH) before raising rabbit antiserum individually using a standard immunization protocol (GenScript, Piscataway, N.J.). Total IgG from pooled serum was affinity purified using Pierce Protein A plus Agarose (Thermo Scientific, Rockford, Ill.) per the manufacturer's instruction prior to administering in passive immunization studies.

Immunofluorescence Detection of Hyr1p Cellular Localization
Indirect immunofluorescence was performed using pooled rabbit anti-Hyr1p IgG raised against 8 peptides of r-Hyr1p-N as previously described [Luo et al., J. Infect. Dis. 201: 1718-1728 (2010)]. In brief, *C. albicans* blastospores ($1\times10^7$) were pre-germinated in RPMI 1640 for 90 min at 37° C. and transferred into a 4-well chamber slide (Nalge Nunc International). After incubation at 4° C. for 30 min, the cells were blocked with 300 µl of 1.5% mouse serum, then stained with 1:500 dilution of either 1) pooled anti-Hyr1 IgGs, 2) pooled anti-Hyr1p IgG absorbed with *C. albicans* hyphae (by incubating the pooled IgG repeatedly for 4 times with $1\times10^7$ *C. albicans* hyphae for 30 min each time on ice), or 3) control rabbit IgG. The cells were counterstained with fluorescein isothiocyanate (FITC)-labeled goat anti-rabbit IgG at 1:100 dilution prior to imaging with Zeiss Axioskop fluorescence microscopy.

Immunization Protocol and Animal Studies
All active vaccinations were conducted as previously described [Luo et al., J. Infect. Dis. 201: 1718-1728 (2010)]. In brief, juvenile (10-12 week) Balb/C mice were vaccinated subcutaneously with 30 µg of rHyr1p-N mixed with alum (2% Alhydrogel; Brenntag Biosector, Frederikssund, Denmark) as an adjuvant in phosphate buffered saline (PBS) on day 0, boosted with the same dose on day 21, then infected via the tail vein on day 35 [Ibrahim et al., Infect. Immun. 73:999-1005 (2005)]. Control mice were vaccinated with alum alone.

To test the efficacy of the vaccine in immunocompromised mice, mice were vaccinated as above prior to inducing neutropenia by intraperitoneal injection of 200 mg/kg of cyclophosphamide on day −2 followed by another dose of 100 mg/kg on day +7 relative to infection. This regimen results in approximately 10 days of leucopenia with reduction in neutrophil, lymphocyte and monocyte counts, as described previously [Spellberg et al., Infect. Immun. 73:6191-6193 (2005); Fu et al., Eukaryot. Cell. 7:483-492 (2008); Sheppard et al., Antimicrob. Agents Chemother. 48:1908-1911 (2004)]. For both immunocompetent and neutropenic mice differences in survival between vaccinated and adjuvant vaccinated mice were compared by the Log Rank test.

For passive immunization, immune IgG was administered intraperitoneally to naïve mice 2 h before infecting i.v. with *C. albicans*. Control mice were given isotype matching IgG (Innovative Research, USA). IgG doses were repeated 3 days after infection, and survival of mice was monitored twice daily.

Quantitative culturing of kidneys from vaccinated or control mice infected with different species of *Candida* was performed as previously described [Ibrahim et al., Infect. Immun. 74:3039-3041 (2006)]. In brief, mice were infected through tail veins. Kidneys were harvested 3 day post infection, homogenized, serially diluted in 0.85% saline, and quantitatively cultured on YPD that contained 50 μg/mL chloramphenicol. Colonies were counted after incubation of the plates at 37° C. for 24 to 48 h, and results were expressed as log CFU per gram of infected organ.

Concomitant with the fungal burden experiment, kidneys were removed aseptically from two mice per group for histopathological examination. Kidneys were immersed in zinc formalin fixative until examination. Fixed organs were dehydrated in graded alcohol solutions, embedded in paraffin, and cut into 6-μm-thick sections. Mounted sections were stained with Gomori methenamine silver and examined by light microscopy [Davis et al., Infect. Immun. 68:5953-5959 (2000)].

Enzyme-Linked Immunosorbent Assay (ELISA)

To test if the rHyr1p-N vaccine induced an immune response, antibody titers of serum samples collected from vaccinated and control mice were determined by ELISA in 96-well plates as previously described [Ibrahim et al., Infect. Immun. 73:999-1005 (2005)]. Wells were coated at 100 μl per well with rHyr1p-N at 5 μg/ml in PBS. Mouse sera were incubated for 1 h at room temperature following a blocking step with Tris-buffered saline (TBS; 0.01 M Tris HCl [pH 7.4], 0.15 M NaCl) containing 3% bovine serum albumin. The wells were washed three times with TBS containing 0.05% Tween 20, followed by another three washes with TBS. Goat anti-mouse secondary antibody conjugated with horseradish peroxidase (Sigma) was added at a final dilution of 1:5000, and the plate was further incubated for 1 h at room temperature. Wells were washed with TBS and incubated with substrate containing 0.1 M citrate buffer (pH 5.0), 50 mg of o-phenylenediamine (Sigma), and 10 μl of 30% $H_2O_2$. The color was allowed to develop for 30 min, after which the reaction was terminated by addition of 10% $H_2SO_4$ and the optical density (OD) at 490 nm was determined in a microtiter plate reader. Negative control wells received only diluent, and background absorbance was subtracted from the test wells to obtain final OD readings. The ELISA titer was taken as the reciprocal of the last serum dilution that gave a positive OD reading (i.e., more than the mean OD of negative control samples plus 2 standard deviations).

F(ab')$_2$ Blocking Assay

To study the mechanism of protection mediated by anti-Hyr1p antibodies in phagocyte-mediated killing of *C. albicans*, HL-60 cells that have been differentiated to neutrophil-like phenotype were used [Luo et al., J. Infect. Dis. 201: 1718-1728 (2010)]. Killing assay was conducted in the presence of anti-Hyr1p IgG or F(ab')$_2$ fragments as described before [Luo et al., J. Infect. Dis. 201: 1718-1728 (2010)]. In brief, HL-60 cells were induced with 2.5 μM of retinoic acid and 1.3% DMSO for three days at 37° C. with 5% $CO_2$. Immune anti-Hyr1 peptides (Table 1) sera were pooled and total IgG was isolated using protein A agarose (Thermo Scientific). Serum collected from the same rabbits prior to immunization with the peptides served as control serum. The F(ab')$_2$ fragments from immune or control IgG were purified with Pierce F(ab')$_2$ Preparation Kit according to the manufacturer's instruction. SDS-PAGE analysis indicated >95% of Fc fragment was digested by this kit (data not shown). Next, *C. albicans* cells overexpressing or suppressing Hyr1p [Luo et al., J. Infect. Dis. 201: 1718-1728 (2010)] were incubated with 50 μg/ml of vaccinated or control F(ab')$_2$ fragments on ice for 45 min. *C. albicans* cocultured with the F(ab')$_2$ fragments were incubated with HL-60 derived neutrophils for 1 h at 37° C. with 5% $CO_2$ prior to sonication and quantitative culturing on YPD plates. % killing was calculated by dividing the number of CFU after coculturing with HL-60 derived neutrophils by the number of CFU from *C. albicans* incubated with media without neutrophil-like cells.

Statistical Analysis

The nonparametric log rank test was used to determine differences in the survival times of the mice. Neutrophil killing assay, titers of antibody, and tissue fungal burden were compared by the Mann-Whitney U test for unpaired comparisons. Correlations were calculated with the Spearman rank sum test. P values of <0.05 were considered significant.

All procedures involving mice were approved by the Los Angeles Biomedical Research Institute animal use and care committee for the project 11672-05 specifically to this vaccine study, following the National Institutes of Health guidelines for animal housing and care. The institute has a US Public Health Service approved animal welfare assurance number A3330-01.

Results

The rHyr1p-N Vaccine Significantly Improved Survival and Decreased Fungal Burden in Immunocompetent Mice Challenged i.v. with *C. Albicans*.

To determine the most effective dose of the rHyr1p-N immunogen, a 3-fold dose range was evaluated (1 to 30 μg per mouse). Female juvenile BALB/c mice were immunized with rHyr1p-N plus alum (2% Alhydrogel; Brenntag Biosector) or with alum alone. These mice were subsequently infected with a lethal inoculum of *C. albicans* ($7 \times 10^5$ blastospores). Vaccinated mice had significant improvements in survival compared to adjuvant control mice (FIG. 1A). All tested doses, except 1 μg, prolonged or improved survival compared to mice receiving adjuvant alone, and a dose response was found with 10 and 30 μg having the greatest efficacy (FIG. 1A). The experiment was terminated on day 28, with all remaining mice appearing healthy.

To determine the impact of vaccination on fungal burden, juvenile mice were vaccinated and infected as above. On day 3 post-infection (one day before the control mice were predicted to die based on the previous experiment), mice were euthanized and kidneys, being the primary target organ, were harvested to determine tissue fungal burden. Vaccination reduced the tissue fungal burden by approximately 16-fold compared to control mice (p<0.01) (FIG. 1B).

Figure 2:
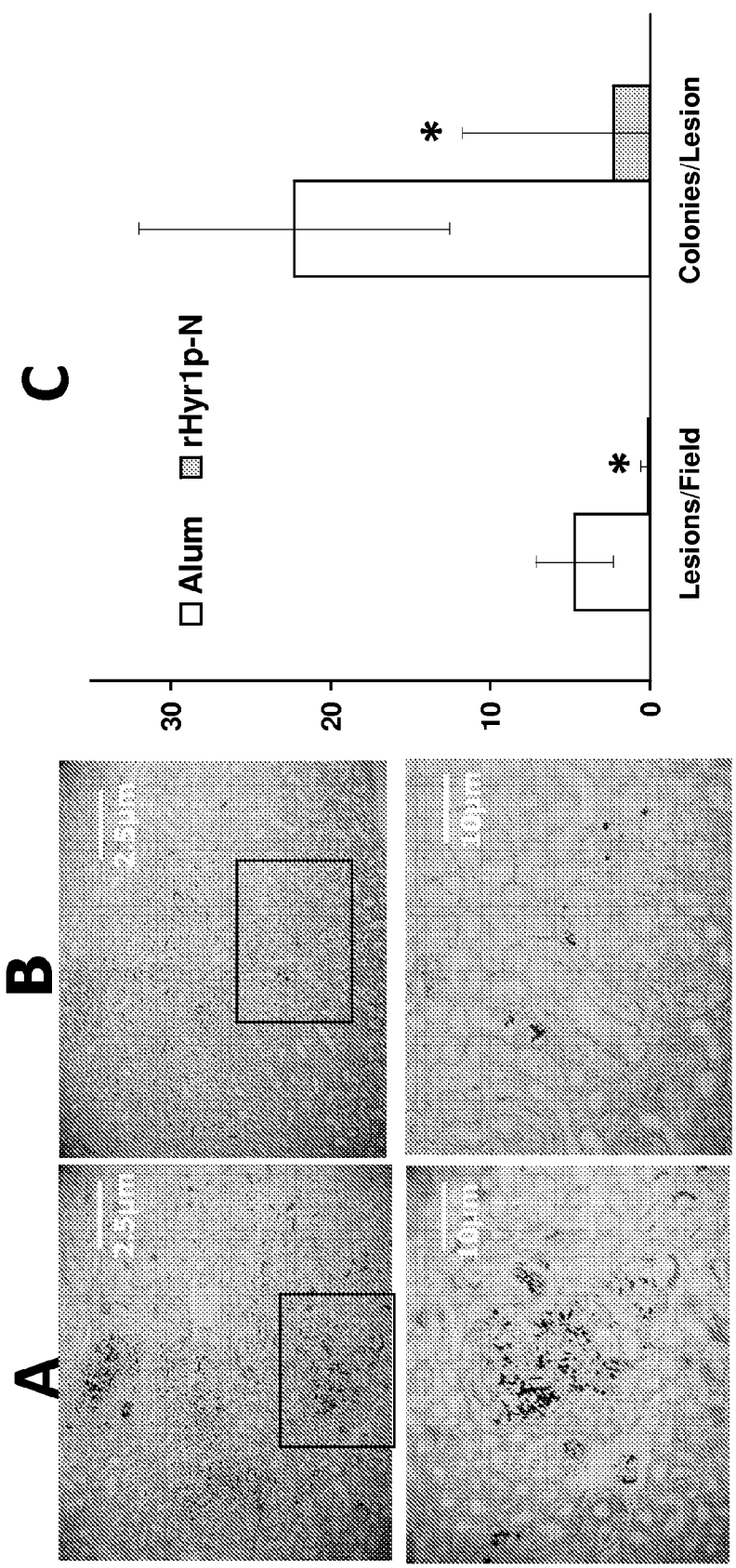
FIGS. 2A-2C: Representative histopathological sections from kidneys are shown. (A) Control mice infected with *C. albicans* had multiple abscesses showing mostly yeast forms with some hyphae and pseudohyphae throughout the kidneys. (B) rHyr1p-N vaccinated mice (30 μg) infected with *C. albicans* had less abscesses with far less fungi visible. (C) Semiquantitative evaluation of the severity of infection indicated a significant abscess and *Candida* cells reduction in vaccinated mice compared to control mice. Sections were stained by PAS. Thirty random fields were examined by a blinded assessor (GL) to assess the number of lesions per field. Number of organisms per lesion was evaluated in 120 lesions in the control unvaccinated mice. The average number of organisms per lesion was determined by dividing the total number of fungal cells by the number of lesions counted.

Consistent with the survival and fungal burden data, histopathological examination of kidneys harvested from rHyr1p-N vaccinated mice demonstrated very few abscesses with minimal fungal residues mainly present in the blastospore formation (FIG. 2B). In contrast, numerous abscesses full of fungal cells showing mostly yeast forms with some hyphae and pseudohyphae were detected in kidneys taken from mice vaccinated with alum alone (FIG. 2A). Semi-quantitative evaluation of the severity of infection showed a significant reduction of abscesses per field as well as reduced *Candida* cells per abscess in vaccinated mice compared to that in controls (FIG. 2C, P<0.0001 by Wilcoxon rank sum test).

The rHyr1p-N Effectively Protected Immunocompromised Mice Against Candidiasis

Figure 3:
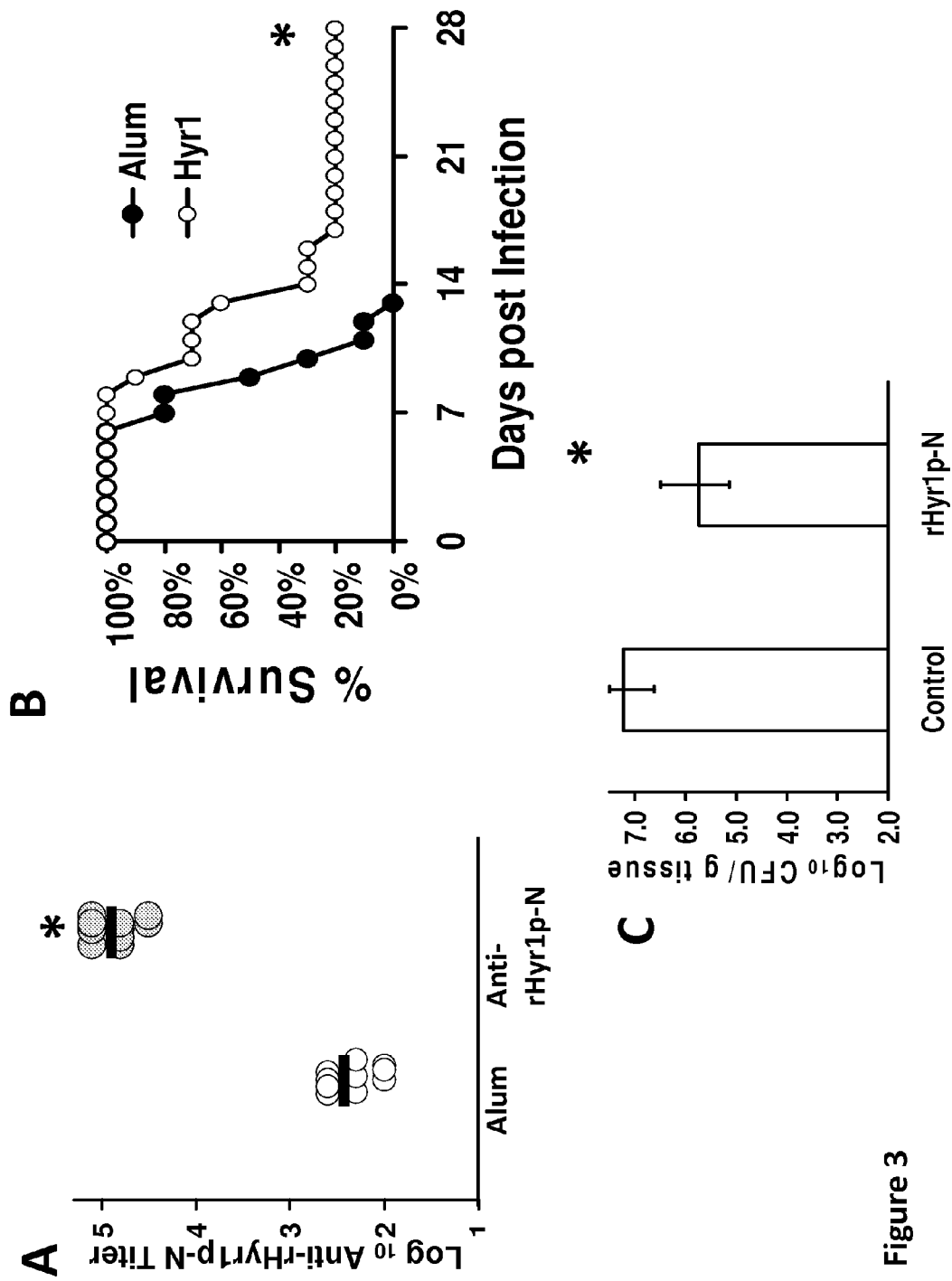
FIGS. 3A-3C: rHyr1p-N vaccine prolonged survival and decreased fungal burden in neutropenic mice infected with *C. albicans*. Balb/c mice (n=20 per arm) were vaccinated with rHyr1p-N mixed with alum or alum alone, treated with cyclophosphamide, then infected with *C. albicans* 15563 at $1 \times 10^5$ blastospores. Two days before cyclophosphamide treatment, half of the mice were bled and individually marked for antibody titer using ELISA (A) and survival (B). The other half mice were used for fungal burden (C). *p<0.05 for vaccinated vs. control by Log Rank test.

It is known that a significant fraction of immunocompromised patients do respond to a variety of vaccines [Dockrell et al., Vaccine 17:2779-2785 (1999); Chokephaibulkit et al., Vaccine 22:2018-2022 (2004); dos Santos et al., AIDS Res. Hum. Retroviruses 20:493-496 (2004); King et al., Pediatrc. Infect. Dis. 15:192-196 (1996)]. We sought to define the potential usage of the rHyr1p-N vaccine to protect neutropenic mice from disseminated candidiasis. Immunized mice were bled twelve days following the boost with 30 mg of rHyr1p-N. Vaccination significantly increased the mouse immune response as determined by detection of increased anti-rHyr1p-N antibody titers (FIG. 3A). One day after the bleeding, mice were made neutropenic. Vaccination resulted in significant improvements in survival (P=0.007 by log rank test versus control) (FIG. 3B).

We also evaluated the kidney fungal burden on day 10 post infection. Concordant with our survival result, we found that mice vaccinated with 30 μg of rHyr1p-N had 1.50 log fold decrease in fungal burden compared to kidneys harvested from control mice (FIG. 3C, P=0.0021 by Wilcoxon rank-sum test).

Passive Immunization with Anti-Hyr1 IgG Prolonged the Survival of Mice Infected with *C. Albicans*

Figure 4:
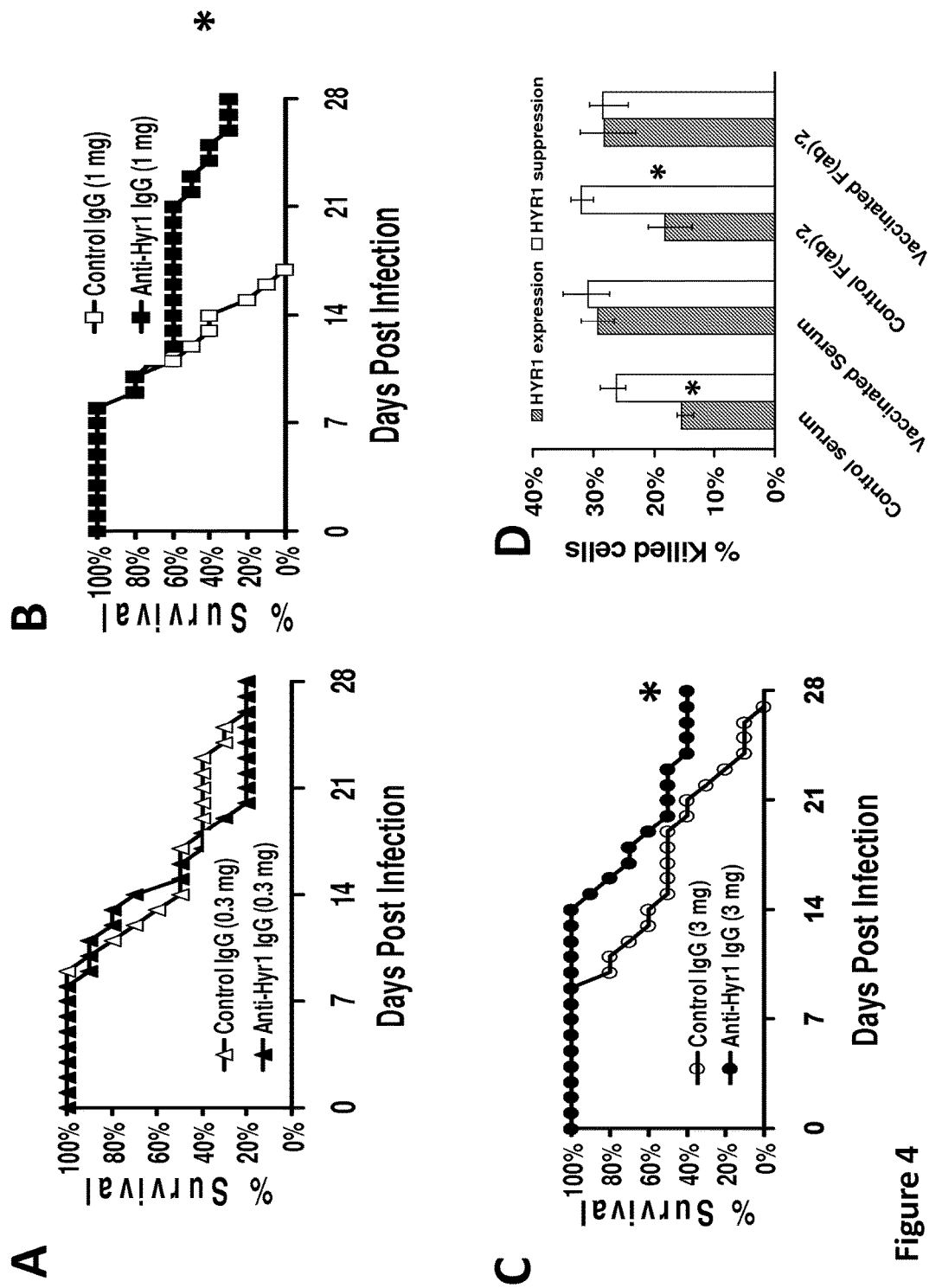
FIGS. 4A-4D: Dose dependent passive immunization with anti-Hyr1p IgG protected against murine hematogenously disseminated candidiasis. Mice were given 0.3 mg (A), 1 mg (B) and 3 mg (C) of anti-Hyr1p IgG through i.p 2 hour before infecting with $6.2 \times 10^5$ blastospores of *Candida albicans* 15563 via the tail vein. Survival of mice (n=10 per group) was monitored twice daily. *P=0.001 by log-rank test vs. mice receiving isotype-match control IgG. (D) Effect of vaccinated or control F(ab')$_2$ on blocking HL-60 derived neutrophil killing of *C. albicans*. *C. albicans* overexpressing or suppressing Hyr1p were used in the assay to demonstrate specificity of the F(ab')$_2$ fragments to Hyr1p. Control denotes assay performed in the absence of either F(ab')$_2$ or the presence of F(ab')$_2$ from isotype matching IgG. Data are displayed as median±interquartile range. *P=0.001 by Mann-Whitney test.

Since some patients might not respond to an active vaccine strategy, we evaluated the possibility of using passive immunotherapy targeting Hyr1p. We generated polyclonal antibodies by vaccinating rabbits with 8 hydrophilic, highly antigenic 14-mer peptides located within rHyr1p-N region (Table 1). Purified IgG targeting these 8-hydrophilic peptides were pooled and used to treat naïve mice infected with a lethal dose of *C. albicans*. Mice receiving anti-Hyr1p IgGs at either 1 or 3 mg (but not when administered at 0.3 mg) were protected substantially from infection when compared to mice receiving non-specific, control IgG from commercial source (FIGS. 4A, B and C).

To determine if the generated anti-Hyr1p antibodies enhanced phagocyte function by increasing opsonophagocytosis or by neutralizing the Hyr1p virulence function, we isolated and prepared F(ab')$_2$ fragments from pooled IgG raised against the 8 peptides of Hyr1p or from isotype-matching control IgG. These fragments were used in HL-60 derived neutrophil killing assay against *C. albicans* conditionally overexpressing or suppressing Hyr1p rather than wild-type *C. albicans* to demonstrate specificity of these fragments to Hyr1p and not to other members of Iff family [d'Enfer et al., Nucleic Acids Res. 33:D353-357 (2005)]. Consistent with our previous mouse IgG data [Luo et al., J. Infect. Dis. 201: 1718-1728 (2010)], we found that F(ab')$_2$ fragments prepared from anti-Hyr1p antibodies but not those prepared from control antibodies were able to restore HL-60 derived neutrophil killing of the HYR1 conditional expressing strain to levels equivalent to that of the suppressing strain (FIG. 4D).

Figure 5:
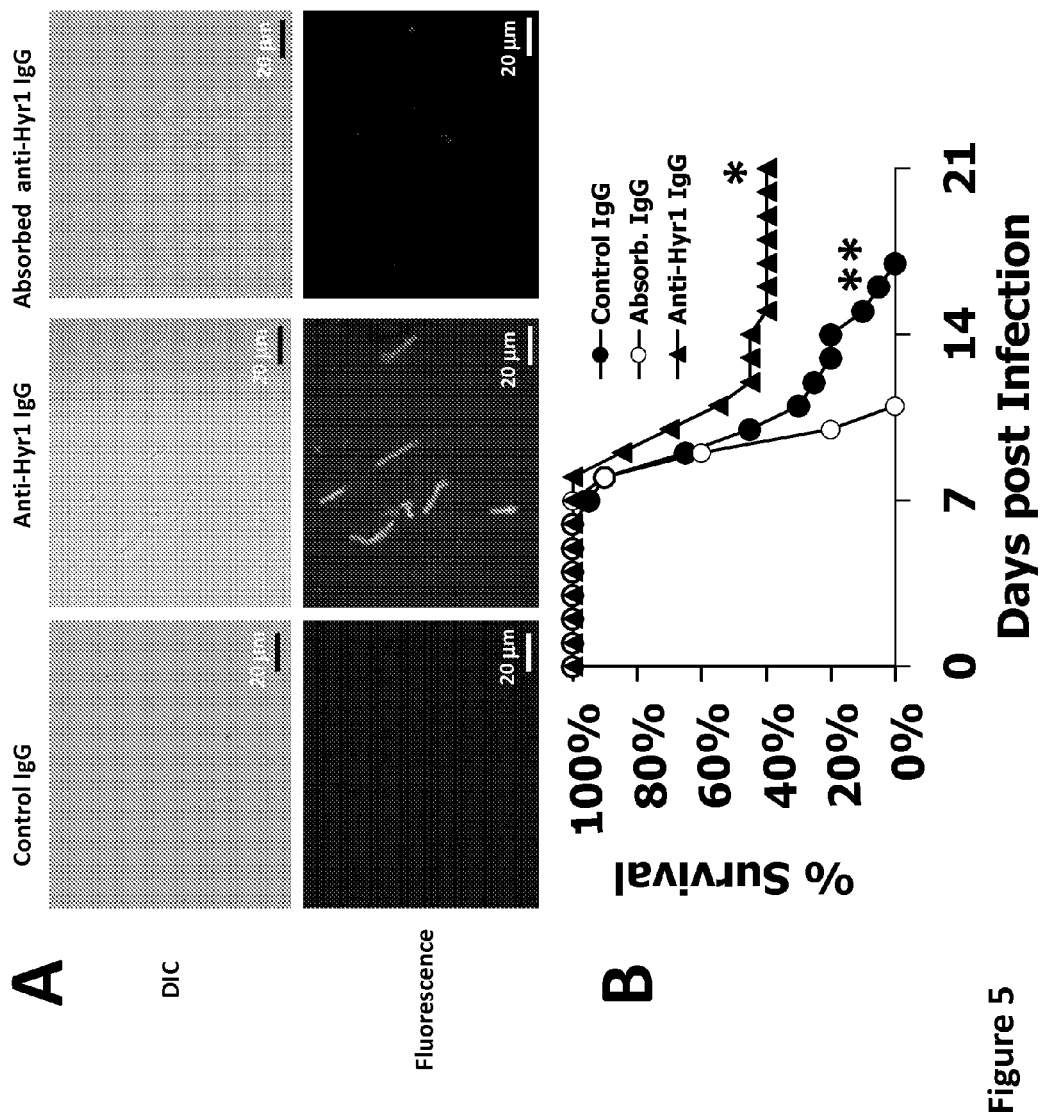
FIGS. 5A-5B: Protection against hematogenously disseminated candidiasis using purified pooled IgG is specific to Hyr1p. A) Indirect immunofluorescence with rabbit anti-Hyr1p IgGs demonstrated surface expression of Hyr1p on *C. albicans* hyphae and the successful absorption of anti-Hyr1p antibodies; B) Survival of mice treated with 1 mg of: 1) pooled anti-Hyr1 IgGs (n=20); 2) pooled anti-Hyr1p IgG absorbed with *C. albicans* hyphae (n=10); or 3) control rabbit IgG (n=20) two hours before infecting with 8.7×10$^5$ blastospores of *C. albicans* 15563 via the tail vein. The antibody dose was repeated 3 days after infection. * p=0.002 vs. absorbed IgG and 0.03 vs. control IgG, ** p=0.28 vs. absorbed IgG by Log Rank test.

To verify that the protection elicited by antibodies was indeed due to anti-Hyr1p antibodies and not due to non-specific protection caused by antibodies reacting to unrelated immunogen (e.g. antibodies against KLH), the purified IgG targeting the 8 hydrophilic rHyr1p-N peptides was absorbed with *C. albicans* hyphae prior to testing for their protective activity against hematogenously disseminated candidiasis. The absorbed IgG did not stain *C. albicans* hyphae (FIG. 5A), indicating the anti-Hyr1p IgG were eliminated. Furthermore, similar to control IgG (i.e. non-specific IgG from commercial source), the absorbed IgG did not protect mice from *C. albicans* infection, whereas the unabsorbed purified IgG did (FIG. 5B, p=0.002). These results confirm the specificity of the anti-rHyr1p antibodies in protecting against hematogenously disseminated candidiasis.

The rHyr1p-N Vaccine Substantially Reduced Tissue Fungal Burden in BALB/c Mice Challenged with Several Non-*Albicans* Species of *Candida*.

Figure 6:
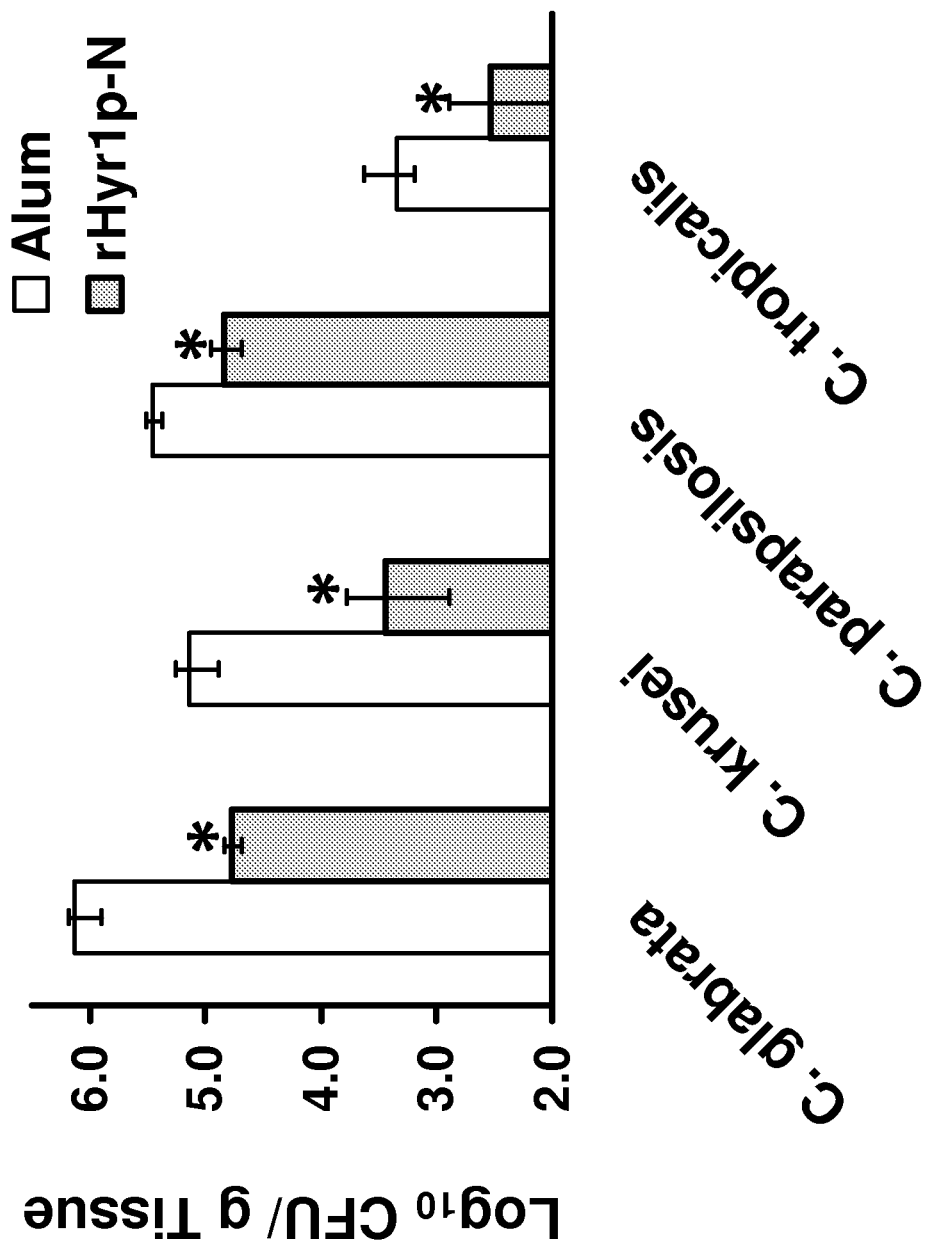
FIG. 6: rHyr1p-N vaccine reduces tissue fungal burden in BALB/c mice infected with non-*albicans* species of *Candida*. BALB/c mice (n=10 per group) were vaccinated with alum or alum plus rHyr1p-N (30 µg) and boosted three weeks later. Two weeks after the boost, mice were challenged via the tail vein with *C. glabrata* (3.2×10$^7$), *C. krusei* (3.4×10$^7$), *C. parapsilosis* (9.6×10$^6$), or *C. tropicalis* (3.2× 10$^6$). Kidney fungal burden was determined on day 3 post infection. The y axis reflects the lower limit of detection of the assay. * P<0.001 versus adjuvant control by the Mann-Whitney U test.

A vaccine that elicits protection against *C. albicans* and other non-*albicans* species is highly desirable because a significant number of *Candida* infections are caused by non-*albicans* species. For example, *C. glabrata* represents the second most common cause of candidiasis and *C. krusei* is resistant to azole therapy. Using blast searches we were able to detect Hyr1p-N orthologs in several *Candida* species with amino acid similarity ranging between 47-72% in certain area. Thus, we vaccinated mice with rHyr1p-N plus alum as above, then challenged with *C. albicans, C. glabrata, C. krusei, C. parapsilosis,* or *C. tropicalis*. Three days post infection mice were sacrificed and the kidneys harvested for determination of tissue fungal burden through colony counts. Mice vaccinated with rHyr1p-N had 0.65-1.69 log decrease in kidney fungal burden compared to mice vaccinated with alum alone (FIG. 6).

We have identified properties of the recombinant N-terminus of Hyr1p (rHyr1p-N) [Luo et al., J. Infect. Dis. 201: 1718-1728 (2010)] that make it useful as both active and passive immunotherapy target. Rabbit polyclonal IgG raised against 8 different 14-mer peptides from regions of rHyr1p-N substantially protects mice from experimental disseminated candidiasis. Furthermore, the rHyr1p-N maintained its efficacy in the neutropenic mouse model.

Tissue fungal burden and histopathological examination of kidneys harvested from mice vaccinated with rHyr1p-N or alum alone further confirmed the efficacy of the rHyr1p-N vaccine. However, the histopathology difference between control (FIG. 2A) and rHyr1p-N vaccinated mice (FIG. 2B) was far more prominent than that of tissue fungal burden of the same organs. In this regard, it has been previously reported that colony counting can underestimate the tissue fungal burden in the presence of hyphae and pseudohyphae [Spellberg et al., J. Leukoc. Biol. 78:338-344 (2005), Spellberg et al., J. Infect. Dis. 194:256-260 (2006)], likely because tissue homogenization kills fungal filaments. We found that control mice had significantly more filamentous fungi in kidneys than vaccinated mice which had less abscesses mainly consisting of yeast form fungal elements. Therefore, tissue homogenization likely artificially lowers the colony counts for kidneys harvested from control mice but not from rHyr1p-N-vaccinated mice, making the difference less prominent.

Our results also show a dose response of anti-Hyr1p IgG in protecting mice from disseminated candidiasis. We also confirmed that the protection elicited by anti-Hyr1p IgG was specific to Hyr1p since absorbed IgG with *C. albicans* hyphae lost its ability to protect mice against hematogenously disseminated candidiasis (FIG. 5B). These results suggest that the mechanism of protection rendered by rHyr1p-N appears to be attributed, at least in part, to protective antibody response.

In this study, we show that pooled IgG raised against 8 Hyr1 peptides directly neutralize the function of Hyr1p in resisting phagocyte killing rather than enhance opsonophagocytosis. This is evident by the ability of F(ab')$_2$ fragments' (prepared from anti-rHyr1p-N antibodies) to restore phagocyte killing of *C. albicans* overexpressing Hyr1p to levels equivalent to that of the suppressing strain (FIG. 4D). However, the rHyr1p-N vaccine maintained its efficacy in neutropenic mice. This can be explained by the fact that cyclophosphamide induces leukopenia in mice with minimal effect on tissue phagocytes.

In summary, the rHyr1p-N vaccine is efficacious in both immunocompetent and immunocompromised mice, when mixed with alum as an adjuvant, against multiple clinical isolated strains of *C. albicans*, and against several non-albicans *Candida* species.

Example II

HYR1 Protein Fragments Prevent Infections by Acinetobacter Baumannii

*Candida albicans* is a diploid fungus that grows both as yeast and filamentous cells. *C. albicans* causes approximately 60,000 cases of disseminated candidiasis per year in the United States. The *C. albicans* HYR1 protein is a cell surface protein that confers phagocyte resistance to fungal cells by white blood cells during fungal infections. Vaccination with a recombinant HYR1 protein has been shown to protect mice against *Candida* infection. Moreover, passive immunization with anti-HYR1 protein antibodies protects against hematogenously disseminated candidiasis.

Through predictive structure homology modeling, the *C. albicans* HYR1 protein was discovered to have considerable homology to several proteins from gram negative bacteria, including *Acinetobacter baumannii*. Consequently, the feasibility of using active and passive immunization targeting HYR1 protein in protecting against *Acinetobacter baumannii* was examined.

Figure 7:
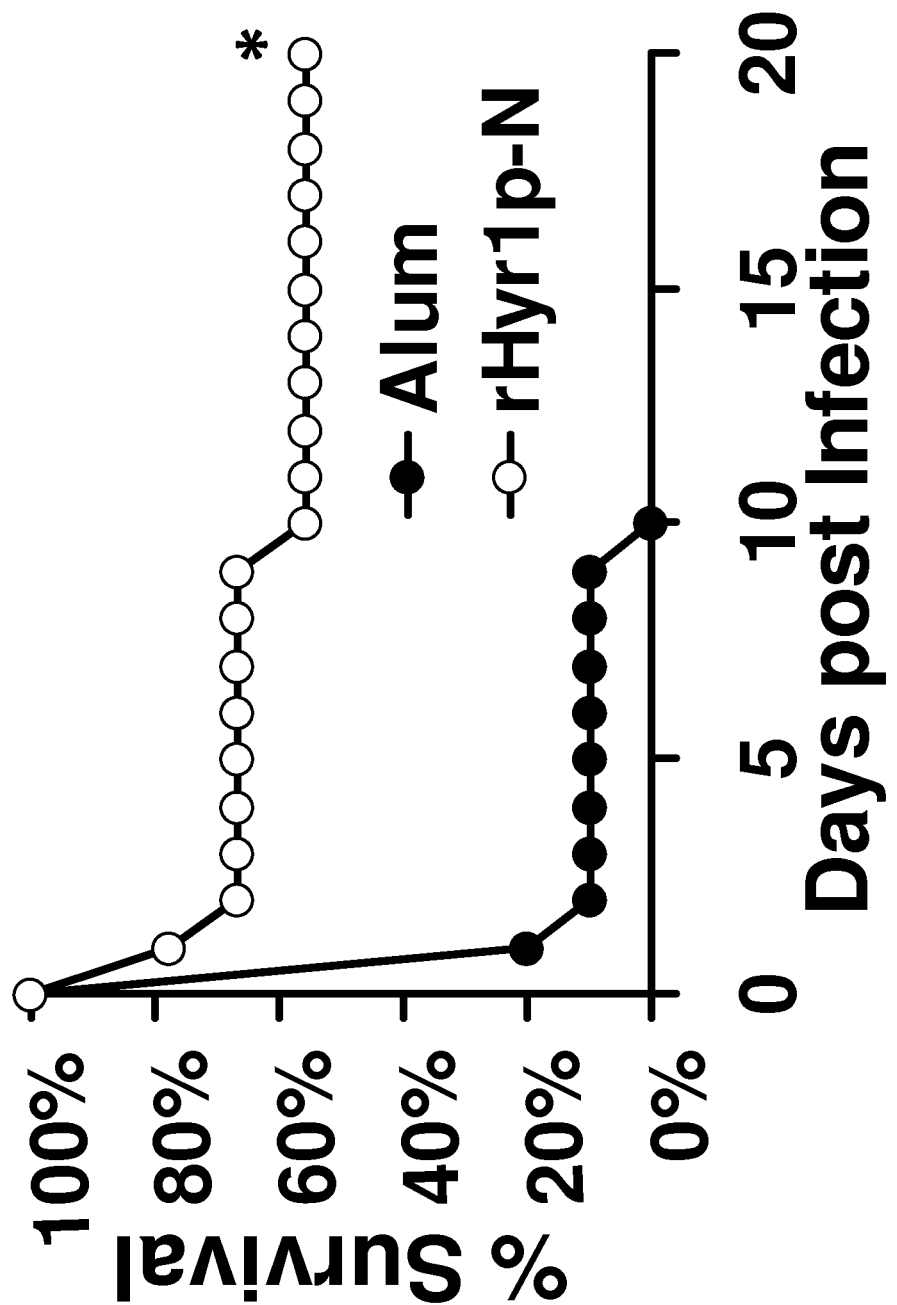
FIG. 7 shows active immunization with rHYR1p-N (SEQ ID NO: 2) protects diabetic mice from *Acinetobacter baumannii* bacteremia. Mice were immunized with aluminum hydroxide alone (n=10) or rHYR1p-N (30 mg) mixed with aluminum hydroxide (n=9) on day 0, boosted on day 21 and infected with *Acinetobacter baumannii* on day 35. * P<0.005 vs. control.
Figure 8:
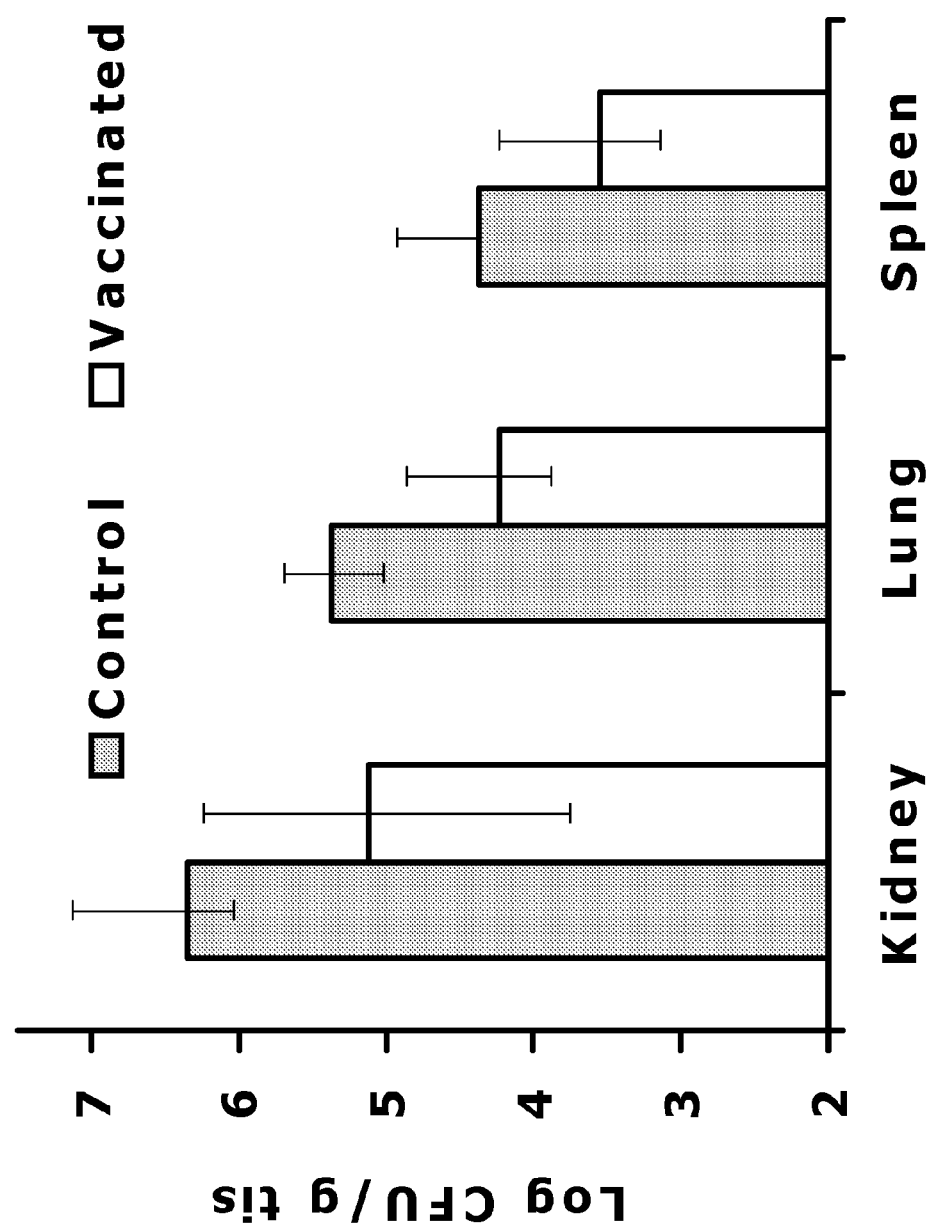
FIG. 8 shows the effect of active vaccination with rHYR1p-N (SEQ ID NO: 2) on bacterial burden in kidney, lung and spleen tissue. Control mice were immunized with aluminum hydroxide alone, whereas vaccinated mice were immunized with rHYR1p-N (30 mg) mixed with aluminum hydroxide on day 0, boosted on day 21 and infected with *Acinetobacter baumannii* on day 35.

Three-dimensional structure homology studies were conducted using convergent methods of structural homology modeling. These include multiple sequence alignment, threading to structural homologues based on sequence identity and similarity, and three dimensional structural modeling. This analysis revealed that the full length Candidal HYR1 polypeptide has significant homology to proteins from several gram negative bacteria including *Haemophilus, Bordetella, Salmonella, Bordetella, Yersina, Escherichia* and *Acinetobacter* species (Table 3).

survival compared to 10% survival in the control arm (p<0.05 by Log Rand test) (FIG. 7). Additionally, the bacterial burden in the tissue of mice vaccinated and infected similarly was examined. The bacterial burden as measured by the number of colony forming units per gram of tissue showed that tissue isolates from kidney, lung and spleen had a lower bacterial burden as compared to control tissue samples (FIG. 8).

Polyclonal antibodies were next raised in rabbits against eight specific polypeptide regions chosen from the HYR1 protein. These regions were structurally mapped to be exposed hydrophilic regions when expressed by *C. albicans* and predicted to be highly antigenic. The eight specific polypeptide regions consisted of 14 amino acid residues plus an additional cysteine residue on either the N-terminus or the C-terminus of the polypeptide (Table 2). The terminal cysteine residues provided for attachment to the carrier protein, Keyhole limpet hemocyanin (KLH), which was used for production of the polyclonal antibodies.

Figure 9:
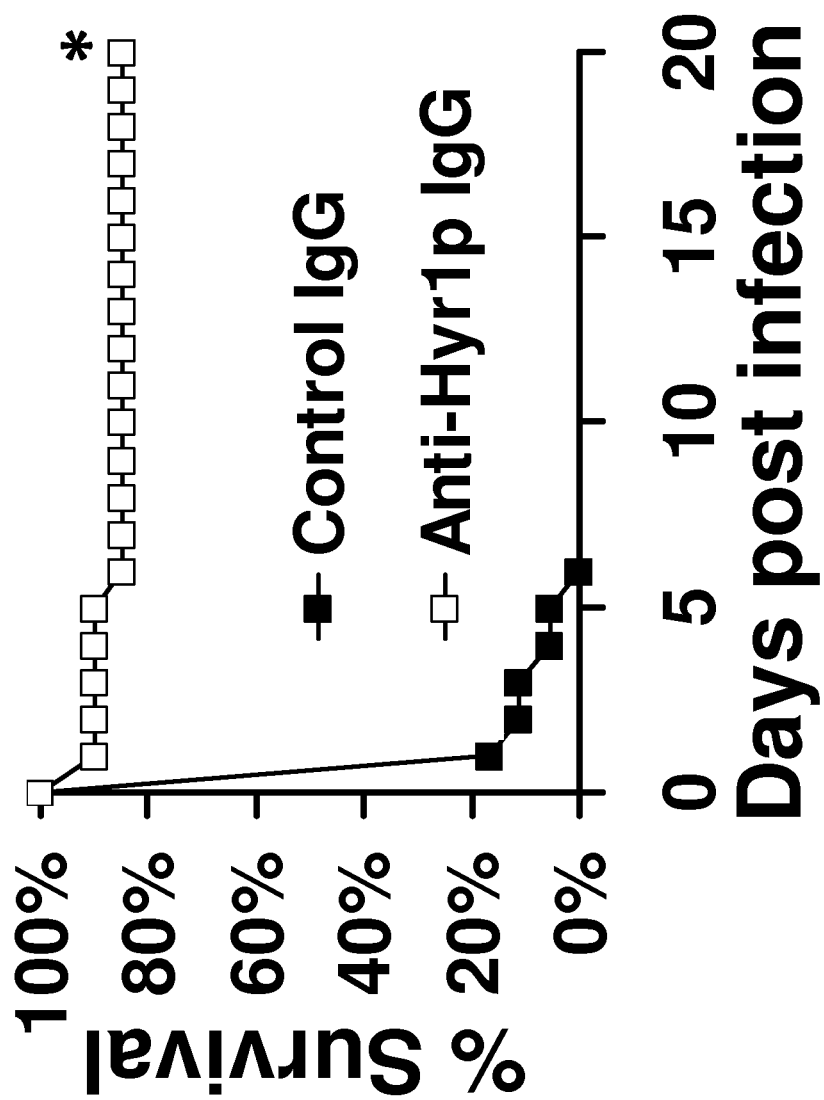
FIG. 9 shows passive immunization protects diabetic mice from *Acinetobacter baumannii* bacteremia. Mice were treated with 1 mg rabbit control IgG (n=18) as a control. Experimental mice were treated with pooled polyclonal anti-rHYR1p IgG (n=20) 2 h prior to infecting with *A. baumannii*. Each of the polyclonal anti-rHYR1p antibodies comprising the pool were raised against one of synthetic antigenic polypeptide comprising one of SEQ ID NOS: 11-18. * P<0.005 vs. control IgG.

Overall passive immunization against *Acinetobacter baumannii* infection was assayed in diabetic mice. Purified IgG from the eight different polyclonal antibodies generated above were pooled and given to diabetic mice (n=20) 2 hours prior to infection. Commercially available unrelated rabbit IgG was given to diabetic control mice (n=18). The mice were then infected with a lethal dose of *Acinetobacter baumannii* via tail vein injection. Mice receiving a single dose of the anti-Hyr1p IgG survived significantly longer than mice receiving the control IgG (i.e.—80% survival in the anti-Hyr1p IgG vs. 0% in the control arm, p<0.0001 by Log Rank test) (FIG. 9).

Passive immunization with polyclonal antibodies against individual amino acid sequences were also assayed in diabetic mice infected by *Acinetobacter baumannii*. Two hours prior to infection, diabetic mice were treated with 1 mg of rabbit control IgG (n=18) or polyclonal anti-HYR1 polypeptide IgG raised individually against one of eight different synthetic HYR1 peptides (Table 2). Additionally, two separate combination pools of antibodies were assayed. Combi-

TABLE 3

Homology Modeling of Hyr1 Vaccine Primary and Secondary Structure

| PDB Code (Link) | Identity | e Value | Precision | Superfamily | Specific Homologue | Original Source Pathogen |
| --- | --- | --- | --- | --- | --- | --- |
| 2odL | 12% | 0.0016 | 95% | Chain A adhesin | HMW1 virulence factor | *Haemophilus influenzae* (G−) |
| 1daB | 11% | 0.06 | 95% | Pectin-Lyase | Virulence p69 pertactin | *Bordetella pertussis* (G−) |
| 1wlG | 7% | 0.11 | 90% | Flagellar body | Flagellar hook (flgE) | *Salmonella typhimurium* (G−) |
| 1rwR | 9% | 0.26 | 90% | Pectin-Lyase | FH secretion domain (fhaB) | *Bordetella pertussis* (G−) |
| 1cwV | 8% | 0.37 | 85% | Invasin | Integrin binding protein | *Yersina pseudotuber.* (G−) |
| 1dbQ | 8% | 0.86 | 75% | Chondroitinase | Chondroitinase B | *Escherichia coli* (G−) |
| 1qiU | 14% | 0.93 | 75% | Fiber protein | Adenovirus fiber shaft | Adenovirus (viral) |
| 1rwI | 11% | 1 | 75% | 6-bladed Propeller | Kinase sensor domain | *Mycobact. tuberculosis* (G+) |
| 1ofL | 9% | 1.2 | 70% | Pectin-Lyase | Chondroitinase B | *Pedobacter heparinus* (G−) |
| 2z2O | 7% | 1.4 | 65% | Lyase | Virginiamycin B lyase | *Staphylococcus aureus* (G+) |

Figure 10:
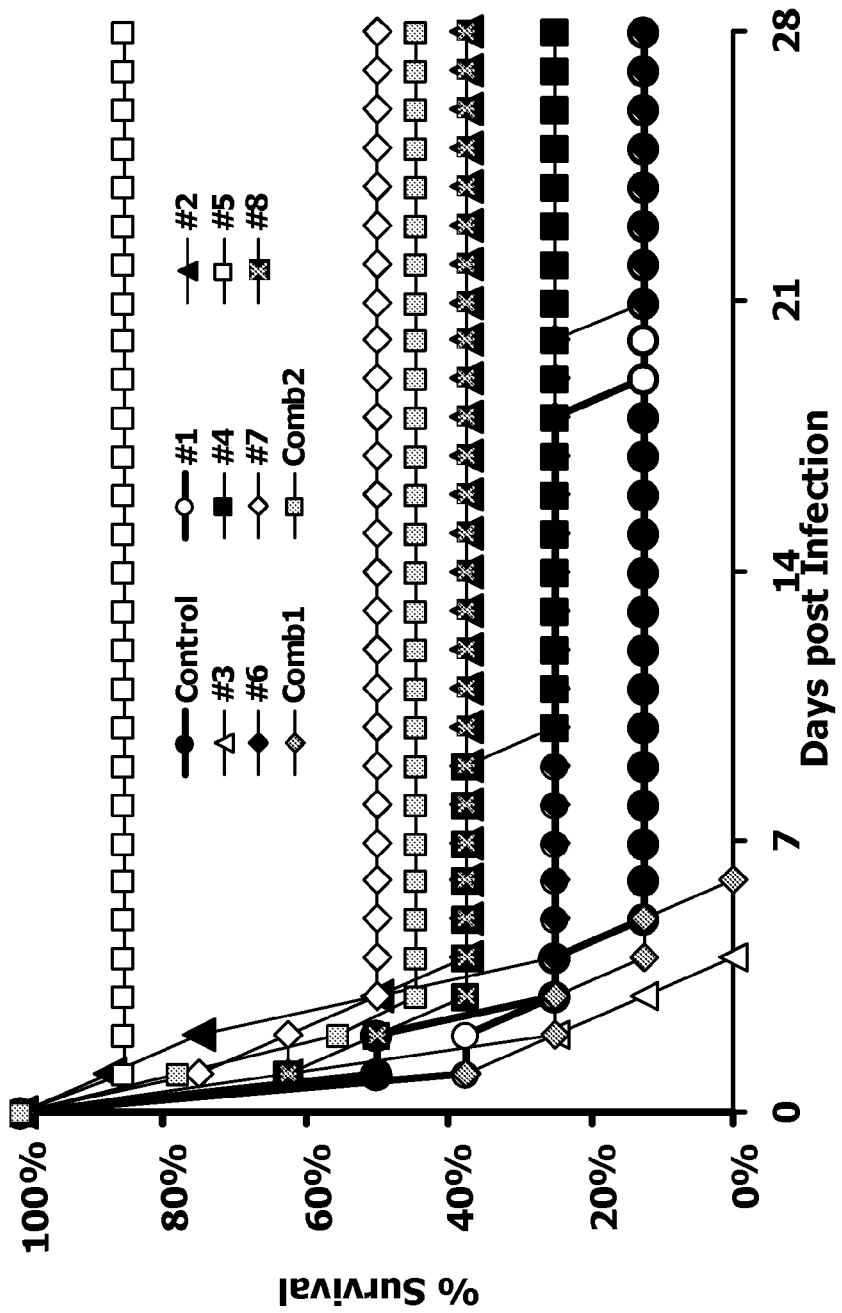
FIG. 10 shows passive immunization protects diabetic mice from *Acinetobacter baumannii* bacteremia. Mice were treated with 1 mg rabbit control IgG (n=18) or polyclonal anti-HYR1p IgG raised individually against one of eight different synthetic HYR1 peptides 2 h prior to infecting with *A. baumannii*. No. 1 was raised against CGPSAPESESDLNTP (SEQ ID NO: 11). No. 2 was raised against CGNRDHFRFEYYPDT (SEQ ID NO: 12). No. 3 was raised against CGYDSKLFRIVNSRG (SEQ ID NO: 13). No. 4 was raised against CKIKGTGCVTADEDT (SEQ ID NO: 14). No. 5 was raised against CLKNAVTYDGPVPNN (SEQ ID NO: 15). No. 6 was raised against NSKSSTSFSNFDIGC (SEQ ID NO: 16). No. 7 was raised against CEPTHNFYLKDSKSS (SEQ ID NO: 17). No. 8 was raised against TSRIDRGGIQGFHGC (SEQ ID NO: 18). Combination 1 (Comb1) includes antibody Nos. 2, 3, 5 and 8. Combination 2 (Comb2) includes antibody Nos. 2, 5 and 8.

Based on the structural analysis studies, rHYR1-N (SEQ ID NO: 2) was produced in *E. coli* and was used to actively vaccinate mice. Mice were immunized with aluminum hydroxide alone (n=10) or rHYR1p-N (30 mg) mixed with aluminum hydroxide (n=9) on day 0, and boosted on day 21. The vaccinated mice were subsequently infected with *A. baumannii* on day 35. The vaccinated mice had a 67% nation 1 included antibody Nos. 2, 3, 5 and 8 and combination 2 included antibody Nos. 2, 5 and 8. Antibodies raised against peptide #5 (SEQ ID NO: 15) protected mice from *Acinetobacter baumannii* infection to a degree similar to the pool of antibodies (i.e. 86% survival with anti-peptide 5 Ab vs. 80% survival with the pooled IgG). The results of these experiments are shown in FIG. 10.

Example III

Anti-HYR1 Antibody Binds Specific Proteins Expressed by *Acinetobacter Baumannii*

Figure 11:
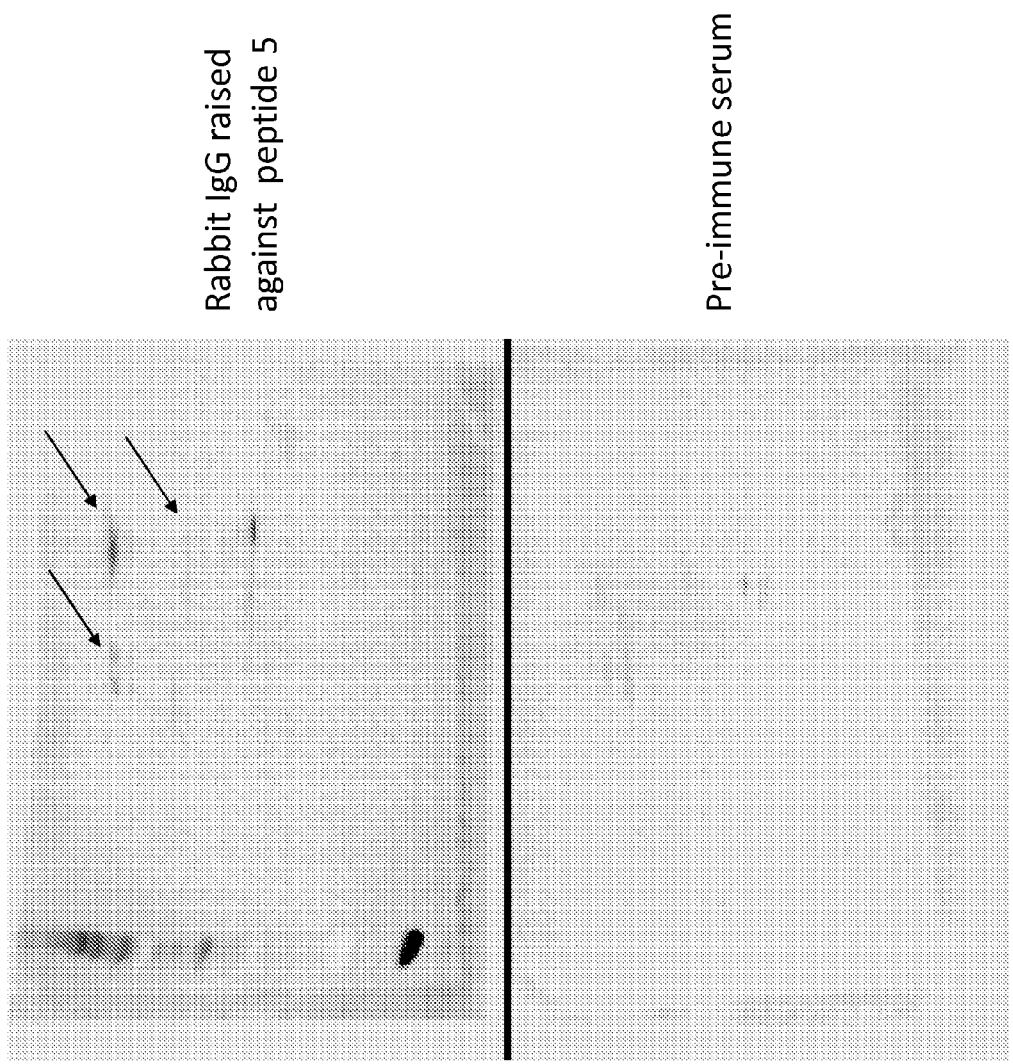
FIG. 11 shows an exemplary 2D-gel and western blot analysis of *Acinetobacter* cell surface extracts. Rabbit IgG raised against CLKNAVTYDGPVPNN (SEQ ID NO: 15) was used to probe the upper blot, whereas pre-immune serum was used as a control to probe the lower blot.

Cell wall extracts from *Acinetobacter baumannii* were run on a two-dimensional gel and assayed by western blot using rabbit IgG raised against CLKNAVTYDGPVPNN (SEQ ID NO: 15). The blots were compared to pre-immune serum as a control. The anti-HYR1 IgG recognized unique bands from cell wall extracts (FIG. 11). Select spots were extracted and sequenced. Sequencing analysis showed that the anti-HYR1 antibody cross reacted with several proteins including an outer membrane protein 1 of *Acinetobacter baumannii* (GI No. |126642014| GenBank ref|YP_001084998.1|) (SEQ ID NO: 19), an outer membrane protein 2 of *Acinetobacter baumannii* (GI No. |126640296| GenBank ref|YP_001083280.1|) (SEQ ID NO: 20), an ferric siderophore receptor protein of *Acinetobacter baumannii* (including GI No. |126641700| GenBank ref|YP_001084684.1| (SEQ ID NO: 21); GI No. |126640547| GenBank ref|YP_001083531.1| (SEQ ID NO: 22); GI No. |126643331| GenBank ref|YP_001086315.1|) (SEQ ID NO: 23), an Dnak heat shock protein of *Acinetobacter baumannii* (GI No. |126642981| GenBank ref|YP_001085965.1|) (SEQ ID NO: 24), elongation factor G of *Acinetobacter baumannii* (GI No. |126640918| GenBank ref|YP_001083902.1|) (SEQ ID NO: 25), organic solvent tolerance protein precursor of *Acinetobacter baumannii* (GI No. |126641591| GenBank ref|YP_001084575.1|) (SEQ ID NO: 26), putative lipoprotein precursor (VacJ) transmembrane of *Acinetobacter baumannii* (GI No. |126640689| GenBank ref|YP_001083673.1|) (SEQ ID NO: 27), putative glucose-sensitive porin (OprB-like) of *Acinetobacter baumannii* (GI No. |126642873| GenBank ref|YP_001085857.1|) (SEQ ID NO: 28), AdeA membrane fusion protein of *Acinetobacter baumannii* (GI No. |126641797| GenBank ref|YP_001084781.1|) (SEQ ID NO: 29), cell division protein of *Acinetobacter baumannii* (GI No. |126643339| GenBank ref|YP_001086323.1|) (SEQ ID NO: 30), and cell division protein FtsZ of *Acinetobacter baumannii* (GI No. |126643338| GenBank ref|YP_001086322.1|) (SEQ ID NO: 31).

Other Embodiments

All publications including GenBank and GI number publications, patents, and patent applications mentioned in the above specification are hereby incorporated by reference. Various modifications and variations of the described methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

---

The invention claimed is:

1. An isolated polypeptide comprising the amino acid sequence of SEQ ID NO:7, or a variant sequence thereof having up to three amino acid substitutions to the amino acid sequence of SEQ ID NO:7, wherein the N-terminal amino acid residue or C-terminal amino acid residue of said polypeptide is cysteine.

2. An isolated polypeptide comprising the amino acid sequence of SEQ ID NO:7, or a variant sequence thereof having up to three amino acid substitutions to the amino acid sequence of SEQ ID NO:7, wherein (i) said polypeptide does not comprise more than 20 contiguous amino acids of SEQ ID NO:2, and (ii) the isolated polypeptide is conjugated to a carrier.

3. The isolated polypeptide of claim 2, wherein said carrier is keyhole limpet hemocyanin (KLH), CRM197, or tetanus toxoid.

4. The isolated polypeptide of claim 2, wherein said carrier is a phage, a yeast, a virus, virosome, a recombinant virus-like particle, or a heterologous recombinant protein.

5. A composition comprising: (i) an isolated polypeptide comprising the amino acid sequence of SEQ ID NO:7, or a variant sequence thereof having up to three amino acid substitutions to the amino acid sequence of SEQ ID NO:7, wherein said polypeptide does not comprise more than 20 contiguous amino acids of SEQ ID NO:2, and (ii) an immuno-effective amount of an adjuvant.

6. The composition of claim 5, wherein said polypeptide is produced synthetically, or wherein said polypeptide is produced recombinantly.

7. A method of inducing an immune response in a mammal comprising administering to said mammal the composition of claim 5, thereby inducing an immune response in said mammal, wherein the isolated polypeptide comprises the amino acid sequence of SEQ ID NO:7.

8. The method of claim 7, wherein the immune response in the mammal is directed against Acinetobacter baumannii.

9. A composition comprising an immunogenic amount of the isolated polypeptide of claim 2, and a pharmaceutically acceptable excipient.

10. The composition of claim 9, wherein said polypeptide is produced synthetically; or wherein said polypeptide is produced recombinantly.

11. A method of inducing an immune response in a mammal against Candida albicans comprising administering to said mammal the composition of claim 9, thereby inducing an immune response in said mammal against Candida albicans, wherein the isolated polypeptide comprises the amino acid sequence of SEQ ID NO:7.

12. A method of inducing an immune response in a mammal against Acinetobacter baumannii comprising administering to said mammal the composition of claim 9, thereby inducing an immune response in said mammal against an Acinetobacter baumannii infection, wherein the isolated polypeptide comprises the amino acid sequence of SEQ ID NO:7.

13. The method of claim 7, wherein said mammal is a human.

14. The method of claim 8, wherein said mammal is a human.

15. The method of claim 11, wherein said mammal is a human.

16. The method of claim 12, wherein said mammal is a human.

* * * * *